US008647673B2

(12) United States Patent
Panyam et al.

(10) Patent No.: US 8,647,673 B2
(45) Date of Patent: Feb. 11, 2014

(54) NANOPARTICLES FOR IMAGING AND TREATING CHLAMYDIAL INFECTION

(75) Inventors: Jayanth Panyam, Plymouth, MN (US); Judith A. Whittum-Hudson, Novi, MI (US); Alan P Hudson, Novi, MI (US)

(73) Assignee: Wayne State University, Detroit, MI (US)

( * ) Notice: Subject to any disclaimer, the term of this patent is extended or adjusted under 35 U.S.C. 154(b) by 397 days.

(21) Appl. No.: 12/670,191

(22) PCT Filed: Jul. 23, 2008

(86) PCT No.: PCT/US2008/070901
§ 371 (c)(1),
(2), (4) Date: Jan. 22, 2010

(87) PCT Pub. No.: WO2009/015214
PCT Pub. Date: Jan. 29, 2009

(65) Prior Publication Data
US 2010/0202969 A1    Aug. 12, 2010

Related U.S. Application Data

(60) Provisional application No. 60/951,643, filed on Jul. 24, 2007.

(51) Int. Cl.
*A61K 9/14*    (2006.01)
(52) U.S. Cl.
USPC ........................................................ 424/489
(58) Field of Classification Search
None
See application file for complete search history.

(56) References Cited

U.S. PATENT DOCUMENTS

| 6,432,935 | B1 | 8/2002 | Milankovits | 514/157 |
| 6,475,518 | B1 * | 11/2002 | Baumgart et al. | 424/451 |
| 6,579,854 | B1 * | 6/2003 | Mitchell et al. | 514/31 |
| 6,649,418 | B1 | 11/2003 | Geisberg | 436/518 |
| 2006/0204435 | A1 * | 9/2006 | Stuart | 424/1.49 |
| 2007/0166281 | A1 | 7/2007 | Kosak | 424/85.1 |

OTHER PUBLICATIONS

Anderson et al. J Controlled Release 60, p. 189-198; 1999.*
Pinto-Alphandary et al., Int J Antimicro Agent 13, p. 155-168, 2000.*
McClarty, Grant; Trends in Microbiology 2(5), p. 157-164, 1994.*
Josephson et al., Bioconjugate Chem, 12, p. 554-560, 2002.*
Akpek et al., "Chemokines in Autoimmune Lacrimal Gland Disease in MRL/MpJ Mice," *Invest. Ophthalmol. Vis. Sci.*, 45:185-190, 2004.
Balin et al., "Identification and Localization of *Chlamydia pneumoniae* in The Alzheimer's Brain," *Med. Microbiol. Immunol.* 187:23-42, 1998.
Belland et al., "Transcriptome Analysis of Chlamydial Growth During IFN-Gamma-Mediated Persistence and Reactivation," *PNAS* 100:15971-15976, 2003.
Carabeo et al., "Golgi-Dependent Transport of Cholesterol to the *Chlamydia trachomatis* Inclusion," *PNAS* 100:6771-6776, 2003.

(Continued)

*Primary Examiner* — Nissa Westerberg
(74) *Attorney, Agent, or Firm* — C. Rachal Winger; K&L Gates, LLP

(57) ABSTRACT

Compositions of nanoparticles and targeting moieties for imaging and treating Chlamydial infection are provided, including nanoparticles conjugated to folic acid and comprising at least one antibiotic effective against *Chlamydia*.

8 Claims, 20 Drawing Sheets

(56) References Cited

OTHER PUBLICATIONS

Gerard et al., "*Chlamydia trachomatis* Genes Whose Products Are Related to Energy Metabolism Are Expressed Differentially In Active vs. Persistent Infection," *Microbes and Infection* 4:13-22, 2002.
Gerard et al., "Differential Expression of Three *Chlamydia trachomatis* hsp60-Encoding Genes in Active vs. Persistent Infection," *Microb. Pathog.* 36:35-39, 2004.
Hilgenbrink and Low., "Folate Receptor-Mediated Drug Targeting: From Therapeutics to Diagnostics," *J. Pharm. Sci.* 94:2135-46, 2005.
Low et al., "Discovery and Development of Folic-Acid-Based Receptor Targeting for Imaging and Therapy of Cancer and Inflammatory Diseases," *Acc. Chem. Res.* 41:120-9, 2008.
Müller et al., "Effects of Antifolate Drugs on the Cellular Uptake of Radiofolates In Vitro and In Vivo," *J. Nucl. Med.* 47(12):2057-64, 2006.
Nakashima-Matsushita et al., "Selective Expression of Folate Receptor Beta and Its Possible Role in Methotrexate Transport in Synovial Macrophages From Patients With Rheumatoid Arthritis," *Arthritis. Rheum.* 42:1609-16, 1999.
Nanagara et al., "Alteration of *Chlamydia trachomatis* Biologic Behavior in Synovial Membranes: Suppression of Surface Antigen Production in Reactive Arthritis and Reiter's Syndrome," *Arthritis Rheum.* 38:1410-1417, 1995.
Panyam et al., "Rapid Endo-lysosomal Escape of Poly(DL-lactide-co-glycolide) Nanoparticles: Implications for Drug and Gene Deliver," *Faseb J.* 16:1217-26, 2002.
Panyam et al., "Efficiency of Dispatch and Infiltrator Cardiac Infusion Catheters In Arterial Localization of Nanoparticles in a Porcine Coronary Model of Restenosis," *J. Drug Target* 10:515-23, 2002.
Panyam et al., "Fluorescence and Electron Microscopy Probes for Cellular and Tissue Uptake of Poly(D,L-Lactide-Co-Glycolide) Nanoparticles," *Int. J. Pharm.* 262:1-11, 2003.
Panyam et al., "Solid-State Solubility Influences Encapsulation and Release of Hydrophobic Drugs From PLGNPLA Nanoparticles," *J. Pharm. Sci.* 93:1804-14, 2004.
Panyam and Labhasetwar, "Biodegradable Nanoparticles for Drug and Gene Delivery to Cells and Tissue," *Adv. Drug Deliv. Rev.* 55(3):329-47, 2003.
Panyam and Labhasetwar, "Dynamics of Endocytosis and Exocytosis of Poly(D,L-Lactide-Co-Glycolide) Nanoparticles in Vascular Smooth Muscle Cells," *Pharm. Res.* 20:212-20, 2003.
Panyam and Labhasetwar, "Sustained Cytoplasmic Delivery of Drugs With Intracellular Receptors Using Biodegradable Nanoparticles," *Mol. Pharm.* 1:77-84, 2004.
Prabha and Labhasetwar, "Critical Determinants in PLGA/PLA Nanoparticle-Mediated Gene Expression," *Pharm. Res.* 21:354-64, 2004.
Rank and Whittum-Hudson, "Animal Models for Ocular Infections," *Methods Enzymol.* 235:69-83, 1994.
Ross et al., "Differential Regulation of Folate Receptor Isoforms in Normal and Malignant Tissues In Vivo and In Established Cell Lines: Physiologic and Clinical Implications," *Cancer* 73:2432-2443, 1992.
Sabharanjak et al., "Folate Receptor Endocytosis and Trafficking," *Adv. Drug Deliv. Rev.* 56:1099-109, 2004.
Salazar and Ratnam, "The Folate Receptor: What Does It Promise in Tissue-Targeted Therapeutics?" *Cancer Metastasis Rev.* 26:141-52, 2007.
Schumacher et al., "Light and Electron Microscopic Studies on the Synovial Membrane in Reiter's Syndrome: Immunocytochemical Identification of Chlamydial Antigen in Patients With Early Disease," *Arthritis Rheum.* 31:937-46, 1988.
Shenoy et al., "Poly(Ethylene Oxide)-Modified Poly(Beta-Amino Ester) Nanoparticles As a pH-Sensitive System for Tumor-Targeted Delivery of Hydrophobic Drugs: Part 2. In Vivo Distribution and Tumor Localization Studies," *Pharm. Res.* 22:2107-14, 2005.
Sun et al., "Folic Acid-PEG Conjugated Superparamagnetic Nanoparticles for Targeted Cellular Uptake and Detection by MRI," *J. Biomed. Mater. Res. A.* 78:550-7, 2006.
Villareal et al., "Persistent *Chlamydiae* and Chronic Arthritis," *Arthritis Res.* 4(1):5-9, 2002.
Whittum-Hudson et al., "A Non-Invasive Murine Model of Chlamydia-Induced Reactive Arthritis," *Rev. Rhum. Engl. Ed.* 66(1, Supp.):50S-55S; discussion 56S, 1999.
Whittum-Hudson et al., "A Role for T Lymphocytes in Preventing Experimental Herpes Simplex Virus Type 1-Induced Retinitis," *Invest. Ophthalmol. Vis. Sci.* 26:1524-32, 1985.
Whittum-Hudson et al., "Murine Model of Ocular Infection by a Human Biovar of *Chlamydia trachomatis*," *Invest. Ophthalmol. Vis. Sci.* 36:1976-87, 1995.
Whittum-Hudson et al., "Oral Immunization With an Anti-Idiotypic Antibody to the Exoglycolipid Antigen Protects Against Experimental *Chlamydia trachomatis* Infection," *Nat. Med.* 2(10):1116-1121, 1996.
Whittum-Hudson et al., "Protection Against Murine Genital Infection by the Anti-Idiotypic Antibody (mAb2) Mimic of Chlamydial GLX: TH1-Dependent Immunity," *Proc. Fourth Eur. Chlamydia Research Meeting* 4:429, 2000.
Whittum-Hudson et al., "The Anti-Idiotypic Antibody to Chlamydial Glycolipid Exoantigen (GLXA) Protects Mice Against Genital Infection With a Human Biovar of *Chlamydia trachomatis*," *Vaccine* 19:4061-71, 2001.

\* cited by examiner

NANOPARTICLES FOR IMAGING AND TREATING CHLAMYDIAL INFECTION

CROSS-REFERENCE TO RELATED APPLICATION

This application is a 371 national phase of International Application No. PCT/US2008/070901 filed on Jul. 23, 2008, which is a non-provisional of U.S. Provisional Application No. 60/951,643 filed on Jul. 24, 2007, which applications are incorporated by reference in their entirety herein.

STATEMENT REGARDING FEDERALLY SPONSORED RESEARCH OR DEVELOPMENT

This invention was made with government support under grants AR 42541, AI 44493 and AR 48331 awarded by the National Institutes of Health. The government has certain rights in the invention. Support was also provided by the Wilson Foundation and Nanotechnology Enhancement funding from OVPR.

TECHNICAL FIELD

The present invention is directed to compositions of nanoparticles and targeting moieties for imaging and treating Chlamydial infection.

BACKGROUND OF THE INVENTION

All chlamydial species are obligate intracellular bacterial parasites of eukaryotic cells, and all are pathogenic to their various hosts. In addition to their known etiologic roles in elicitation of various acute diseases, the human pathogens *C. trachomatis* (CT) and *C. pneumoniae* (CP) have been shown to cause, or are strongly associated with, diverse chronic clinical entities. Such conditions are often caused by persistent infection.

Many studies indicate, however, that existing antimicrobial drugs are ineffective against such persistent chlamydial infections, and neither *C. trachomatis* nor *C. pneumoniae* requires an animal reservoir for maintenance. Because persistent chlamydial infections are highly prevalent and can have severe chronic disease sequelae, treatments to eradicate such persistent infections are urgently needed.

BRIEF SUMMARY OF THE INVENTION

A method of treating a *Chlamydia* bacterial infection in a patient in need of such treatment is provided, comprising administering to the patient a therapeutically effective amount of nanoparticles comprising at least one antibiotic agent, wherein the antibiotic agent is effective against *Chlamydia*. The antibiotic may be selected from the group consisting of azithromycin, amoxicillin, rifampicin, erythromycin, erythromycin ethylsuccinate, ofloxacin, levofloxacin doxycycline, and tetracycline, and the nanoparticles comprise folic acid, such as in a form conjugated to the nanoparticle surface. The *Chlamydia* may be selected from the group consisting of *C. trachomatis* and *C. pneumoniae* and other species such as *C psittaci, C pecorum, C caviae* or *C suis*.

Also provided is a composition comprising nanoparticles conjugated with folic acid, wherein the particles comprise a first antibiotic in a form and in a dosage suitable for treatment of a *Chlamydia* infection. The nanoparticles conjugated with folic acid or other targeting moieties may further comprise one or more other antibiotic(s) active against *Chlamydia*. The first antibiotic may be selected from the group consisting of azithromycin, amoxicillin, rifampicin, erythromycin, erythromycin ethylsuccinate, ofloxacin, levofloxacin doxycycline, and tetracycline. The one or more other antibiotics may be selected from the group consisting of azithromycin, amoxicillin, rifampicin, erythromycin, erythromycin ethylsuccinate, ofloxacin, levofloxacin doxycycline, and tetracycline, wherein the one or more other antibiotics is different from the first antibiotic.

Further provided is a method for inhibiting the growth of *C. pneumoniae* or *C. trachomatis* comprising contacting *C. pneumoniae* or *C. trachomatis*, or a cell infected by *C. pneumoniae* or *C. trachomatis*, with a composition comprising folic acid-conjugated nanoparticles and one or more antibiotics. The antibiotics may be selected from the group consisting of azithromycin, amoxicillin, rifampicin, erythromycin, erythromycin ethylsuccinate, ofloxacin, levofloxacin doxycycline, and tetracycline, or newer generations of one or more of these antibiotics.

Also provided is a method of imaging *Chlamydia* infection in a mammal, comprising the steps of administering to the mammal a composition comprising nanoparticles comprising folic acid and at least one imaging agent, and detecting the nanoparticles in the mammal, wherein the particles target folic acid receptor-expressing cells infected with *Chlamydia*. The nanoparticles may be fluorescently labeled.

Also provided is a composition for imaging *Chlamydia* infection in a cell, comprising nanoparticles conjugated with folic acid, wherein the nanoparticles further comprise at least one detectably labeled moiety, such as a fluorescent label.

BRIEF DESCRIPTION OF THE FIGURES

Exemplary embodiments are illustrated in referenced figures. It is intended that the embodiments and figures disclosed herein are to be considered illustrative rather than restrictive.

FIG. 4A shows 72 hours post-infection, and FIG. 4B shows 48 hours post-infection. FIG. 4C shows two Z cuts of the same field.

FIG. 20 shows free and nanoparticle-encapsulated antibiotics added at either t0 (time of infection) or after 24 hr of infection (t24), and included for controls blank nanoparticles.

Figure 1:
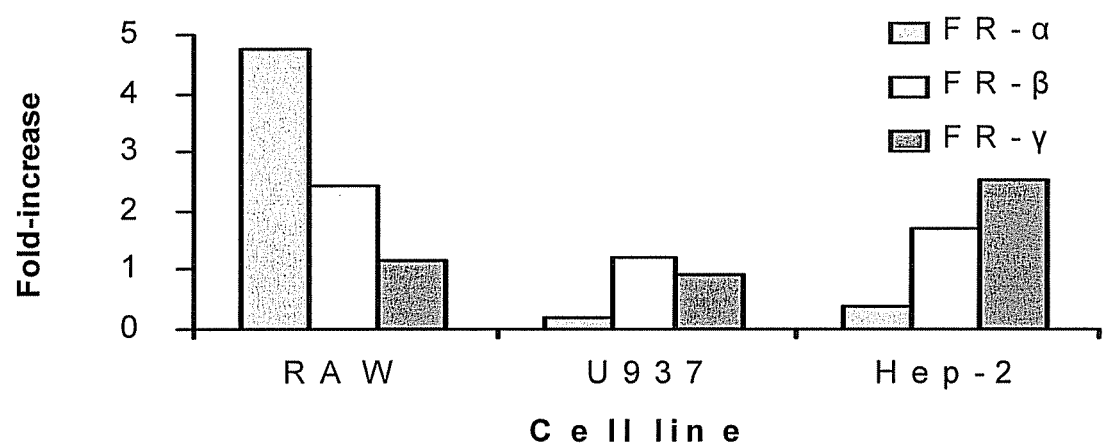
FIG. 1 shows RT-PCR analysis of relative transcript levels encoding the three folic acid receptor (FR) subtypes in chlamydia-infected and uninfected cells. Results are presented as fold-increase in receptor expression in infected cells compared to uninfected cells for each subtype.

N-acetyl cysteine to maintain sink conditions and stability, respectively. Released drug was quantitated by HPLC. Data are expressed as mean±S.D.

DESCRIPTION OF THE INVENTION

The urgent need for improved methods and compositions for localizing (imaging) and treating *Chlamydia* infection and its serious sequelae, including arthritis, blindness, COPD, and many others, is addressed herein using nanoparticles conjugated with folic acid, wherein the nanoparticles target *Chlamydia*-infected cells. The need is due in part to the persistence of *Chlamydia* in the body and the previous inability to specifically locate and treat such persistent infections. Both *C. trachomatis* and *C. pneumoniae* can disseminate widely from their sites of primary infection and cause significant long-term disease consequences. For the most part, those consequences result from a powerful immunopathogenic response to the organisms, as well as from the terminal host cell lysis/scarring at the end of the developmental cycle.

As with all chlamydiae, *C. trachomatis* and *C. pneumoniae* undergo an unusual biphasic developmental cycle. The cycle is initiated when elementary bodies (EB), the infectious extracellular form of the organism, attach to the target host cell. Once bound, EB are brought into a membrane-bound cytoplasmic inclusion within which they spend their intracellular tenure. In the inclusion EB develop into reticulate bodies (RB), the growth form. Each RB undergoes seven or eight rounds of cell division, after which most dedifferentiate back to EB. Newly-formed EB are released by host cell lysis or exocytosis (Hatch, T. P., 1999, In: *Chlamydia—Intracellular Biology, Pathogenesis, and Immunity*, Stephens, R. S., Ed. ASM Press, Washington D.C., pp. 29-67).

Many studies have demonstrated that both *C. trachomatis* and *C. pneumoniae* often disseminate widely from their sites of primary infection; when they do so, these organisms can take up long-term residence at distant anatomic locations (Moazed T. C., et al., 1998, *J. Infect. Dis.* 177:1322-1325; Villareal C., et al., 2002, *Arthritis Res.* 4:5-9). At sites of their disseminated residence, both organisms enter an unusual biological state referred to as 'persistence' (Villareal C., et al., 2002, *Arthritis Res.* 4:5-9; Hogan, R. J., et al., 2004, *Infect. Immun.* 72:1843-1855). In this state, a block in gene expression obviates the full completion of the normal developmental cycle, and the organisms display several unusual morphological, transcriptional and other properties (Byrne, G. I., et al., 2001, *Infect. Immun.* 69:5423-5429; Gérard, N. C., et al., 2001, *Mol. Microbiol.* 41:731-741). The means by which persistently infecting chlamydiae engender pathology is not well understood, but it is clear that they can elicit a powerful immunopathogenic response that can contribute to chronic diseases discussed herein.

Although trachoma largely disappeared in developed nations during the twentieth century, mainly because of improved public sanitation and availability of clean water, trachoma remains a significant disease in rural regions of many parts of the world, including the Middle East, Africa, southeast Asia, and the Indian subcontinent.

*Chlamydia psittaci* (also referred to as *Chlamydophila psittaci*) is a bacterium that can be transmitted from birds, such as pet birds, to humans, causing psittacosis. Beginning with a flu-like set of symptoms, the disease may progress to severe pneumonia and other non-respiratory problems. Persons at risk of contracting the disease include veterinarians, zoo workers, and poultry industry employees, such as turkey handlers at risk for pneumonia and systemic disease. (Fenga, C. et al., 2007, *Ann Agric. Environ. Med.* 14:93-96.) Suitable treatments and preventive measures include administering compositions of the invention to birds and to humans.

In the developing world, trachoma is still the primary cause of treatable/preventable blindness (Mabey, D. C., et al., 2003. *Lancet*, 362, 223-229; West, S. K., 2004. *Prog. Ret. Eye Res.*, 23, 381-401). Estimates of the prevalence of the disease world-wide suggest that nearly six million individuals currently are blind from trachoma, and perhaps twice that number are at significant risk for blindness (West, S. K., 2004. *Prog. Ret. Eye Res.*, 23, 381-401); as many as 150 million people world-wide are affected in some way by the disease (Kumaresan, J. A., et al., 2003. *Am. J. Trop. Med. Hyg.*, 69 (5 suppl.), 24-28). One estimate of the overall economic impact of trachoma gives a figure of $2.9 billion annual loss overall in productivity due to this disease (Kumaresan, J. A., et al, 2003. *Am. J. Trop. Med. Hyg.*, 69 (5 suppl.), 24-28). Although now confined primarily to the developing world, trachoma remains a disease of major importance, and it currently is a focus of intensive eradication efforts.

*C. pneumoniae* is responsible for a large proportion of cases of community-acquired pneumonia (Grayston, J. T., et al., 1992. Annu. Rev. Med., 43, 317-323). The incidence of seroconversion is low in children, but rises steeply after childhood. In the US, about 50% of 20 year-olds show evidence of prior infection (CDC website); by the seventh decade, seropositivity rates approach 80-90% (Leinonen, M., et al., 1993. Eur. Heart J., 14 (suppl.K), 57-61).

Importantly, *C. pneumoniae* has been associated with several more severe pulmonary diseases, including sarcoidosis, chronic obstructive pulmonary disease (COPD), arthritis, late-onset Alzheimer's disease, multiple sclerosis, giant cell arteritis, and others (for example, Balin, B. J., et al., 1998; Sriram, S., et al., 1999 Ann. Neurol., 46, 6-14; Swanborg, R. H., et al., 2003. J. Neuroimmunol., 136, 1-8). Given the high levels of adult seroposivity to *C. pneumoniae* observed in all studies, the costs associated with the disease must be substantial.

Cardiovascular disease is the leading cause of death in essentially all developed nations. In the late 1980's, a group in Finland published a landmark study indicating an association between *C. pneumoniae* infection and heart disease (Saikku, P., et al., 1988. Lancet, 2, 983-986). This association is now reasonably well-accepted in the medical and scientific communities, and it is particularly focused on atherosclerosis, a critical contributing factor to cardiovascular disease (reviewed in Belland, R. J., et al., 2004. Cell. Microbiol., 6, 117-127; and Campbell, L. A., et al., 2004. Nat. Rev. Microbiol., 2, 23-32). The organism has been identified in atherosclerotic plaques by several standard screening techniques and by many independent laboratories (Ciervo, A., et al., 2003. Mol. Cell. Probes., 17, 107-111). A biochemical mechanism by which *C. pneumoniae* may contribute to plaque formation has been defined (Kalayoglu, M. V., et al., Byrne G. I., 1998b. Infect. Immun., 66, 5067-5072).

As a leading cause of death and incapacity in developed nations, cardiovascular disease imposes an enormous burden on the health care systems of all those countries. For just one example, a recent study from the Netherlands indicated that the cost of treatment for a single affected individual can be a high as € 380000 (Groot, et al., 2004. Health Econ., 13, 850-872). This does not include the costs of productivity losses attributable to affected individuals. Thus, it is feasible that *C. pneumoniae* infection alone may be responsible for an exceptionally large proportion of health care costs in developed nations.

Sexually-transmitted infections are among the most common diseases world-wide, and *C. trachomatis* is almost certainly the most common sexually-transmitted bacterial infection among them. One report estimated that in 1995, 89 million people between 15 and 45 years of age globally had a chlamydial infection of the urogenital tract (Gerbase, A. C., et al., 1998. *Sex. Transm. Infect.,* 74 (suppl. 1), S12-S16). In the United States, genital infections by *C. trachomatis* must be reported to the Centers for Disease Control (CDC) by each of the fifty states and the District of Columbia. In 2003, almost 900,000 new cases of *C. trachomatis* infection were reported by the states and the District together (Centers for Disease Control and Prevention, 2004). Estimates from various sources range as high as 4 million active cases of genital *C. trachomatis* at any one time in the U.S. Genital infections by *C. trachomatis* are of particular concern for women due to the potential long-term reproductive sequelae that they can engender.

Estimates of the prevalence of genital chlamydial infection in Europe appear to be equivalent, or even somewhat higher, than those for the U.S. For example, a recent study showed a prevalence of 5.9% for genital *C. trachomatis* infection among men 17-35 years of age in Ireland (Powell, J., et al., 2004. *Sex. Transm. Infect.,* 80, 349-353); a similar prevalence was identified among young women screened in three cities in Scotland. In England, where a National *Chlamydia* Screen Program was initiated in 2002 for men and women under 25 years of age, the first year's data indicated a 10.1% prevalence among women tested and a 13.3% prevalence among men (LaMontagne, D. S., et al., 2004. *Sex. Transm. Infect.,* 80, 335-341). In Eastern Europe, estimates of genital chlamydial infection among young women give values of 4.5% or higher (Masata, J., et al., 2004. Deák, J. (Ed.) *Proceedings of the Fifth Meeting of the European Society for Chlamydia Research*, Pauker Nyomdaipari Kft, Budapest, Hungary).

The standard treatment for active primary urogenital infection with *C. trachomatis* is a course of doxycycline or erythromycin or a single dose of azithromycin, and these have proved to be effective in eradicating organisms (Tobin, J. M., et al., 2004, *Intl J. STD AIDS* 15:737-739); treatment with azithromycin has also proved effective for active pulmonary *C. pneumoniae* infection. Unlike treatment of active chlamydial infections, antimicrobial therapy of persistent infections by either organism is problematic. For example, either species infecting joint tissues in arthritis patients respond poorly or not at all to standard treatment with antibiotic because they reside in those tissues in the persistent state (Whittum-Hudson J. A., et al., 2006, In: *Chlamydia—Genomics and Pathogenesis*, Bavoil P., Wyrick P., Eds., pp. 475-504 (Horizon Bioscience Press (Norfolk, U. K.)).

The most important sequelae to genital *C. trachomatis* infection include PID, salpingitis, occlusion of the fallopian tubules, and other fertility-abolishing or -diminishing problems in women; epididymitis can follow genital infection in men. Recent estimates indicate that about 8% of women with lower genital tract infection with *C. trachomatis* progress to PID; this number appears to account for half of all PID cases (Honey, E., et al., 2002. *Intl. J. Gynecol. Obstet.,* 78, 257-261).

As importantly, nearly two thirds of women with infertility due to occluded fallopian tubes show antibodies against this organism; *C. trachomatis* may be the causative agent in up to 40% of ectopic pregnancies (Honey, E., et al., 2002. *Intl. J. Gynecol, Obstet.,* 78, 257-261). Other reports indicate that genital *C. trachomatis* is the most common cause of acute salpingitis, and that perhaps 25% of women with the acute disease become infertile (Guaschino, S., et al., 2000. *Ann. N. Y. Acad. Sci.,* 900, 293-300). The incidence of new cases of PID and other reproductive problems due to genital chlamydial infection is high among urban young women in the U.S. (Kelly, A. M. et al., 2004. *J. Pediatr. Adolesc. Gynecol.,* 17, 383-388) and in Europe (Grio, R., et al., 2004. *Minerva Ginecol.,* 56, 141-147).

Genital infection with *C. trachomatis* also can elicit a painful inflammatory arthritis in both men and women, similar to the arthritis that can follow *C. pneumoniae* infection (Whittum-Hudson, J. A., et al. 2006. Pathogenesis of *Chlamydia*-associated arthritis, in Bavoil, P., Wyrick, P. (Eds.), (supra); Whittum-Hudson, J. A., et al., 2005. *Chlamydia pneumoniae* and inflammatory arthritis, in Yamamoto, Y., Friedman, H., Bendinelli, M. (Eds.), *Chlamydia pneumoniae Infection and Diseases*. NY, Kluwer/Academic Press, 227-238). The prevalence of acute *C. trachomatis-induced* arthritis has not been firmly established, but conservative estimates from the United States and elsewhere suggest it to be in the range of 5-10% of individuals with a documented prior genital infection with the organism (Rich, E., et al. 1996. *Arthritis Rheum.,* 39, 1172-1177).

Nanoparticles provide a powerful new means for finding and eradicating the sites of persistent *Chlamydia* infection that can lead to the broad range of chronic health issues discussed above. The term "nanoparticle" has been used to refer to nanometer-size devices consisting of a matrix of dense polymeric network (also known as nanospheres) and those formed by a thin polymeric envelope surrounding a drug-filled cavity (nanocapsules) (Garcia-Garcia E, (2005). *Int J Pharm* 298:274-92). Nanoparticles can penetrate into small capillaries, allowing enhanced accumulation of the encapsulated drug at target sites (Calvo P, et al. (2001). *Pharm. Res.* 18:1157-66). Nanoparticles can passively target tumor tissue through enhanced permeation and retention effect (Monsky W L, et al. (1999). *Cancer. Res.* 59:4129-35; Stroh M, et al. (2005). *Nat. Med.* 11:678-82).

Nanoparticles can be delivered to distant target sites either by localized catheter-based infusion (Panyam J, (2002). *J. Drug Target.* 10:515-523) or by attaching a ligand to nanoparticle surface that has affinity for a specific tissue (Shenoy, D., (2005). *Pharm Res* 22:2107-14). Because of sustained release properties, nanoparticles can prolong the availability of the encapsulated drug at the target site, resulting in greater and sustained therapeutic effect (Panyam J and Labhasetwar V (2003). *Adv Drug Deliv Rev* 55:329-47).

"PEGylation" refers to the decoration of particle surface by covalently grafting or adsorbing of PEG chains. The purpose of PEG chains is to create a barrier to the adhesion of opsonins present in the blood, so that delivery systems can remain longer in circulation, invisible to phagocytic cells (Kommareddy S, (2005). *Technol Cancer Res Treat* 4:615-26).

This disclosure is based in part on the important new discovery herein that *Chlamydia*-infected cells overexpress folic acid receptors. Thus, folic acid conjugates can be used to specifically target *Chlamydia*-infected cells. Although the reduced folate carrier is present in virtually all cells, folate-conjugates are not substrates and are taken up only by cells expressing functional folate receptors (Hilgenbrink A R et al., (2005a). *J. Pharm. Sci.* 94:2135-46). Folic acid conjugation allows endocytic uptake of the conjugated carrier via the folate receptor, resulting in higher cellular uptake of an encapsulated drug or targeting moiety. The high affinity of folic acid to its receptor (binding constant ~1 nm) and folate's small size make it ideal for specific cell targeting. Furthermore, the ability of folic acid to bind its receptor is not altered by covalent conjugation to delivery systems (Lee, R. J. et al., (1994). *J. Biol. Chem.* 269:3198).

Effective treatments for active urogenital and ocular infections by *C. trachomatis* are available in the form of various antimicrobials. The standard treatment for urogenital infection with *C. trachomatis* is a course of doxycycline or erythromycin, or a single dose of azithromycin, and these have proved to be effective in eradicating actively-growing organisms (Tobin, J. M., 2004, *Intl. J. STD AIDS*, 15, 737-739 2004). Treatment with azithromycin has also proved reasonably effective for active pulmonary *C. pneumoniae* infection. Many studies indicate, however, that existing antimicrobial drugs are ineffective against persistent chlamydial infections, and neither *C. trachomatis* nor *C. pneumoniae* requires an animal reservoir for maintenance. Thus, the distribution of active and persistent chlamydial infections in any given human population must be assessed before large-scale treatment programs can be designed appropriately.

Unlike treatment of active *C. trachomatis* or *C. pneumoniae* infections, antimicrobial treatment of persistent infections by either organism await improved diagnostic and therapeutic agents and methods, which are now provided by the present invention. For example, *Chlamydia* of either species infecting joint tissues in arthritis patients respond poorly or not at all to standard treatment with a single antibiotic because they reside in those tissues in the persistent, rather than the actively-growing state (Whittum-Hudson, J. A., et al., 2006. Pathogenesis of *Chlamydia*-associated arthritis, in Bavoil, P. Wyrick, P. (Eds.), *Chlamydia—Genomics and Pathogenesis*, Horizon Bioscience Press, Norfolk, England, 2006, Chapter 21.); (Whittum-Hudson, J. A., et al., 2005. *Chlamydia pneumoniae* and inflammatory arthritis, in Yamamoto, Y., Friedman, H., Bendinelli, M. (Eds.), *Chlamydia pneumoniae Infection and Diseases*, NY, Kluwer/Academic Press, 227-238). In the case of atherosclerosis, it is not clear whether *C. pneumoniae* resides in vessel tissues in the persistent or actively-growing form or some mixture of each, but large-scale antibiotic trials have failed to show improvement in patients with aortic or other plaques (Grayston, J. T., et al., 2005, N. Engl. J. Med., 352, 1637-1645). Using the imaging compositions and methods disclosed herein, the location of *C. pneumoniae* can now be investigated and the resulting atherosclerosis treated.

As shown in FIG. 1, folic acid receptor subtypes were expressed at a higher level in *Chlamydia*-infected human or mouse cells. By showing that *Chlamydia*-infected cells overexpress folic acid receptors, this disclosure provides a new mechanism for finding, imaging, and treating previously unidentifiable persistent infections.

Figure 2:
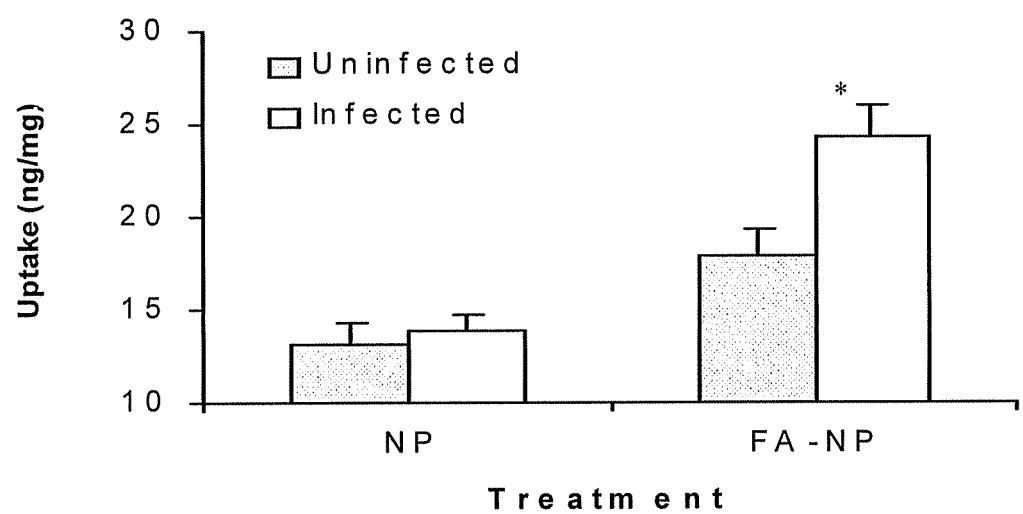
FIG. 2 shows quantitative analysis of nanoparticle uptake in chlamydia-infected and uninfected cells. Cells were treated with nanoparticles with or without folic acid (FANP, NP, respectively) and nanoparticle uptake quantitated by HPLC. Uptake normalized to total cell protein. *$P<0.05$ FIG. 3, panels A and B show images demonstrating the homing of labeled nanoparticles to infected host cells, using the RTM-3 microscope. Panel A, visible light image of a 24 hr-infected HEp-2 cell pulsed with particle. Panel B, the same cells viewed under epifluorescence. The inclusion is indicated by arrows.
Figure 3:
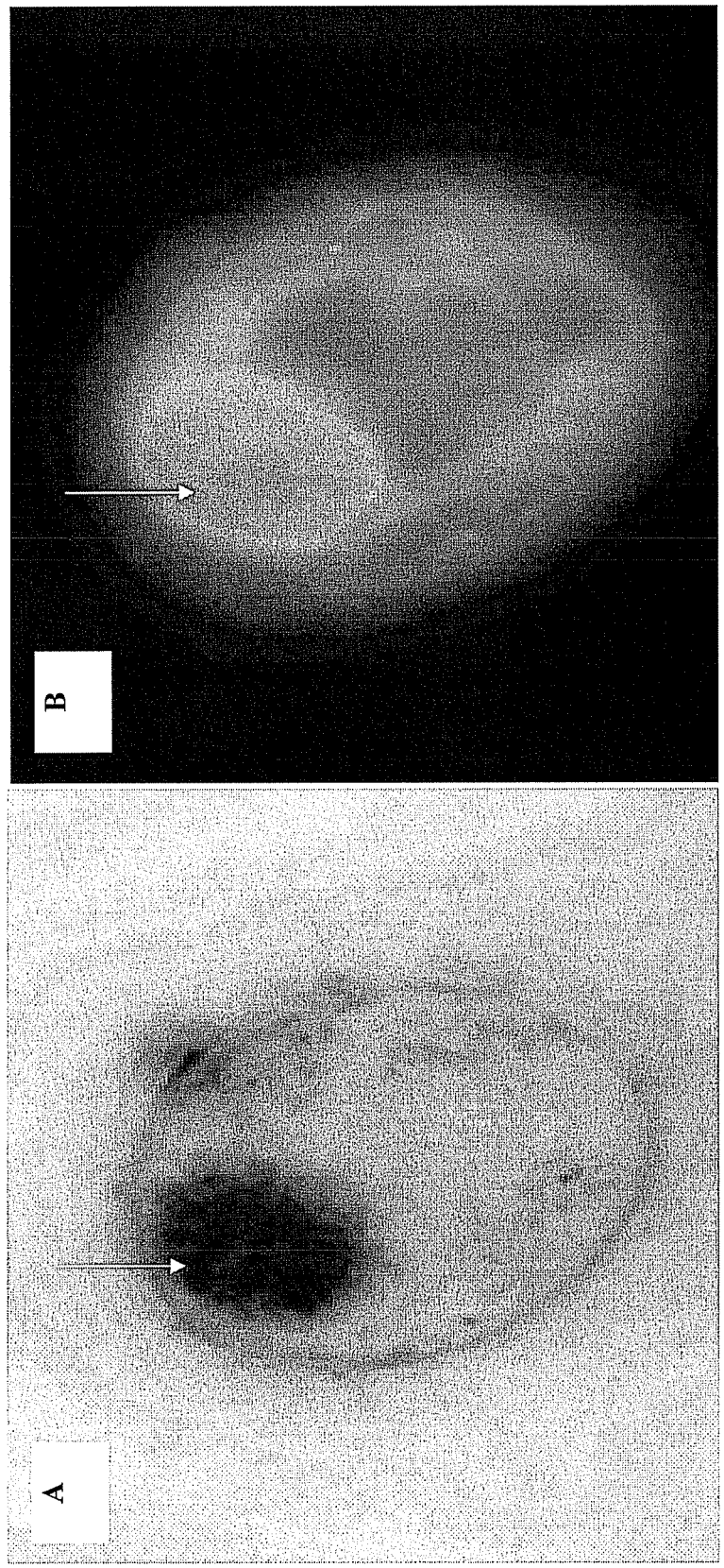

FIG. 2 shows that nanoparticles derivatized with folic acid accumulated more in *Chlamydia*-infected HEp-2 cells than in non-infected cells. Nanoparticles also targeted inclusions within *Chlamydia*-infected cells. As described in detail in the Examples, and as shown in FIG. 3, HEp-2 cells infected with *Chlamydia* were pulsed with labeled nanoparticles and examined under epifluorescence using a RTM-3 microscope. This discovery was then used to deliver plasmid DNA into Chlamydial inclusions (FIG. 3). HEp-2 cells were infected with *Chlamydia* (CT) and then pulsed with nanoparticles containing plasmid DNA (FIG. 4). Delivery to inclusions was imaged using separate fluorescent markers on the DNA and the nanoparticles. The results are discussed in more detail in the Examples.

The relevance of these in vitro studies to imaging and treating true *Chlamydia* infection was demonstrated in mouse models of infection. As described in the Examples, folic acid-derivatized nanoparticles targeted Chlamydial infected sites in mice at day 8 and day 11 of infection. Infection was undetectable using nanoparticles without folic acid. Sites of infection imaged were the genital tract (ex vivo) and joints (knees and paws/ankles); spleen, kidney and the liver were imaged ex vivo as well.

Nanoparticles formulated using a FDA-approved, biodegradable polymer PLGA were used in the disclosed studies. Applicants' previous studies demonstrated that PLGA nanoparticles are non-toxic and biocompatible (J. Panyam, et al. *Int J Pharm* 262: 1-11 (2003), and are suitable for in vivo drug delivery (J. Panyam, et al. *J Drug Target* 10: 515-23 (2002). Applicants previously showed that nanoparticles can efficiently encapsulate and sustain the release of hydrophobic drugs like dexamethasone (J. Panyam, et al. *J Pharm Sci* 93: 1804-14 (2004) and paclitaxel, and nucleic acids (S. Prabha, et al. *Int J Pharm* 244: 105-15 (2002). An important advantage of PLGA nanoparticles is that the rate of drug/nucleic acid release from nanoparticles, and therefore, the therapeutic efficacy, can be controlled by varying the polymer properties such as molecular weight, lactide-glycolide ratio and end-group chemistry (J. Panyam, et al. *Mol Pharm* 1:77-84 (2004); (S. Prabha, et al. *Pharm Res* 21: 354-64 (2004).

In summary, the data disclosed herein demonstrate that nanoparticles can be targeted to cells infected with *Chlamydia* using folic acid. The invention provides for new methods of detection and treatment using, for example, antibiotics, small molecules, antibodies, and polynucleotides.

Suitable antibiotics include those previously demonstrated to be effective against one or more form of *Chlamydia* infection, such as azithromycin, amoxicillin, rifampicin, erythromycin, erythromycin ethylsuccinate, ofloxacin, levofloxacin doxycycline, and tetracycline. A polynucleotide such as DNA can be incorporated in the nanoparticles to affect the life cycle of the organism, for example as an antisense treatment. Although it has not been developed in the present context, all chlamydial species are difficult to work with in in vitro systems because no genetic modification system is currently available for these organisms. That is, while the genomes of many, perhaps most, bacterial pathogens can be manipulated by various means so as to assess the function of particular genes or sets of genes of interest, no such system currently exists for chlamydiae. Development of a system for genetic manipulation of CT or CP or both would allow elucidation of the function(s) of the many genes in the genome of each organism for which no function is known. Such elucidation would almost certainly lead to additional means to eradicate active human chlamydial infections, and it would probably provide new strategies for obviation of persistent infections by these organisms. The general means of genetic manipulation involves delivering oligonucleotides or other constructs to the living organism of interest, the result of which is most often intended to be attenuation of expression of the gene(s) of interest. In the present context, we will load the nanoparticles with oligonucleotides or other constructs to affect expression of chlamydial genes that we suspect will disallow completion of the intracellular developmental cycle and/or obviate production of chlamydial molecules involved intimately in the pathogenesis process.

Guidance for doses and dosing regimens are well-known to the practitioner, and will be adapted for use in the context of the nanoparticle administration methods herein. For example, azithromycin can be given at a dose of 1 g orally as a single dose. Doxycycline can be given 100 mg orally twice a day for 7 days. Erythromycin can be given 500 mg orally four times a day for 7 days; erythromycin ethylsuccinate can be given 800 mg orally four times a day for 7 days; oflaxicin can be given 300 mg orally twice a day for 7 days; and levofloxacin can be given 500 mg orally for 7 days.

Several imaging modalities can be used to image chlamydial infection. As described in the Examples, fluorescently-labeled folate conjugates can be used for optical imaging of chlamydial infections. Radiolabeled folate conjugates can be used in conjunction with CT scanning to image chlamydial infection (Muller C, et al, J Nucl Med. 2006 December; 47(12):2057-64). Folic acid can also be conjugated to agents like gadolinium or superparamagnetic nanoparticles for magnetic resonance imaging (MRI) of chlamydial infections (Sun C et al, J Biomed Mater Res A. 2006 Sep. 1; 78(3):550-7).

Human infections by the intracellular bacterial pathogens *Chlamydia trachomatis* and *C pneumoniae* present an enormous health care problem. Infections by these pathogens have been associated with engendering and/or exacerbating several chronic diseases, and some of these Chlamydial infections have proved to be refractory to antibiotic therapy. The lack of therapeutic efficacy results from the attenuated metabolic rate of infecting chlamydiae under some circumstances, in combination with the modest intracellular concentrations achievable by normal delivery of such drugs to the inclusions within which chlamydiae reside in the host cell cytoplasm.

The major therapeutic goal of the disclosure herein provides a means by which antibiotics or other therapeutic agents can be delivered in a targeted manner to the intracellular Chlamydial inclusion at effective concentrations, without toxicity to the host cell or infected tissue. Chlamydial infection elicits increased expression of host cell folic acid receptors (FAR), and that folic acid-conjugated nanoparticles provide a novel and highly effective means of intracellular delivery of therapeutic agents to *Chlamydia*-infected cells. According to the present disclosure, host cells infected with either *C trachomatis* or *C pneumoniae* can be cleared of actively- or persistently-infecting organisms via nanoparticle-mediated targeted delivery of effective concentrations of antibiotics known to work against active Chlamydial infections.

Human infections by the intracellular bacterial pathogens *Chlamydia trachomatis* and *C pneumoniae* present an enormous burden to the US health care system. The former is the most prevalent sexually transmitted bacterium in developed nations. In the US, recent data indicate that there are an estimated 2-4 million new STD cases annually caused by *C trachomatis*. *C pneumoniae* is a respiratory pathogen responsible for a significant proportion of community-acquired pneumonia.

Both *C trachomatis* and *C pneumoniae* can and often do disseminate widely from their sites of primary infection. At anatomic locations distant from those primary infection sites, both organisms may enter an unusual biologic state designated "persistence", and it is in this form that both have been strongly associated with engendering chronic diseases, including inflammatory arthritis, tubal occlusion leading to ectopic pregnancy, and cervical cancer (*C trachomatis*); *C pneumoniae* has been compellingly associated with atherosclerosis, inflammatory arthritis, and temporal arteritis, among several other diseases.

Primary infections with *C trachomatis* and *C pneumoniae* can usually be treated effectively with antibiotics. However, for reasons that remain to be fully elucidated, persistent infections by both organisms have proved to be refractory to such treatments. In large part, the lack of therapeutic efficacy results from the attenuated metabolic rate of persistently infecting Chlamydiae in combination with the modest intracellular concentrations achievable by normal delivery of such drugs to the inclusions within which Chlamydiae reside in the host cell cytoplasm. The major therapeutic goal, and the long-term goal of the disclosure herein, is to provide means by which antibiotics or other therapeutic agents can be delivered in a targeted manner to the intracellular Chlamydial inclusion at effective concentrations, with minimal toxicity to the host cell or infected tissue.

Chlamydial infection elicits increased expression of host cell folic acid receptors (FAR), and folic acid-conjugated nanoparticles provide a novel and highly effective means of targeted intracellular delivery of therapeutic agents to *Chlamydia*-infected cells. Without being limited to a specific mechanism, the present disclosure is based in the finding that host cells persistently infected with either *C trachomatis* can be cleared of persistently-infecting organisms via nanoparticle-mediated targeted delivery of effective concentrations of antibiotics known to work against active Chlamydial infections. Nanoparticle-facilitated delivery requires reduced amounts of therapeutic materials for both acute and persistent infections, thus engendering significant health care cost reductions.

All Chlamydial species are obligate intracellular bacterial parasites of eukaryotic cells, and all are pathogenic to their various hosts [1]. In addition to their known etiologic roles in elicitation of various acute diseases, the human pathogens *C trachomatis* and *C pneumoniae* have been shown to cause, or are strongly associated with, diverse chronic clinical entities. Trachoma is caused by repeated ocular infection with *C trachomatis*.

As the leading cause of infectious blindness in humans [1,2], half a billion people suffer from trachoma, and up to one-fourth of those infected will become blind. Although trachoma has largely disappeared from North America and Europe, extraocular Chlamydial infections remain of great importance in the latter areas; ie, 2-4 million new Chlamydial sexually transmitted infections (STI) are reported each year in the US alone, with an annual cost exceeding $1 billion. Chlamydial genital tract infection is over 5 times more common than gonorrhea [3] and has been correlated with increased risk of HIV infection and other STI pathogens [4].

*C trachomatis* is the leading cause of tubal infertility and pelvic inflammatory disease, eg [5,6]. Chlamydial genital infection occurs in 5-15% of pregnant women, and 50% of their babies will develop inclusion conjunctivitis or respiratory infections [7], making *C trachomatis* the most common ocular pathogen in infants [8]. Genital infections also predispose to development of a significant proportion of reactive arthritis cases [9], in which viable, metabolically active organism is present in synovial tissue, primarily within monocyte/macrophages [10]. *C pneumoniae*, identified as a cause of community-acquired pneumonia in adults, also has been associated with atherogenesis [11, 12]; seroepidemiologic studies suggest that the majority of adults have been exposed to *C pneumoniae*.

Although controversial, *C pneumoniae* has been associated with other chronic inflammatory diseases, including late onset Alzheimer's disease [13, 14], and one or more forms of multiple sclerosis [15]. *C psittaci* infects avian species and can have major economic impact on poultry production, as well as placing poultry handlers at risk for transmission [16]; recent data implicates *C psittaci* as well as other Chlamydial species in temporomandibular joint disease ([17]). The application also provides a method to treat, cure or prevent *chlamydia*-associated reactive arthritis, as well as treating, curing or preventing disease at other sites where Chlamydiae disseminate and cause inflammation, including atheromas, sites in the lungs, and sites in the brain.

While cause-effect relationships have not been proven in several of these diseases, and several negative reports have been published, data confirming a presence of *C pneumoniae* in CSF from additional MS patients, and in brains of independent samples from AD brains have been presented at national/international meetings by respected researchers [14, 18]. Thus, the public health significance of Chlamydial infection is enormous, and a drug-targeting approach capable of selective delivery of antibiotics to the infected cells has industrial applicability.

As with all Chlamydiae, *C trachomatis* and *C pneumoniae* undergo an unusual biphasic developmental cycle. The cycle is initiated when elementary bodies (EB), the infectious extracellular form of the organism, attach to the target host cell. Once bound, EB are brought into a membrane-bound cytoplasmic inclusion within which they spend their intracellular tenure (stage 1). In the inclusion, EB develop into reticulate bodies (RB; stage 2), the growth form. Each RB undergoes 7-8 rounds of cell division (stage 3), after which most dedifferentiate back to EB. Newly-formed EB are released by host cell lysis or exocytosis ([20]).

Many studies have demonstrated that both *C trachomatis* and *C pneumoniae* often disseminate widely from their sites of primary infection; when they do so, these organisms can take up long-term residence at distant anatomic locations [21,22]. At sites of their disseminated residence, both organisms enter an unusual biological state referred to as 'persistence' [22,23] (stage 5). In this state, a block in gene expression obviates the full completion of the normal developmental cycle, and the organisms display several unusual morphological, transcriptional, and other properties (eg, [24,25]).

The means by which persistently infecting Chlamydiae engender pathology is not well understood, but it is clear that they can elicit a powerful immunopathogenic response that can contribute to genesis/exacerbation of the chronic diseases mentioned above. Various cell stresses can induce transition into the 'persistent' state in vitro and presumably in vivo: starvation, heat shock, penicillin G, interferon-γ (IFNγ), iron deprivation. Morphologically, persistent forms are distinct, aberrantly large RB (stage 5); transcriptionally, not all models of persistence are entirely consistent. A monocyte model of persistence has been described, which has features in common with persistence seen in human and murine reactive arthritis, eg. [25,26].

The inventors compared the transcript profiles of *C. pneumoniae* in the persistent state as elicited by IFNγ treatment, penicillin G treatment, and iron deprivation, all compared to the transcript profile of the same strain (CWL029) persistently infecting normal human monocytes. In these in vitro experiments, transcript profile was not entirely consistent among all these persistence models, nor was it fully consistent with that/those of *C. trachomatis* whose persistent state is elicited by parallel means. However, there are some features held in common for all models of persistence. For example, ftsK is always off, whereas ftsW is not. Thus, a number of molecular genetic and other details regarding 'persistent' Chlamydial infections remain to be defined.

A recent study in ReA patients has shown that combination antibiotic therapy may be more effective in vivo for acute and persistent synovial infection [28]; this is supported by in vitro data from several studies. Because of growing concerns about antibiotic resistance, improved combined therapies for Chlamydial infections would be highly desirable. A challenge to treatment of Chlamydial infections is the complex intracellular developmental cycle in which drugs and other therapeutics must cross several membranes, not simply the bacterial membrane. According to the present disclosure, the size and rapid entry of nanoparticles into infected cells enables encapsulated antibiotics to more efficiently/successfully reach the bacterial targets. Persistent Chlamydial infections are highly prevalent and can have severe chronic disease (inflammatory) sequelae. Improved treatments to eradicate such persistent infections are urgently needed and have industrial applicability.

Folate receptors are overexpressed following infection. Human and murine cells encode several receptor isoforms for folic acid, of which α, β, and γ are the most prominent [29]. These receptors are differentially expressed as a function of cell type, growth conditions, and the general health of the cell [30]. Studies by others suggest that folic acid and folate conjugates have equal affinity for the different isoforms [31]. Recent studies indicate that folic acid receptors (FAR) are overexpressed on activated macrophages in the synovium of arthritic joints [32]. Chlamydial infection causes activation of monocytes and macrophages and their localization to the joint (and other infected tissues). Studies by the inventors showed an increase in the mRNA encoding FAR in cultured human macrophages and human epithelial cells 24 hrs post-infection with *C trachomatis*. Increased expression of FAR on *Chlamydia*-infected cells indicates that such cells can be targeted using folic acid as targeting ligand.

Nanoparticles for Targeted Antibiotic Delivery.

Nanoparticles refer to nanometer-size devices with a matrix core of dense polymeric network, with antimicrobials, vaccines, or other therapeutic molecules encapsulated in the polymer core. The inventors' previous research has demonstrated that PLGA nanoparticles are non-toxic and biocompatible [38], and they are suitable for in vivo drug delivery [39]. The inventors also have shown that nanoparticles can efficiently encapsulate and sustain the release of hydrophobic drugs such as dexamethasone [40] and paclitaxel and nucleic acids [41]. important advantage of PLGA nanoparticles is that the rate of drug release from nanoparticles, and therefore, the therapeutic efficacy, can be controlled by varying the polymer properties such as molecular weight, lactide-glycolide ratio and end-group chemistry [42,43].

PLGA nanoparticles are rapidly taken up into cells by endocytosis, resulting in higher cellular uptake of the entrapped drug compared to that following conventional drug treatment [44]. The therapeutic efficacy of nanoparticles is further enhanced by their ability to protect the drugs from degradation by lysosomal enzymes [45]. Nanoparticles, because of their colloidal nature and serum stability [44], can be easily dispersed in saline and injected intravenously. Because of their small size, such particles can penetrate small capillaries, allowing enhanced accumulation of encapsulated drug or other therapeutic molecule at target sites. Nanoparticles can be delivered to distant target sites by attaching a ligand such as folic acid to the particle surface which has affinity for a specific tissue. Nanoparticles can be employed to deliver either single or combination antibiotics to targeted sites, and they may be useful for specific delivery of vaccines or other therapeutic modalities. Folic acid-conjugated nanoparticles rapidly target *Chlamydia*-infected cells in both in vitro and in vivo systems of such infections.

Animal models of disseminated Chlamydial infection. Animal models have provided important information regarding Chlamydiae and the immune/inflammatory responses these bacteria induce in vivo, eg, [46-54]. These studies have added insights into pathogenic processes such as the association of repeated infection with increased clinical and histopathologic disease, and immunization studies testing several logical vaccine candidate antigens including MOMP and hsp60 [51, 55, 56]. Until recently, most mouse models have utilized the mouse pneumonitis strain (MoPn) of *C trachomatis* to study the pathogenesis and immune responses during pneumonia and genital infection Eg, [57-63]. Human biovars of *C trachomatis* have also been used to establish murine genital infection models [47, 48, 64-66]. While some features of each of the models have direct relevance to human disease, many differences between the diseases in models and human disease have been noted.

Few animal studies have investigated *Chlamydia*-associated reactive arthritis (ReA), a good disease model for studying persistent infections. In earlier studies, we observed that ocular infection of mouse conjunctivae (an ocular mucosal tissue) resulted in Chlamydial dissemination to synovium [67]. More recently, we have focused primarily on a genital infection model to induce murine ReA since this infection route is more representative of human *Chlamydia*-associated ReA. The latter model allowed us to document dissemination of *C trachomatis* to synovial tissues and associated knee pathology. An overview of the synovial inflammation induced in the co-PI's murine ocular and genital infection models has been published [54,67].

Chlamydial dissemination occurs in other animal models: *C pneumoniae* was shown by Moazed et al to disseminate to distant sites after intranasal challenge of mice, but synovium was not assayed [21]. Studies by Rank et al with a mouse pneumonitis strain of *C trachomatis* (MoPn)-induced genital infection resulted in an acute arthritis [68], but these studies preceded knowledge of persistent infection in ReA and availability of molecular screening to demonstrate presence of viable organism. The latter studies utilized either presensitization or intra-articular Chlamydial challenge, making it less physiologic than natural dissemination from genital infection. Rank and colleagues have also shown in guinea pigs dissemination of GPIC from genital tract to joint [69].

The inventors' model for *C trachomatis*-associated ReA offers distinct, demonstrated advantages for the proposed studies because of its noninvasive mode of disease generation and reproducible inflammation and infection. In addition, we show the feasibility of imaging nanoparticle localization in addition to targeting sites of Chlamydial infection with drug-loaded nanoparticles. Thus, means are used to monitor nanoparticle trafficking, success of drug delivery, and subsequent proof of cure by imaging, histology and molecular analyses, in addition to quantification of nanoparticles in tissues.

The data disclosed herein provide a new and unique combination of basic and applied science-oriented approaches to precise targeting of therapeutic agents to target *Chlamydia*-infected cells and tissues. Overexpression of folate receptors following Chlamydial infection and the use of folic acid conjugated delivery system to target (Chlamydia) infected cells have not been reported before. This approach can have a significant impact on treatment of several severe chronic diseases associated with persistent infection by *C trachomatis* and *C pneumoniae*. Targeted antibiotic delivery using nanoparticles is expected to reduce the amount of drug required, which would have a substantial impact on drug costs for Chlamydial infection treatment/cure. Additionally, all nine species comprising the Order Chlamydiales are pathogenic to their various hosts, and the seven animal pathogen species have enormous economic impact on domestic and other animals. Importantly, this approach to development of a targeting system for therapeutic agents can provide a model for development of congruent systems to eradicate other intracellular pathogens, including *Mycobacterium tuberculosis, Listeria monocytogenes*, and others. The constitution of nanoparticles can be designed for either rapid or long-term release of the encapsulated agent(s) [40]. The disclosure is applicable to developing systems providing sustained delivery of antimicrobial or other therapies to infected tissues, transformed cells, etc. Thus, the data are expected to have a significant impact on the field of infectious diseases.

The following examples are intended to illustrate but are not to be construed as limiting of the specification and claims in any way.

EXAMPLES

Example 1

*Chlamydia*-Infected Cells Overexpress Folic Acid Receptors

Mammalian cells encode multiple folic acid receptors, designated $\alpha$, $\beta$, and $\gamma$ (Ross, J. F. et al. (1992) Cancer 73:2432-2443). The present Example was performed to examine the expression of those receptors in *Chlamydia* infected cells. Nearly confluent monolayers of cycloheximide-treated cells were infected in vitro at MOI 5:1 with K serovar *C. trachomatis*. The cell lines employed in these experiments were RAW 264.7 and U937 (murine and human macrophage lines, respectively), and HEp-2 (human epithelial cell line).

At 24 hr post-infection, infected and uninfected control cultures were harvested, and RNA/cDNA was prepared for real time RT-PCR analysis to determine relative levels of mRNA encoding each of the three receptor subtypes in infected versus uninfected cells. As shown in FIG. 1, *C. trachomatis* infection resulted in increased expression of the $\beta$, and $\gamma$ receptors in human cells. The over-expressed isoform was dependent on the cell type. That is, a murine cell line showed the largest increase in the folic acid receptor alpha ($\alpha$) isoform, unlike human lines, which upregulated the $\beta$ and $\gamma$ receptor isoforms most when infected with *Chlamydia*. These results indicate that chlamydial infection results in upregulation of folic acid receptors in the cell lines tested.

Example 2

Preparation of Nanoparticles with Folic Acid on the Surface

This example uses techniques developed by applicants to anchor PEG and PEG-folate conjugate on the surface of nanoparticles, and described in Provisional Application Ser. No. 60/871,404, filed Dec. 12, 2006, incorporated herein by reference. The technique relies on the interfacial activity of PEG-X block copolymer conjugate, where X is any hydrophobic polymer (example, polylactide, polypropylene oxide, etc). Most nanoparticle formulations involve an emulsion step in the preparation. Following the formation of the emulsion, a solution of PEG-containing block copolymer (for example PLA-PEG (1000/5000 Da), with or without conjugated ligand (folic acid, for example) in an organic solvent (methanol, chloroform, etc), is added to the emulsion. PLA-PEG is a surface active block copolymer, composed of hydrophobic PLA chains and hydrophilic PEG chains.

Addition of the block copolymer to the emulsion results in the hydrophobic polylactide chain inserting itself into the oil phase and the hydrophilic PEG (or PEG-folate) chain remaining in the outer-most aqueous phase. This results in nanoparticles that contain PEG (or folate-PEG) chains on the surface. Because this method relies only on the interfacial activity of the copolymer, the technique is independent of the polymer used for nanoparticle formulation or the targeting ligand that is being used, in this case, folic acid.

Folic acid conjugation allows endocytic uptake of the conjugated carrier via the folate receptor, resulting in higher cellular uptake of the encapsulated drug. The high affinity of folic acid to its receptor (binding constant ~1 nm) and folate's small size allow its use for specific cell targeting. The ability of folic acid to bind its receptor is not altered by covalent conjugation to delivery systems.

As described in the following Examples, introduction of folic acid on the nanoparticle surface enhanced *Chlamydia*-infected cell-specific accumulation of both PLGA nanoparticles. Nanoparticles used in the Examples herein were prepared as follows:

An aqueous solution of bovine serum albumin was emulsified in an organic solution of a biodegradable polymer such as poly(D,L-lactide-co-glycolide) and a fluorescent probe such as 6-coumarin. This simple emulsion was further emulsified into an aqueous solution of polyvinyl alcohol to form a water-in-oil-in-water type emulsion. Following this, a solution of PEG-containing block copolymer (for example PLA-PEG (1000/5000 Da), with or without conjugated ligand (folic acid, for example) in an organic solvent (methanol, chloroform, etc), was added to the emulsion. The emulsion was then stirred for ~18 hours. Nanoparticles formed were recovered and washed by repeated ultracentrifugation steps (140,000 g for 1 hour, 3×), and then lyophilized. The dry nanoparticle preparation was dispersed in appropriate physiological medium as required at the time of an experiment. Bovine serum albumin used in the formulation helps in stabilizing the nanoparticles formulation, and can be replaced with serum albumin from other species, if necessary.

Example 3

Folic Acid-Derivatized Nanoparticles Accumulate More in Infected Cells

This example was performed to study the targeting of fluorescently-labeled nanoparticles to chlamydial inclusions within HEp-2 host cells infected with *C. trachomatis* serovar K. Nearly confluent monolayers of cycloheximide-treated cells were infected at MOI 5:1, and at 24 hr post-infection, infected cells were pulsed with folic acid-conjugated poly(D, L-lactide-co-glycolide) (PLGA) nanoparticles labeled with 6-coumarin. Quantitative studies indicated that infected cells accumulate significantly more folic acid-conjugated nanoparticles than uninfected cells (FIG. 2), and correlates well with increased expression of folic acid receptors in infected cells (FIG. 1).

Figure 4A:
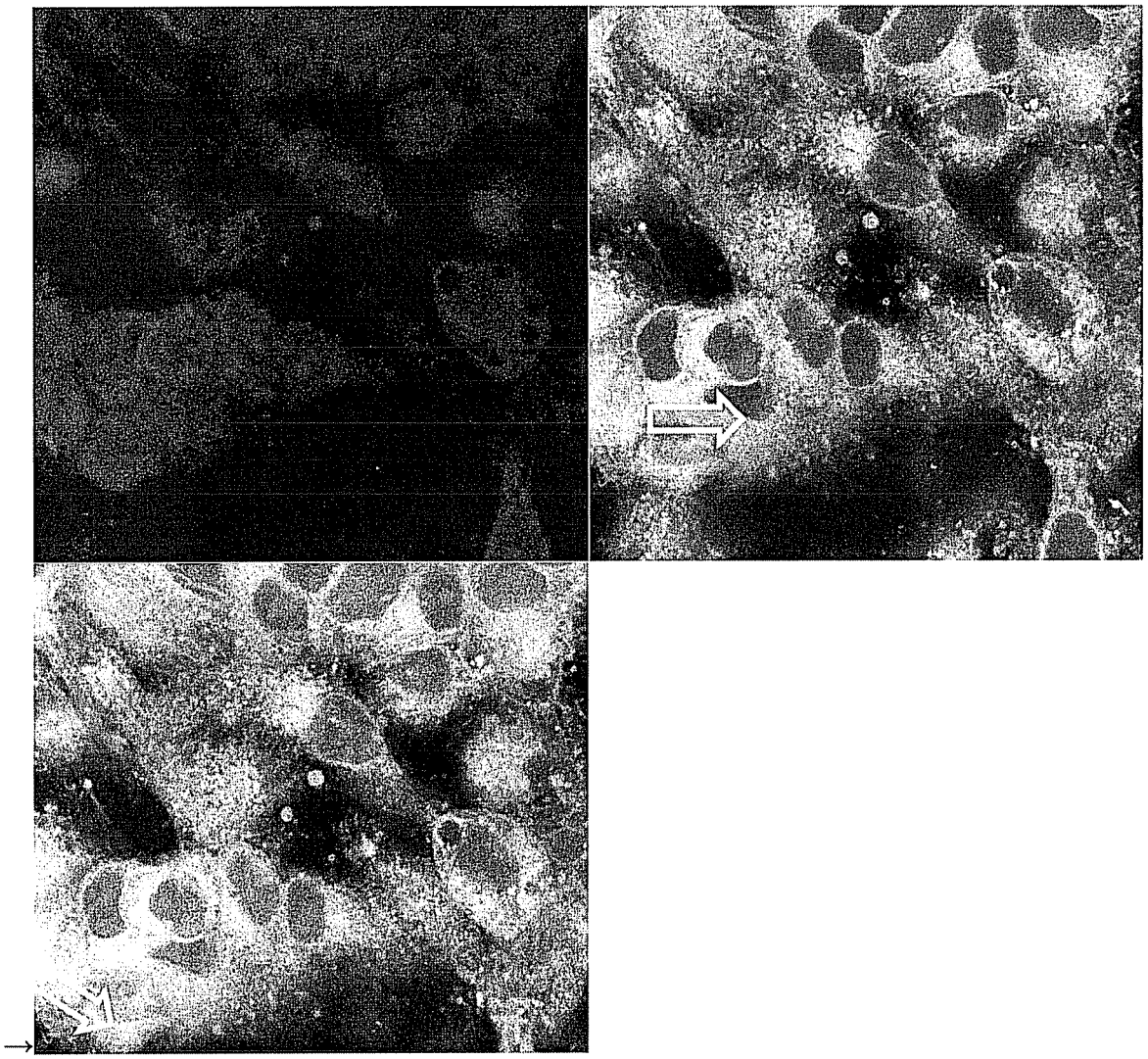
FIG. 4A-C shows images demonstrating delivery of NP containing DNA to cultured HEP-2 cells. Green indicates the presence of NP; red/yellow red indicates DNA released from NP inside inclusions (arrows).
Figure 4B:
Figure 4C:
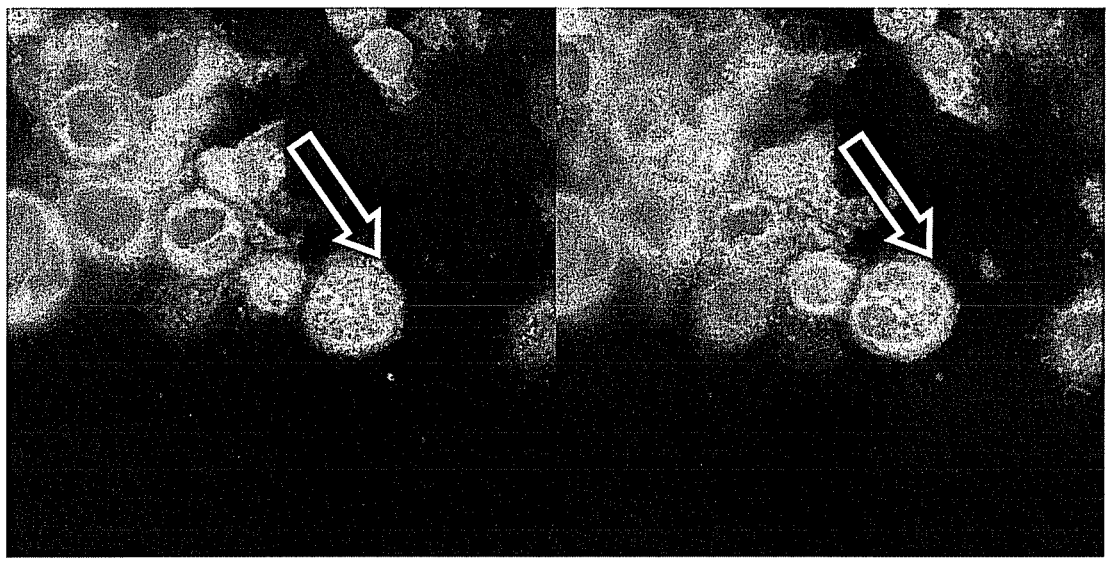

This discovery was then used to deliver plasmid DNA into Chlamydial inclusions (FIG. 4). HEp-2 cells were infected with *Chlamydia* (CT) and then pulsed with nanoparticles containing plasmid DNA (FIG. 4). Delivery to inclusions was imaged using separate fluorescent markers on the DNA and the nanoparticles. FIG. 4A shows confocal images detecting TOTO3-labeled (red) DNA within inclusions (white arrow) vs 6 coumarin-labeled nanoparticles (green) in cells which were infected 72 hrs previously with *Chlamydia trachomatis*. Co-localization of red released DNA and nanoparticles within the inclusion are seen. 4B shows an image collected at 48 hr after infection also pulsed with the nanoparticles containing DNA. A cell with a large inclusion (arrow) clearly has evidence of released DNA (red) with nanoparticles (green) within the inclusion. FIG. 4C shows two Z cuts of the same field showing localization of DNA within the inclusion and perhaps within reticulate bodies (arrow); clearly the nanoparticles are also associated with chlamydial membranes within the inclusion and the inclusion membrane.

Nanoparticle uptake in infected cells was also imaged on a RTM-3 microscope. Nanoparticles homed quite rapidly to the inclusion (FIGS. 3A, 3B); fluorescence was focused at the inclusion membrane and at the membranes of RB resident at the internal side of that membrane. Fluorescence was dimmer on elementary bodies (center of inclusion), consistent with their smaller size. This Example shows that nanoparticles constructed as described in Example 2 can be utilized to target chlamydial inclusions, thereby delivering to the inclusion the contents of the particle.

Example 4

Folic Acid-Derivatized Nanoparticles Target *Chlamydia* Infection In Vitro

This example was performed to investigate targeting fluorescently-labeled nanoparticles to chlamydial infections in a mouse model of *Chlamydia*-induced arthritis. Balb/c mice were infected with K serovar *C. trachomatis* as described (G. A. Altenberg. *PNAS* 91: 4654-4657 (1994)), and then injected intravenously with fluorescently labeled, folic acid conjugated nanoparticles 10-14 days post-infection. Animals were then imaged on Kodak animal imager. Previous studies have shown that in this model, infected macrophages reside in the synovium and genital tract (G. A. Altenberg. PNAS 91: 4654-4657 (1994)). Folic acid-conjugated nanoparticles targeted the synovial tissue in infected mice. Image analysis of excised genital tract from the treated mice showed nanoparticle accumulation in the upper genital tract. This tissue-specific targeting was absent in controls (infected mice injected with nanoparticles without folic acid, uninfected mice injected with either nanoparticle formulation). This Example shows that folic acid-directed targeting of nanoparticles to *Chlamydia*-infected cells operates not only in vitro, but also in vivo.

Example 5

Targeting of Folic Acid-Conjugated Nanoparticles to Infected Cells In Vivo

Following infection at the epithelial surfaces of the cervix, *C. trachomatis* can ascend to the upper reproductive tract. In the case of urogenital or ocular (conjunctival) infections, organisms can disseminate to distant anatomic locations such as the joint, to engender chronic sequelae. The results above in Example 4 indicate that folic acid-conjugated nanoparticles will target infected tissues in the murine model of *Chlamydia*-induced arthritis. Whole animal imaging indicated that appropriately labeled folic acid-conjugated nanoparticles would be useful for imaging infection sites to monitor the progression or eradication of infection, in addition to their use in drug delivery.

Experiments are performed to determine whether persistent joint infections in vivo can be attenuated or eliminated using antibiotics delivered by nanoparticles to infected tissues. BALB/c mice are infected genitally with $10^7$ K serovar *C. trachomatis* EB, and at different time intervals (1 to 21 d) post-infection, upregulation of the folate receptor subtypes is assessed in synovial and genital tissues harvested from infected mice; assessment is done by real time RT-PCR as above, and by western analysis for folic acid receptors.

The relative load of *C. trachomatis* is monitored in DNA preparations from each synovial sample at each time point, again by real time PCR analysis as described (M. R. Lugo and F. J. Sharom, et al. *Biochemistry* 44: 643-655 (2005). Some infected mice are subjected to IHC to determine the morphology/identity of infected cells. Chlamydial infections are identified by IHC as described above. Once these studies are completed, groups of mice are infected as above, then injected intravenously with fluorescently labeled, folic acid conjugated nanoparticles at 1, 3, 7, 10, 14, and 21 d post-infection. Animals are euthanized 30-360 min after injection and target synovial and genital tissues are harvested. Tissues are homogenized, lyophilized and extracted with methanol.

Nanoparticle concentration in the tissues are quantified using HPLC, and the data are normalized to the wet weight of the tissue. Some mice that are similarly infected and injected with nanoparticle formulation are used for imaging purposes using a Kodak whole animal imager, as above. X-rays with imaging will define the anatomic localization of nanoparticles. Data are correlated among time course of infection, bacterial load, and nanoparticle biodistribution. Distribution of folic acid conjugated nanoparticles is expected to co-localize with infected cells in synovium. Eradication of organism from infected sites is performed using folate conjugated nanoparticles containing azithromycin or other antibiotics, as described above; assessment of efficacy is done by real time PCR targeting chlamydial chromosome number in treated as compared to untreated animals and normalized to host 18S rDNA.

Example 6

Folic Acid Conjugated Particles for Delivery of Antibiotics

The data in Example 3 indicated that folic acid-conjugated PLGA particles labeled with 6-coumarin homed to *C. trachomatis*-containing inclusions at 24 hr post-infection in actively infected HEp-2 cells. The present Example is performed to measure several parameters: homing at all times post-infection, homing in cells harboring persistent chlamydiae, the efficacy of particle delivery at one or more specific times post-infection, and the efficacy of particle delivery at times post-infection in epithelial cells (active) or monocytic cells (persistent) harboring *C. pneumoniae.*

To perform this Example, 6-coumarin-labeled, folic acid conjugated (empty) PLGA particles are prepared as described above, and targeting to cultured epithelial cells (HEp-2) and monocytic cells (U937) is assessed by fluorescence microscopy using the RTM-3 microscope. Targeting is assessed at 6, 24, 48, and 72 hr post-infection of each cell type, using cells infected at MOI~1:1 with *C. trachomatis* serovar K or *C pneumoniae* strain AR-39; assessment of the relative level of fluorescence within each infected cell is quantified by computer analysis in each time course experiment with each chlamydial species and by HPLC on extracted 6-coumarin. Those data are correlated with data regarding the relative level of upregulation of each folate receptor cell type in both HEp-2 and U937 cells.

Particles are prepared containing the antibiotic azithromycin, which is known to be bactericidal for actively-growing chlamydiae of both species. Drug-containing particles are administered to HEp-2 and U937 cells at various times post-infection, allowed to home to the inclusions for 24 hr, then cultures are harvested for determination of viable chlamydiae by i) real time PCR targeting the relative level of chlamydial chromosome relative to that of control cells (identically infected but given empty particles or no particles), and recovery of IFU. Chlamydiae of either species infecting U937 cells do not fully enter the persistent state. If delivery of the antibiotic is effectively bactericidal in U937 experiments, analysis is extended to infection (both species) of normal human monocytes at 72 hr post-infection; at 72 hr post-infection, both *C. trachomatis* and *C. pneumoniae* are fully and completely in the persistent infection state.

Example 7

Antibiotic Loaded Nanoparticles

Cells and growth of *Chlamydia*. McCoy cells were seeded onto 96-well microtitre plates at a concentration of $2\times10^5$ cells per well and allowed to adhere overnight at 37° C. and 5% $CO_2$ in Eagles MEM supplemented with 10% FBS and 200 mM Glutamine. The following day, the cells were inoculated with *C. trachomatis* (UW-31, serovar K) at $10^4$ IFU/well and centrifuged at 2500 rpm for 1 hr at room temperature, followed by incubation at 37° C. for 1 hr. The inoculum was then aspirated and replaced with the appropriate two fold dilution of free drug or encapsulated nanoparticles prepared in antibiotic-free growth media containing 0.06% glucose and 1 μg/ml cyclohexamide. The cells were incubated in the presence of drug for 24 or 48 hrs post infection and then fixed with 100% MeOH. Chlamydial inclusions were detected by immunofluorescence using BioRad Pathfinder® according to the manufacturer's instructions and the plates subsequently stored protected from light at 4° C.

Microsusceptibility of *C. trachomatis* to azithromycin and rifampin. McCoy cells were seeded onto 96-well microtiter plates and then infected the next day with $10^4$ IFU/well *C. trachomatis* (serovar K). The cells were treated immediately following infection with serial two-fold dilutions of azithromycin or rifampin to a final concentration range of 31-2000 ng/ml and 1-64 ng/ml respectively and incubated for 24 or 48 hrs. FIGS. 5A and 5B show the results; the mean inclusion number was plotted as a function of concentration. The $MIC_{50}$ was defined as the minimum drug concentration needed to reduce the total number of inclusions by 50% and was determined to be ~40 ng/ml for azithromycin and ~5 ng/ml for rifampin. These data are consistent with previous sensitivity levels reported for both drugs (Suchland et al., 2003; Kutlin et al., 2005). In addition, both azithromycin and rifampin, showed no significant change in $MIC_{50}$ with length of treatment.

Example 8

Comparison of Free Drug vs Encapsulated Nanoparticles

McCoy cells were seeded onto 96-well microtiter plates and then infected the next day with $10^4$ IFU/well *C. trachomatis* (serovar K). The cells were treated immediately following infection with serial two-fold dilutions of azithromycin or rifampin encapsulated nanoparticles to a final concentration range of 31-2000 ng/ml and 1-64 ng/ml respectively and incubated for 24 or 48 hrs post infection. The mean inclusion number was plotted as a function of concentration.

To prepare free antimicrobials and drug encapsulated nanoparticles, stock solutions of azithromycin (Asta, N-66072) and rifampin (Sigma, R-5777) were prepared at a concentration of 25 mg/ml in sterile water by adding glacial acetic acid dropwise until the compounds were completely dissolved as described by Barry et al., 2004. The stocks were stored at −80° C. in single use aliquots. Subsequent dilutions were prepared immediately prior to use in defined growth media without antibiotics. Azithromycin and rifampin were also encapsulated into biodegradable, poly (D,L-lactide-co-glycolide) (PLGA) nanoparticles.

Figures 6A, 6B, 6C:
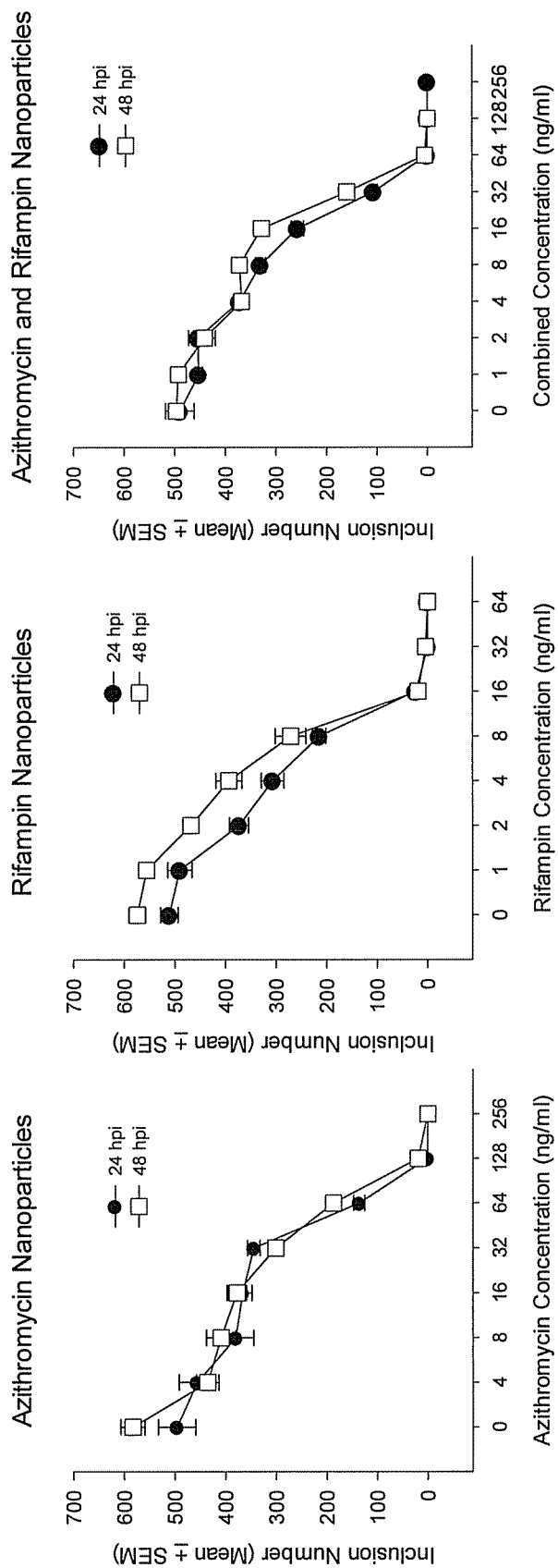
FIGS. 6A-C. McCoy cells with $10^4$ IFU/well *C. trachomatis* (serovar K) and treated immediately following infection with serial two-fold dilutions of azithromycin or rifampin encapsulated nanoparticles to a final concentration range of 31-2000 ng/ml and 1-64 ng/ml respectively and incubated for 24 or 48 hrs post infection. The mean inclusion number was plotted as a function of concentration. Both azithromycin and rifampin encapsulated nanoparticles are as effective as individual free drug.

The results are shown in FIG. 6 A-C. When used individually, both azithromycin and rifampin nanoparticles were as effective as free drug exhibiting similar $MIC_{50}$ of 40 ng/ml and 5 ng/ml respectively. Combination nanoparticles containing approximately equal amounts of azithromycin and rifampin showed an enhanced effect compared to azithromycin alone with an $MIC_{50}$ of 20 ng/ml. This is consistent with other studies that have shown that combined treatment with both azithromycin and rifampin are more effective at treating chlamydial infections than individual free drugs (Wolf and Malinverni, 1999). There was no significant shift in $MIC_{50}$ for individual or combined nanoparticle therapy with length of treatment. These results show that both azithromycin and rifampin encapsulated nanoparticles are as effective as individual free drug.

Example 9

Effectiveness of Free Drug vs Nanoparticles With Treatment at 0, 24 or 48 Hours Post Infection McCoy cells ($2\times10^5$/well) were seeded onto 96-well microtitre plates and then infected the next day with $10^4$ IFU/well C. trachomatis (serovar K). The cells were treated at 0, 24 or 48 hours post infection with serial two-fold dilutions of azithromycin or rifampin. The cells were incubated for 24 hours in the presence of drug and then fixed. Based on previous experiments we refined the concentrations ranges for each of the two free drugs and encapsulated nanoparticles. The final concentration range was 2.5-10 ng/ml for rifampin and 25-100 ng for azithromycin.

Figures 7A, 7B, 7C:
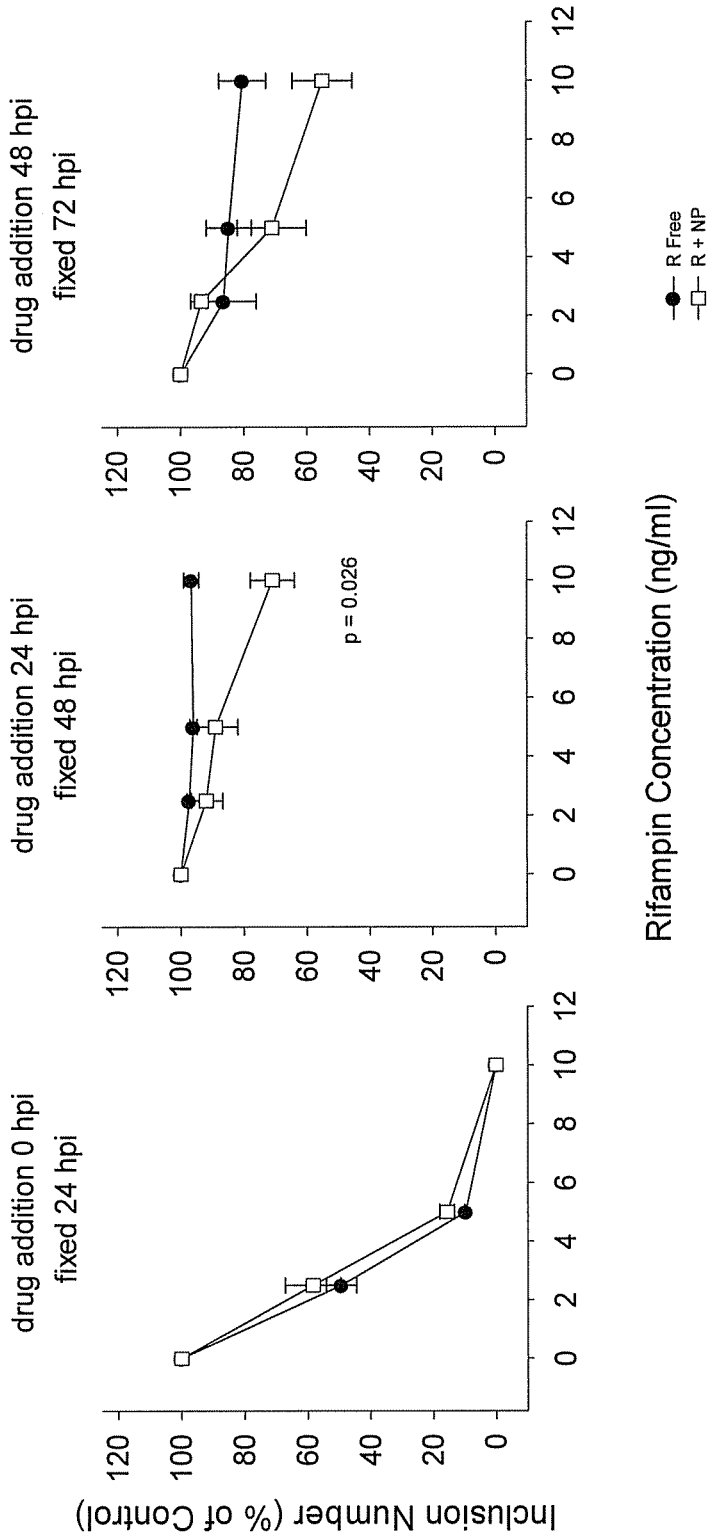
FIG. 7A-C. McCoy cells ($2 \times 10^5$/well) infected with $10^4$ IFU/well *C. trachomatis* (serovar K), then treated at 0, 24 or 48 hours post infection with serial two-fold dilutions of rifampin. The cells were incubated for 24 hours in the presence of drug and then fixed. The final concentration range was 2.5-10 ng/ml for rifampin. Statistical significance based on pair-wise rank sum test is shown.
Figures 8A, 8B, 8C:
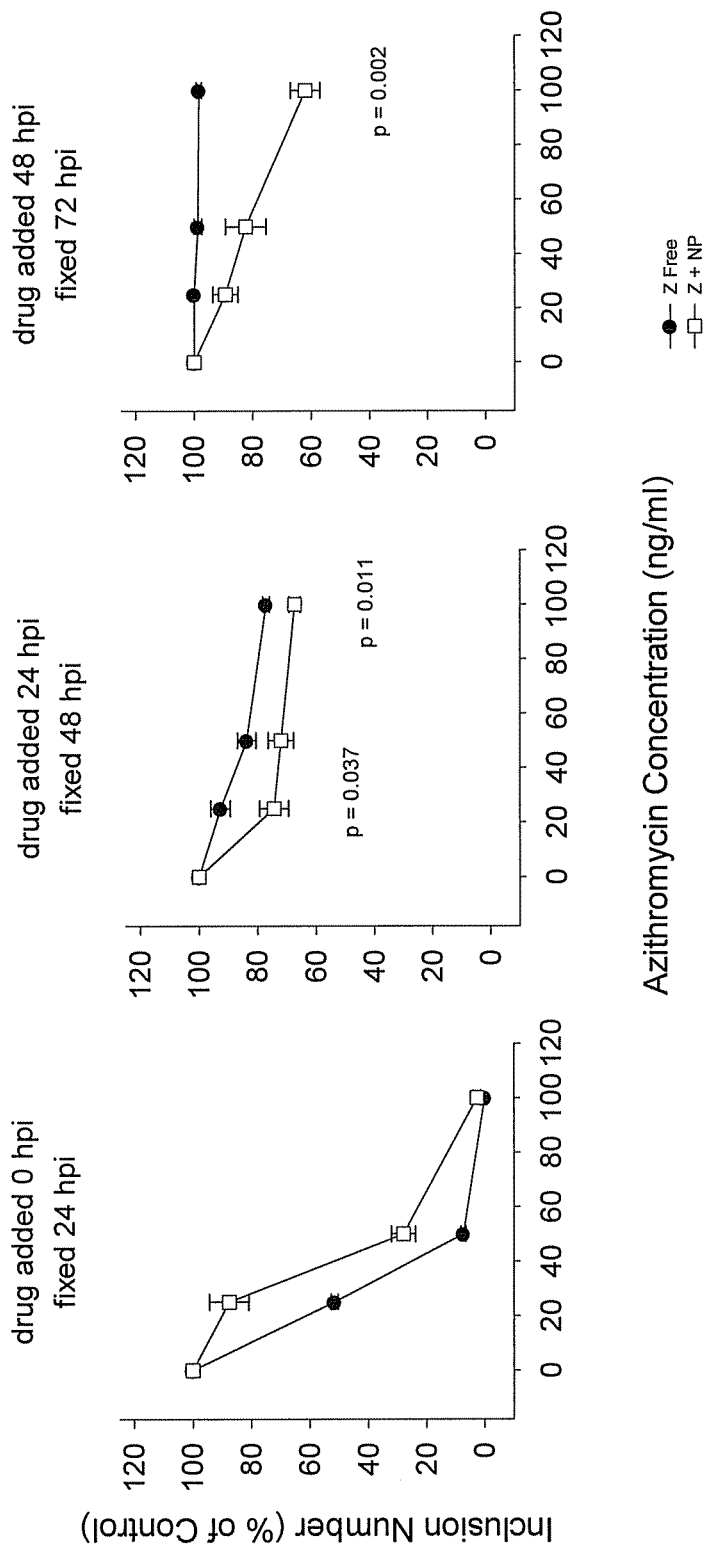
FIG. 8A-C. McCoy cells ($2 \times 10^5$/well) infected with $10^4$ IFU/well *C. trachomatis* (serovar K), then treated at 0, 24 or 48 hours post infection with serial two-fold dilutions of azithromycin. The cells were incubated for 24 hours in the presence of drug and then fixed. The final concentration range was 25-100 ng for azithromycin. Statistical significance based on pair-wise rank sum test is shown.

When free drug or encapsulated nanoparticles were added immediately following infection, the response was similar to that observed previously with an $MIC_{50}$ of 5 ng/ml for rifampin and 40 ng/ml for azithromycin. In contrast, when drug was added 24 or 48 hours post infection a marked insensitivity was observed, reflected in a minimal decrease in inclusion number with increasing dose. (FIG. 7 A-C, FIG. 8, A-C.) There was some indication that the cells treated with drug encapsulated nanoparticles were more sensitive than those treated with free drug, albeit the $MIC_{50}$ was shifted out of the range of this experiment. Statistical significance based on pair-wise rank sum test is written on the figures.

Secondary inclusions were observed at 72 hpi. These inclusions showed sensitivity similar to infected cells treated immediately post infection. This suggests that sensitivity to azithromycin and rifampin is related to a specific window in the Chlamydial life cycle.

Example 10

Responsiveness of Infected Cells to Drug Encapsulated Nanoparticles vs Free Drug when Treatment is Delayed for 24 HPI McCoy cells ($2\times10^5$/well) were seeded onto 96-well microtitre plates and then infected the next day with $10^4$ IFU/well C. trachomatis (serovar K). The cells were treated at 0 or 24 hours post infection with serial two-fold dilutions of azithromycin or rifampin. The cells were incubated for 24 hours in the presence of drug and then fixed. Previous data indicated that there is a dramatic shift in $MIC_{50}$ when drug treatment is delayed. We, therefore, extended the concentration ranges for the two drugs. The final concentration range for rifampin was 2.5-80 ng/ml and for azithromycin was 25-800 ng/ml.

Figure 9B:
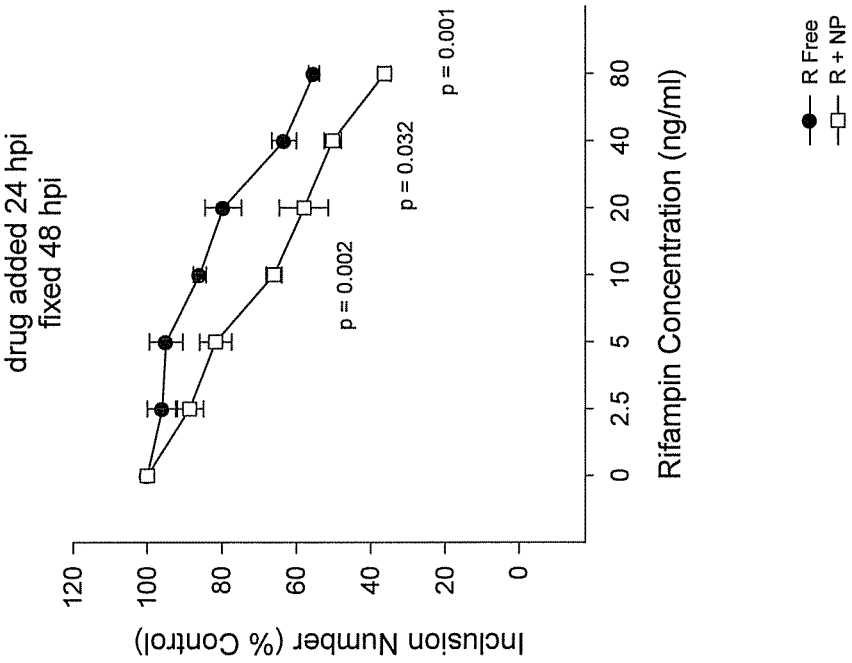
FIGS. 9A and 9B. McCoy cells ($2 \times 10^5$/well) were infected with $10^4$ IFU/well *C. trachomatis* (serovar K), then treated at 0 or 24 hours post infection with serial two-fold dilutions of rifampin. The cells were incubated for 24 hours in the presence of drug and then fixed. The final concentration range for rifampin was 2.5-80 ng/ml and for azithromycin was 25-800 ng/ml. Improved sensitivity was observed at 40 and 80 ng/m. A 50% reduction in inclusion number was observed for rifampin nanoparticles compared to free drug at 40 ng/ml.
Figure 9A:
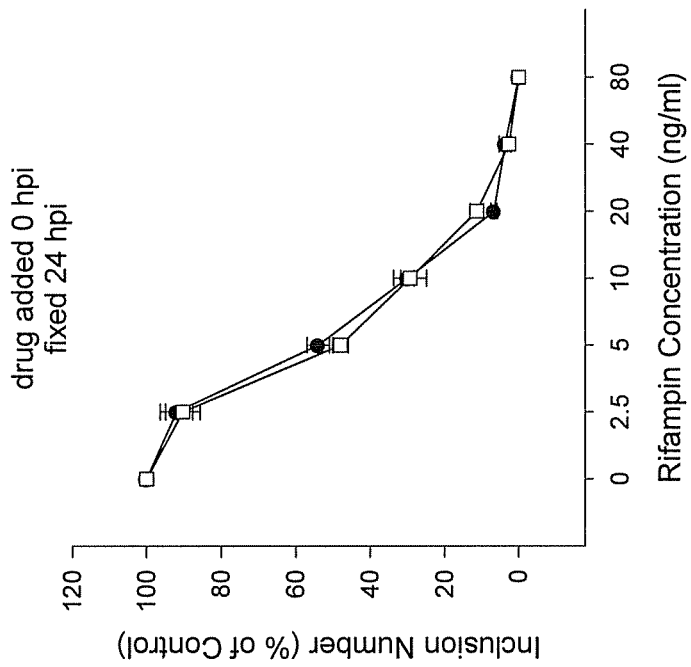
Figure 10A:
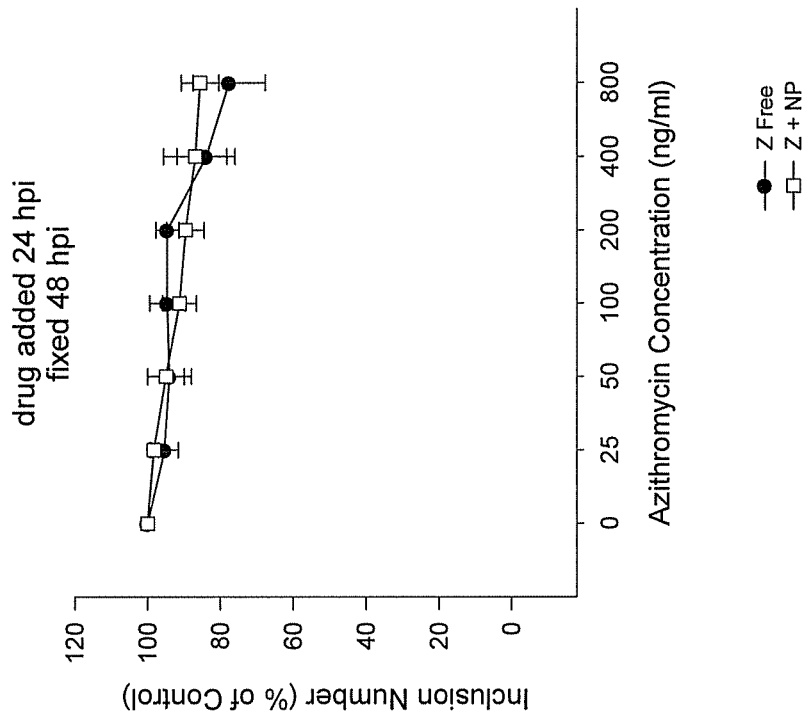
FIGS. 10A and 10B. McCoy cells ($2 \times 10^5$/well) were infected with $10^4$ IFU/well *C. trachomatis* (serovar K), then treated at 0 or 24 hours post infection with serial two-fold dilutions of azithromycin. The cells were incubated for 24 hours in the presence of drug and then fixed. The final concentration range for azithromycin was 25-800 ng/ml. Inclusion number expressed as percent of control was plotted as a function of concentration. There was no improvement in response to drug using drug-loaded nanoparticles compared to free drug when treatment was added at 24 hpi (hours post-infection).
Figure 10B:
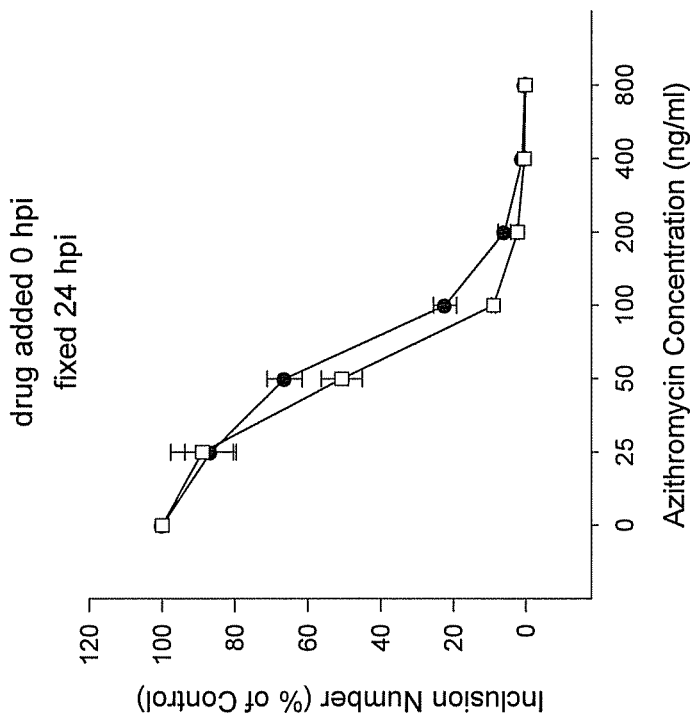

The results are shown in FIG. 9A-B and indicate that sensitivity to drug may be enhanced when rifampin is delivered in nanoparticles relative to free drug. Inclusion number expressed as percent of control was plotted as a function of concentration. In the case of rifampin improved sensitivity was observed at 40 and 80 ng/ml. A 50% reduction in inclusion number was observed for rifampin nanoparticles compared to free drug at 40 ng/ml. In the case of azithromycin, there was no improvement in response to drug using nanoparticles compared to free drug when treatment was added at 24 hpi (FIG. 10A-B).

Consistent with previous data, for both rifampin and azithromycin, nanoparticle delivered antimicrobials were as efficient as free drug when treatment was added immediately post infection. This is also supportive that it is EB to RB transition and early stages of inclusion formation that seem to be the window of maximum sensitivity.

The next experiment was performed to determine whether extending the length of exposure to drug would enhance the shift of $MIC_{50}$ observed for nanoparticles vs free drug, and whether there is a difference in targeted nanoparticles vs drug encapsulated alone. McCoy cells ($2\times10^5$/well) were seeded onto 96-well microtitre plates and then infected the next day with $10^4$ IFU/well C. trachomatis (serovar K). The cells were treated at 24 hours post infection with serial two-fold dilutions of azithromycin or rifampin. The cells were incubated for 24 hours or 48 hours in the presence of drug and then fixed.

Figure 11B:
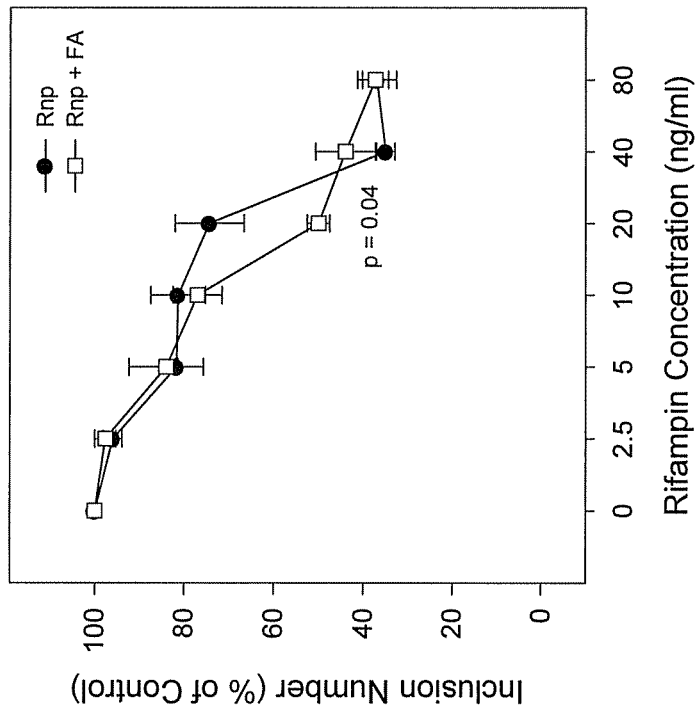
FIGS. 11A and 11B. McCoy cells ($2 \times 10^5$/well) were seeded onto 96-well microtiter plates and then infected the next day with $10^4$ IFU/well *C. trachomatis* (serovar K). The cells were treated at 24 hours post infection with serial two-fold dilutions of rifampin. The cells were incubated for 24 hours or 48 hours in the presence of drug and then fixed. When drug was added at 24 hpi and left on for 24 hours, there was no difference in sensitivity between cells treated with nonFA or FA targeted nanoparticles. Both showed an $MIC_{50}$ between 40 and 80 ng/ml. When drug was added at 24 hpi and left on for an additional 48 hours, there was an enhanced sensitivity compared with 24 hour drug exposure. The MIC50 shifted to 20-40 ng/ml. A significant change in slope at 10 ng/ml suggests that FA targeted nanoparticles improved sensitivity over drug encapsulated nanoparticles alone.
Figure 11A:
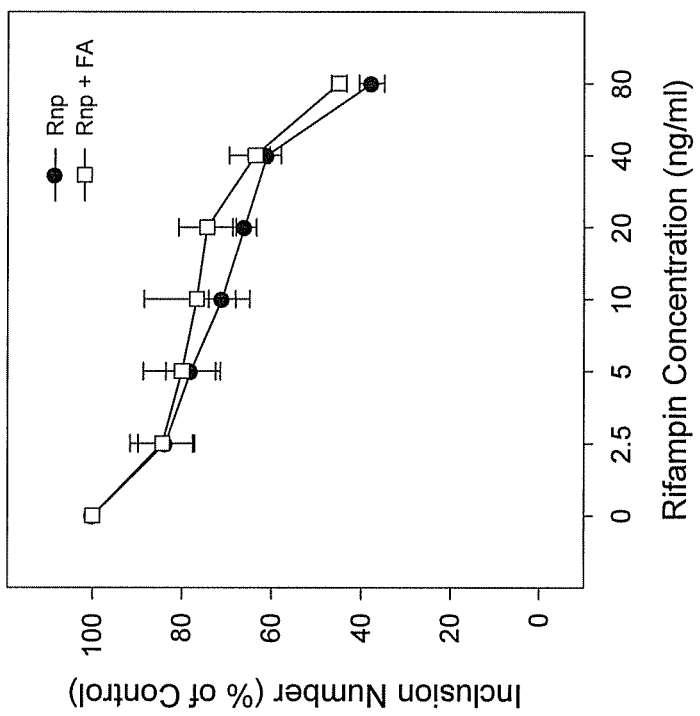

When drug was added at 24 hpi and left on for 24 hours, there was no difference in sensitivity between cells treated with nonFA or FA targeted nanoparticles. Both show an $MIC_{50}$ between 40 and 80 ng/ml. (FIG. 11.) This is consistent with previous results and show an advantage over free drug alone where $MIC_{50}$ is greater than 80 ng/ml. When drug is added at 24 hpi and left on for 48 hours, there is an enhanced sensitivity compared with 24 hour drug exposure. The MIC50 shifts to 20-40 ng/ml. A significant change in slope at 10 ng/ml suggests that FA targeted nanoparticles improve sensitivity over drug encapsulated nanoparticles alone.

Figure 12B:
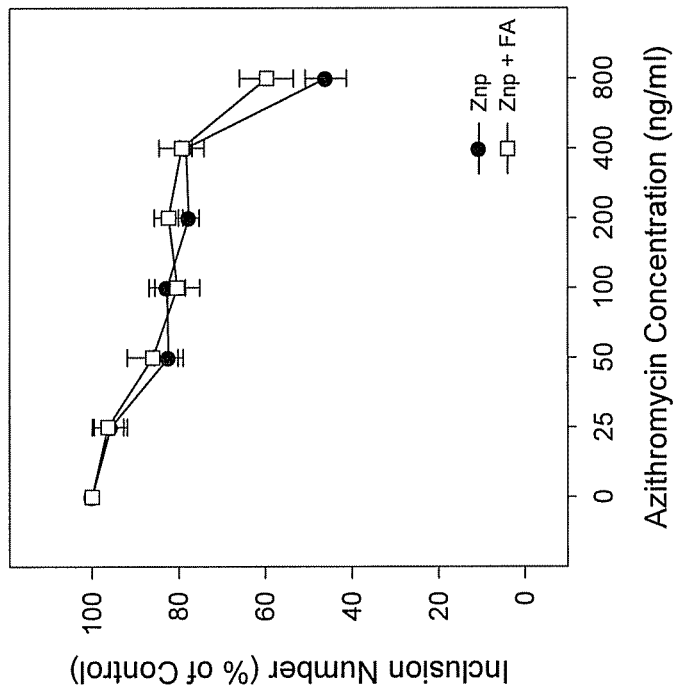
FIGS. 12A and 12B. McCoy cells ($2 \times 10^5$/well) were seeded onto 96-well microtiter plates and then infected the next day with $10^4$ IFU/well *C. trachomatis* (serovar K). The cells were treated at 24 hours post infection with serial two-fold dilutions of azithromycin. The cells were incubated for 24 hours or 48 hours in the presence of drug and then fixed. When drug was added at 24 hpi and then left on for 24 hours there was a minimal response with non FA nanoparticles, however, the $MIC_{50}$ was still greater than 800 ng/ml. In contrast when drug was added at 24 hpi and left on for 48 hours both targeted and non targeted nanoparticles showed enhanced sensitivity with an $MIC_{50}$ near to 800 ng/ml.
Figure 12A:
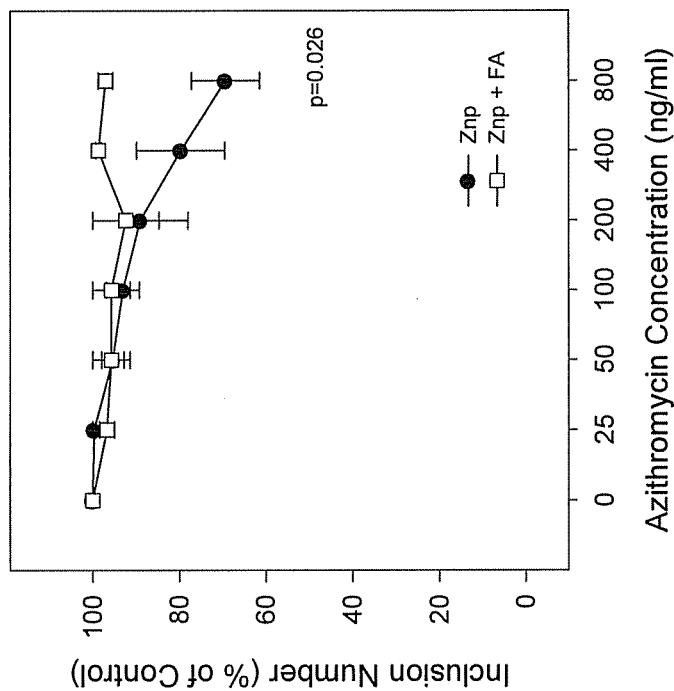

For azithromycin, when drug was added at 24 hpi and then left on for 24 hours there was a minimal response with non FA nanoparticles, however, the $MIC_{50}$ was still greater than 800 ng/ml. In contrast when drug was added at 24 hpi and left on for 48 hours both targeted and non targeted nanoparticles showed enhanced sensitivity with an $MIC_{50}$ near to 800 ng/ml. (FIG. 12.)

Example 11

Folic Acid Conjugated Nanoparticles Target Chlamydia Infected Cells

Figure 13:
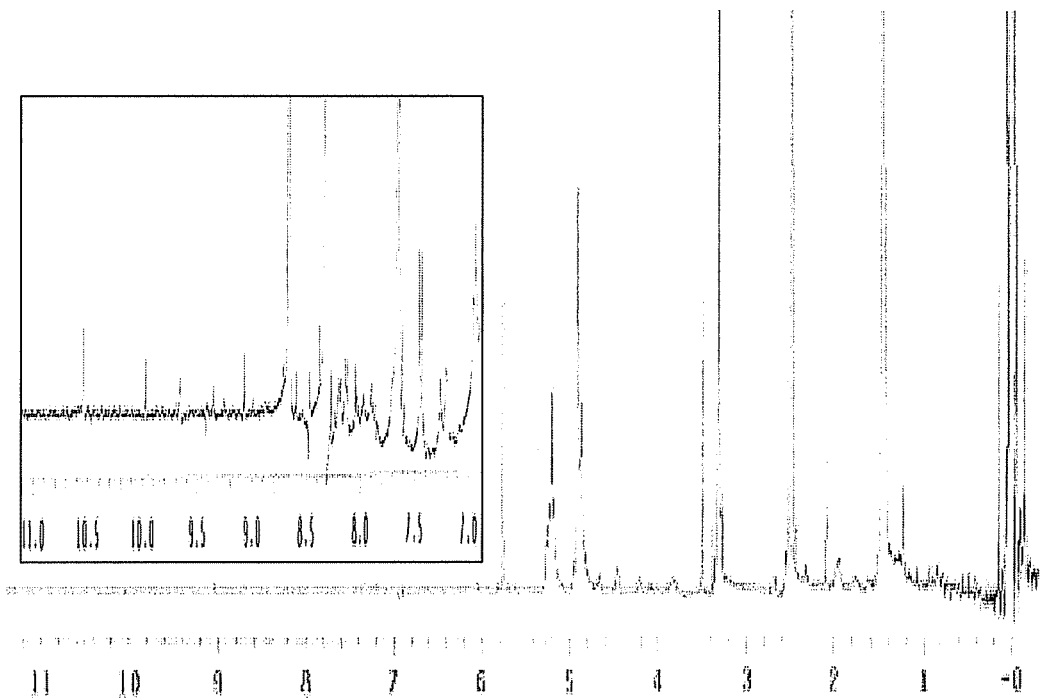
FIG. 13 shows $^1H$ NMR spectrum of PEG-FA conjugated PLGA nanoparticles (PEG: $CH_2$ at 3.59 ppm; PLA: CH at 1.25 ppm and $CH_3$ at 5.22 ppm; and folic acid: aromatic protons at 6.62 and 7.61 ppm and aliphatic amide proton at 8.1 ppm).
Figure 14:
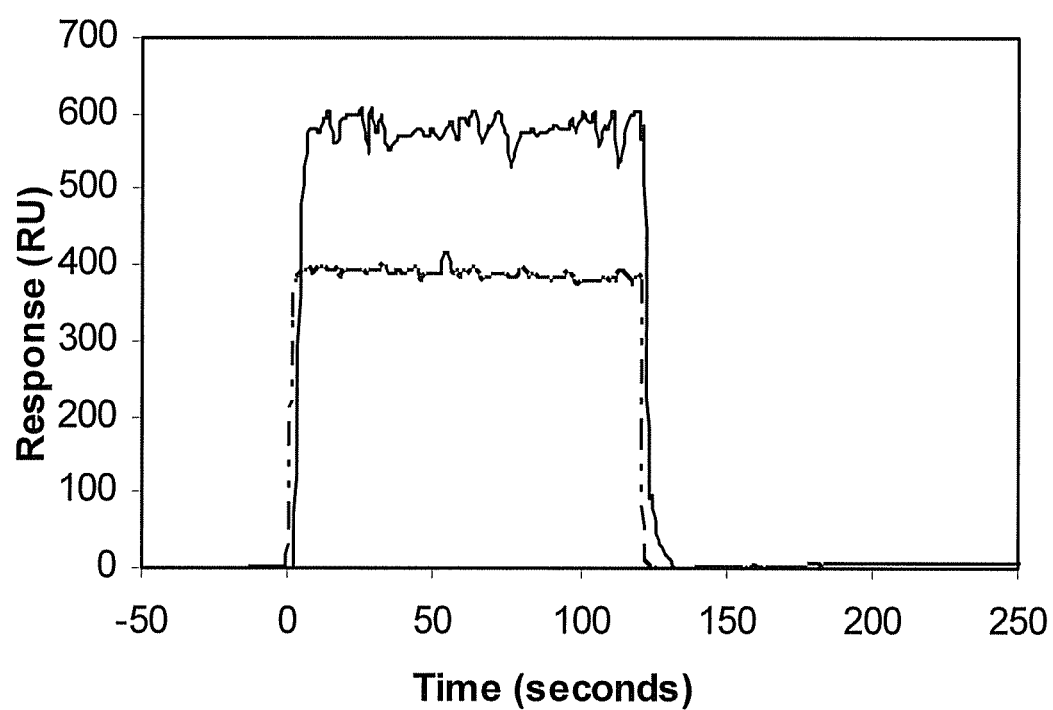
FIG. 14. SPR analysis of folic acid (FA) conjugated nanoparticles (solid line) on anti-folic acid monoclonal antibody coated surface. The anti-folate monoclonal antibody (Chemicon) was amine coupled to the sensor chip and nanoparticle formulations were injected at a concentration of 10 mg/ml. Nanoparticles without folic acid (dashed line) as control.
Figure 15:
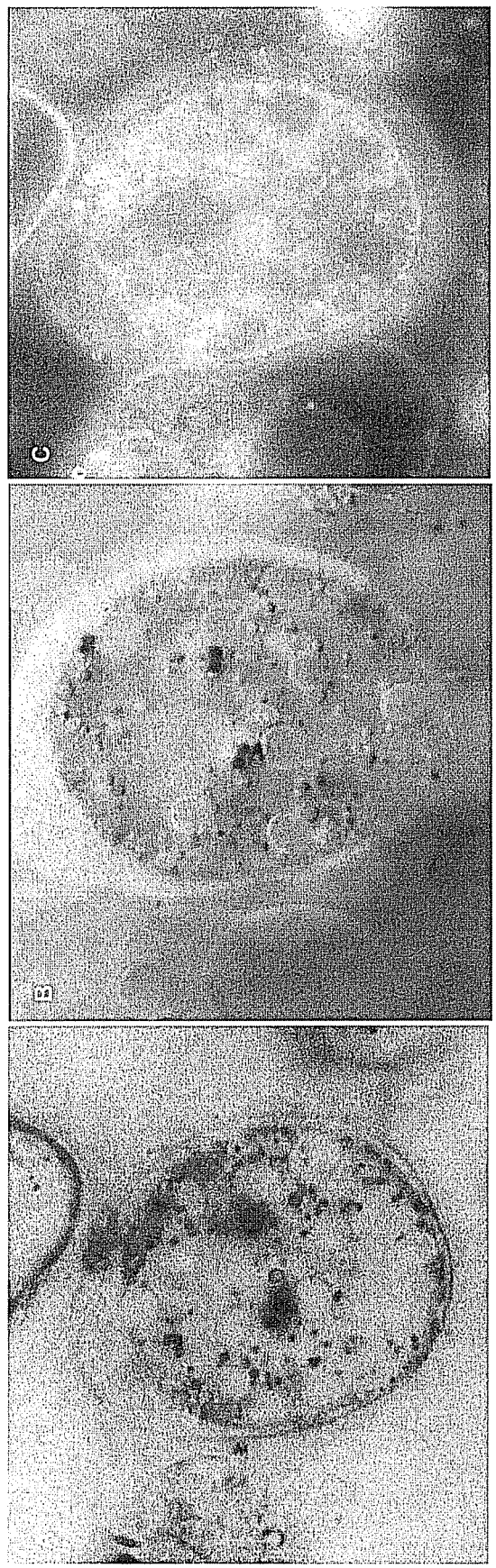
FIG. 15. Shown in FIGS. 15A-C are high resolution images of a McCoy cell from cultures infected and grown in the presence of PenG. Cells are unstained and captured under real time microscopy using the RTM-3 microscope with Richardson contrast (A), DIC-like mode (B), and fluorescence mode (C). IFNγ treatment induced smaller inclusions filled with atypical large RB at 48 hr p.i.; untreated, infected cultures had large inclusions primarily filled with EB (not shown). 100× original mag., RTM3 microscope.
Figure 16:
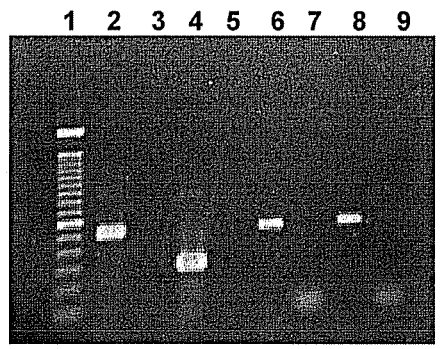
FIG. 16. Representative DnaA and FtsW PCR results for two mice originally positive for 16S rRNA, plasmid and/or omp1 as described above (upper vs lower lanes) are shown in this agarose gel: Lanes contain: 1, 100 bp Std; 2, +ctrl DNA; PCR for dnaA; 3, −ctrl, water with dnaA; 4, +ctrl, DNA, PCR for ftsW; 5, −ctrl for ftsW; 6, Knee A, cDNA, RT-PCR for dnaA; 7, Knee A, cDNA, RT-PCR for ftsW; 8, Knee B, cDNA, dnaA; 9, Knee B, cDNA, ftsW. These results clearly demonstrate that dnaA remains positive while ftsW has been shut off. Positive controls (acutely infected McCoy cells) for the two products were run in the same experiments. β-actin was used for normalization FIG. 17. Images demonstrating targeting of folic acid-conjugated nanoparticles to infected host cells, using the Kodak imaging system. Panel A, fluorescence image of an infected mouse injected intravenously with 6 coumarin-folic acid-conjugated particles. Panel B, the same mouse viewed under X-ray. The joint tissue showing accumulation of nanoparticles is indicated by arrows.

This example was performed to investigate the targeting of fluorescently-labeled nanoparticles to Chlamydial inclusions in an in vitro cell culture model. Folic acid conjugated-nanoparticles were formulated using a simple, interfacial activity-assisted method of nanoparticle surface functionalization (manuscript submitted). This method utilizes the fact that when an ampiphilic diblock copolymer is introduced into a biphasic (oil/water) system, the copolymer adsorbs at the interface. The hydrophobic block of the copolymer tends to partition into the oil phase while the hydrophilic block tends to remain in the aqueous phase. In the proposed approach, we introduce a diblock copolymer such as polylactide-polyethylene glycol (PLA-PEG) with folic acid conjugated to the PEG chain (PLA-PEG-folic acid). This results in partitioning of PLA block into the polymer containing oil phase and PEG-ligand block into the aqueous phase. Removal of the organic solvent results in the formation of nanoparticles with PEG-folic acid on the nanoparticle surface. Micelles formed due to the self-assembly of the PLA-PEG block copolymer are removed by extensive dilution and washing of the system. We call this method Interfacial Activity Assisted Surface Functionalization (IAASF). Using this approach, we fabricated nanoparticles from a biodegradable polymer PLGA and surface functionalized with PEG and folic acid as targeting ligand. Incorporation of PLA-PEG segments along with the folic acid in nanoparticles was confirmed by proton NMR (FIG. 13). Presence of PEG and folic acid on the surface was confirmed by contact angle measurement, and surface plasmon resonance (FIG. 14).

Decrease in the contact angle of water from 49±5 to 33±3 for unconjugated and PEG-conjugated nanoparticles ($P<0.05$) suggests that incorporation of PEG significantly increased the hydrophilicity of the nanoparticle surface. This was expected, since PEG is more hydrophilic than PLGA. The decreased hydrophilicity of PEGylated nanoparticles is expected to contribute to the decreased biorecognition and increased circulation time of particles. Surface plasmon resonance studies indicated that not only was folic acid present on the surface of the particles but was also available for binding. A significant difference of about 200 RU in binding to the anti-folate antibody coated surface was observed for nanoparticles with and without folic acid on the surface (FIG. 14).

Example 12

Development of Persistence Phenotype with K Serovar

Two approaches were used with in vitro infected McCoy cells to test whether aberrant inclusions developed. Cells were exposed to penicillin G (PenG, 100 U/ml added at 24 hr p.i.) [70,71]. Pen G induced the typical large aberrant RB shown by others (FIG. 15). In these inclusions, only the small number of EB had motion, and the aberrant forms were stationary in the inclusion. Treatment of infected cells with recombinant IFNγ for 24 hr induced small inclusions that appeared to contain exclusively RB (not shown). With primary cultured human monocytes, no treatment was necessary to elicit persistence by day 3 post-infection.

This was supported by additional experiments with acutely *Chlamydia*-infected and uninfected cells: semi-confluent monolayers of HEp-2 cells were infected with *C trachomatis* serovar K at an MOI 5 and overlaid with cycloheximide-containing medium. At 24 hr p.i., infected and uninfected cells were pulsed for 5-15 min. with folic acid-conjugated nanoparticles labeled with 6-coumarin. Quantitative studies indicate that infected cells accumulate significantly more folic acid-conjugated nanoparticles than uninfected cells (FIG. 2), and correlates well with increased expression of folic acid receptors in infected cells (FIG. 1).

Nanoparticle uptake in live, infected cells was also imaged on the RTM-3 microscope. Remarkably, nanoparticles appeared to have homed quite rapidly to the inclusion within 15 min of addition (FIG. 3 A, B); indeed fluorescence is focused at the inclusion membrane and at the membranes of RB resident at the internal side of that membrane and differentiated EB deeper in the inclusion. Thus, initial studies suggest that particles constructed in the manner given can be utilized to target Chlamydial inclusions, thereby delivering to the inclusion the contents of the particle.

Example 13

Nanoparticles Deliver their Payload into Chlamydial Inclusions

This example was performed to determine whether nanoparticles can deliver their contents into the inclusion complexes. PLGA nanoparticles containing TOTO3-labeled plasmid DNA were prepared using previously published methods. TOTO-labeled DNA was chosen as the payload because: (1) TOTO-labeled DNA is red fluorescent and enables the use of epi-fluorescence microscopy to track intracellular delivery; and (2) high binding affinity of TOTO for DNA and the lack of fluorescence in the absence of DNA binding ensure low false positives. For these studies, nearly confluent monolayers of HEp-2 cells were infected with *C trachomatis* as above. At 24 hr p.i. cells were pulsed with DNA-loaded nanoparticles that were also labeled with 6-coumarin. At 48 hr p.i., nanoparticles (green fluorescence) were found within the inclusions. Importantly, nanoparticles were found to release their DNA payload (red fluorescence) within the inclusion complexes (not shown). This example indicates that PLGA nanoparticles can be utilized to deliver their contents into Chlamydial inclusion complexes.

Example 14

Molecular Evidence for Persistent Infection in Mouse Knees Following Genital Infection Persistently infected cells may be a potent source of reactivated infection, increased inflammation at the tissue sites including upper genital tract, synovial tissue, and disseminated sites associated with *C trachomatis* and *C pneumoniae*. In two studies of acutely infected HEp-2 cells and persistently infected human monocytes [25,26], it was found that transcription of genes important in Chlamydial cell division and energy metabolism/transfer were markedly different under the two infection states and congruent with decreased Chlamydial cell division and altered metabolic activity during persistence. The key genes for comparison which are relevant to this example are dnaA (Chlamydial DNA replication; turned on in cells with acute or persistent infection), ftsK and ftsW (Chlamydial cell division; turned off in persistent infection in monocytes; supported by evidence from Belland et al [72] to be downregulated in IFNγ-treated persistently infected cells) and others. Human synovial samples from ReA patients yielded data for dnaA/ftsW and other genes supporting persistent infection in those tissues. Total nucleic acids were obtained from 17 mouse synovial samples days 7, 10 or 14 p.i., and screened by RT-PCR for Chlamydial 16SrRNA or primary transcripts [75], MOMP [76], and plasmid [77]. Ten of 17 samples were positive by at least one assay, 7 were positive by all three assays. Positive samples were then tested for presence of transcripts from dnaA and ftsW [25,78] by RT-PCR (see Detailed Methods for details). In the RT-PCR, 2 samples (d.10 p.i.) were positive for both dnaA and ftsW transcripts, 7/17 were negative for both messengers, and 7 of 17 were positive for dnaA transcripts but negative for ftsW and reflective of persistent infection. A gel showing results for two different mice is given in FIG. 16. These data show that a molecular phenotype for persistent infection develops in knees of the mouse genital infection model, and support the use of targeted nanoparticle therapy on active vs persistent infection in synovial tissues.

Example 15

Folic Acid Conjugated Nanoparticles Target *Chlamydia* Infected Tissue

Figure 17:
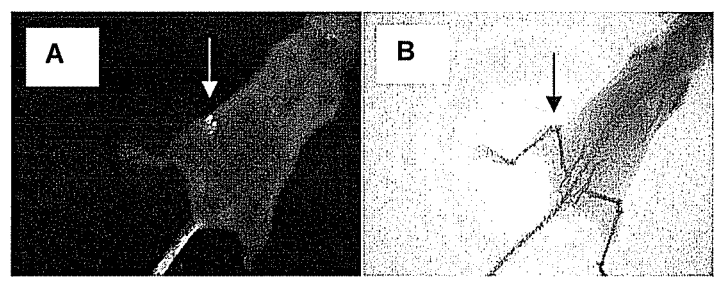

BALB/c mice were infected with *C trachomatis* (UW-31/K) as in previous studies [22], and then injected I.V. with 6 coumarin-labeled, folic acid-conjugated nanoparticles 10-14 days p.i. Animals were then imaged in a Kodak animal imager. Previous studies have shown that in this model, infected mononuclear cells/macrophage reside in the synovium and genital tract [22]. As shown in FIG. 17, folic acid conjugated nanoparticles appear to target the synovial tissue in infected mice. This tissue-specific targeting was absent in controls (infected mice injected with nanoparticles without folic acid, uninfected mice injected with either nanoparticle formulation; not shown) Image analysis of excised genital tract from the treated mice showed particle accumulation in the upper genital tract (not shown).

Figure 18:
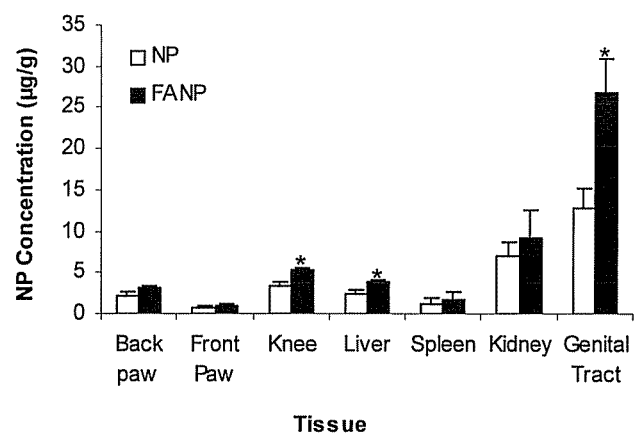
FIG. 18. Accumulation of folic acid-conjugated nanoparticles in infected host tissue. Nanoparticles with folic acid on the surface (FANP) or without (NP) were injected intravenously in an infected mouse. NP concentration in the different tissues was determined by HPLC. *$P < 0.05$ FIG. 19. Antibiotic delivery in nanoparticles effectively reduces Chlamydial viability. McCoy cells were infected with *C trachomatis* serovar K at MOI=1. After adsorption, at the time of overlay medium addition, different concentrations of rifampin (R), azithromycin (Z) or combination of both drugs (Z+R) were also added. Drugs were administered either encapsulated in nanoparticles (top panel) or dissolved in growth medium (bottom panel). Chlamydial viability was determined by counting the number of inclusions/well. Infected cells without either drug yielded a mean of ~550 IFU (top) and 632 IFU/well (bottom). Concentrations for Z+R=Z (loading was 5 μg/ml with 6 μg/ml R) (top panels). Free drugs in combination are compared to single drug (open symbols, bottom panels).

In addition to imaging, nanoparticle levels in various tissues from the same mice were also quantified. In agreement with the imaging experiment, folic acid conjugated particles were found to accumulate in significantly higher quantities in knee joints, liver and genital tract than nanoparticles without folic acid (FIG. 18, P<0.05; n=3-4). Thus, folic acid-directed targeting of nanoparticles to *Chlamydia*-infected cells operates not only in vitro, but also in vivo.

Example 16

Effect of Combination Antibiotic Treatment on Chlamydial Viability

Figure 19:
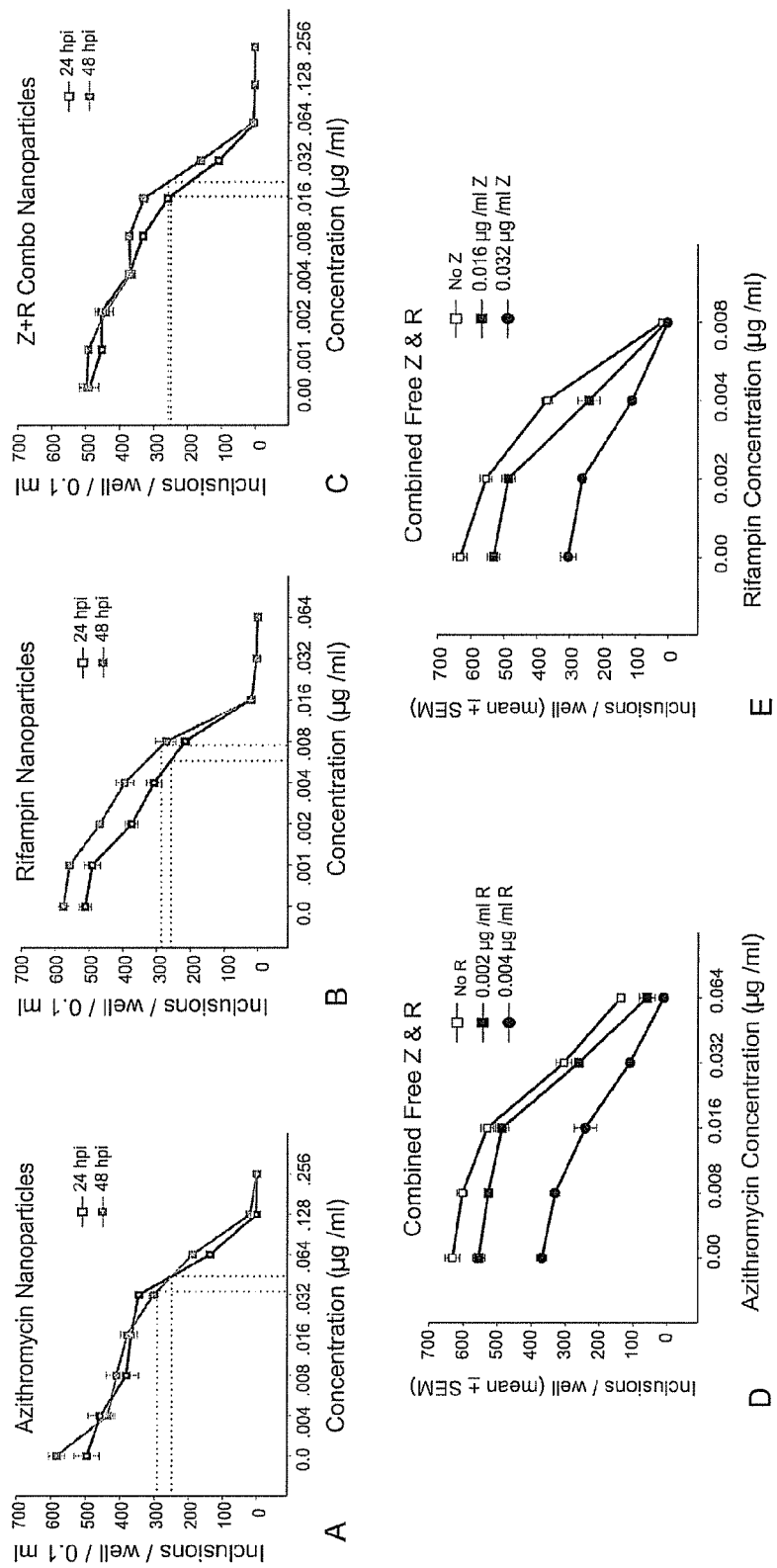

This example describes the effect of combining azithromycin and rifampin and their encapsulation in nanoparticles on the IC50 of the individual drugs. Nanoparticles used in this example were not conjugated to folic acid. As can be seen from FIG. 19, combination therapy was significantly more effective than individual drugs, both free and encapsulated in nanoparticles. When treated individually, MIC50s for both free and nanoparticle-encapsulated drugs were 0.008 μg/ml and 0.032 μg/ml, respectively. However, in the presence of 0.004 μg/ml rifampin, the MIC50 of azithromycin dropped to 0.016 μg/ml, while in the presence of 0.016 μg/ml azithromycin, the MIC50 of rifampin reduced to 0.002 μg/ml. It was interesting to note that despite releasing only a fraction of the drug(s), nanoparticle antibiotics were at least as effective as free drugs. The inventors' previous studies have shown that, in general, less than 50% of encapsulated drugs are released in 24-48 hrs [40].

Example 17

Nanoparticles to Treat *Chlamydia* Infection

Data disclosed herein indicate that chlamydiae-infected cells up-regulate expression of genes encoding folic acid receptors (FAR), suggesting that the association of folic acid with the therapeutic modality will target infected cells in a reasonably specific fashion. Assessment of FAR expression patterns will be followed by production of non-derivatized and folate-derivatized nanoparticles and testing the ability of those particles to target infected cells, using well-developed and characterized in vitro systems. An in vivo murine model of chlamydial infection is used.

Overexpression of FAR as a function of chlamydial infection, and the use of a folic acid conjugated delivery system to target cells infected with chlamydiae have not reported previously. Molecular genetic analytical systems will determine the relationship between progression of infection over time and differential folate receptor expression at both cellular and tissue levels. This information is used to determine the optimal time for targeting the infected cells/tissue and whether such therapy will work later during chronic/persistent infection.

Examples described above indicated that chlamydial infection induces differential up-regulation of FAR in cultured human epithelial cells and macrophages, and murine macrophages in vitro at 24 hrs pi. Translation of the up-regulated mRNA encoding the receptors should follow, and be reasonably congruent with, the transcript level increase. Initial results suggest that the up-regulated receptors are present on the cell membrane of the host cell, and possibly on the inclusion membrane as well since the latter is derived from host cell membrane/components. In Aim One, expression of mRNA encoding each of the FAR subtypes will be defined following infection with *C trachomatis* serovars (see below) using HEp-2 and McCoy cells as hosts; HEp-2 cells are of primary interest since human epithelial cells represent the target host cell type in primary infection.

Monocytic cells also must be analyzed since they have been shown to be the host cell type for dissemination and persistent infection [22,79]. Relative levels of folic acid receptor mRNA/cDNA will be determined quantitatively for each of the three dominant receptor types ($\alpha$, $\beta$, $\gamma$) by real time RT-PCR at t0, 6, 12, 24, 36, 48, and 72 hrs post-infection of each of the two host cell types during normal active infection. Cells will be grown and infected at MOI ~1-5 as in our earlier publications [eg, [25,26]. Because we have used K serovar for most previous studies, we will use it for initial experiments. However, ocular and genital strains of *C trachomatis* have been shown to differ at the genetic level [80], and we thus will assess FAR transcript levels in the same host cell types infected with C (ocular) serovar.

Primers targeting each of the three folate receptor subtypes (human and mouse) have been designed and tested in real time RT-PCR assays. Relative transcript levels will be expressed as a function of time post-infection relative to their levels in uninfected host cell types of the same line. Concomitant assessment of the relative level of translation product from each receptor subtype gene will be done using image analysis software on western analyses for each subtype. The mAb to be used in these westerns are commercially available (Santa Cruz and Abcam) and differentially recognize the three versions of the human and mouse receptor.

In addition to quantitation of transcription and translation product levels from the three receptor genes, we will use the same FAR-targeted mAb in standard immunistochemical (IHC) analyses to assess the localization and overall level of each receptor on chlamydiae-infected vs uninfected host cells of each type; receptor density and distribution will be determined in each host cell type for infection by K serovar and for infection by C serovar. For the Western and IHC experiments, cells will be grown and infected and the cell lysates obtained at different time points will be analyzed by Western blotting. IHC will be performed. In these IHC experiments, we will determine whether the three receptor subtypes are present differentially or otherwise over time on the inclusion membrane compared to cell membrane, and if so what their density and overall distribution is. Image analysis software will assist in these analyses.

Chronic disease sequelae from chlamydial infections involve primarily organisms in the persistent infection state, as in *Chlamydia*-induced inflammatory arthritis [25, 73, 81].

In order for NP-based therapy to be generally useful for treating chlamydial infections, it will preferably be effective again both normal active (primary) infections and persistent infections. We will assess expression from the α, β, and γ FAR in standard in vitro models of chlamydial persistence, including the normal human monocyte model utilized by inventors, and treatment of infected HEp-2 cells with low levels of IFN-γ and (separately) penicillin G. We also will assess FAR gene expression in the murine macrophage cell line RAW 264.7. Blood samples will be procured from volunteer donors, normal monocytes prepared, and infected at MOI of 1-5 [25,73]. In the normal monocyte model of infection, persistence is fully in force by 3 d post-infection.

Samples will be analyzed for transcripts from the FAR-encoding genes at 6, 24, 48, 72, and 96 hr post-infection in that model. Translation products will be assessed at the same time points by western analyses and IHC, as above, to insure that protein FAR protein levels are increased in some reasonable proportion to those of the encoding transcripts. As in studies above for normal active infection of human and mouse cells, FAR up-regulation will be examined in the monocyte model of persistence using K, E and C serovars.

Another model of persistence that has been well studied in many laboratories is that elicited by treatment of chlamydiae-infected HEp-2 cells with low levels of recombinant IFN-γ [82,83]. Persistence elicited by penicillin G has been somewhat less extensively studied, but recent results from APH's laboratory indicate that the transcript pattern of chlamydial cells in which persistence has been elicited by IFN-γ treatment vs penicillin G treatment are not entirely congruent [APH, manuscript in prep.; see also [72,84]]. In experiments parallel to those given just above for the normal monocyte model, we will elicit persistence in K, E and C serovar-infected HEp-2 cells and McCoy cells as extensively described by others, eg, [85]; we will assess FAR transcripts and translation products as a function of time post-infection. Time points to be examined include 4, 8, 14, 24, and 48 hr post-infection.

Extension to use of serovar E is reasonable because this is a very common STD serovar in the US, and has been used extensively by the inventors and others. Results for mRNA and protein analyses of FAR expression will be compared between the IFN-γ and penicillin G treated cultures, and both will be compared to results from the normal monocyte model of persistence.

Further experiments will extend the culture-based results to the mouse model of genital chlamydial infection. Female BALB/c mice will be infected genitally with K and E serovar in separate experiments, as extensively described by us [86, 87]. In additional experiments, BALB/c will be ocularly infected with C serovar [54]. Tissues will be procured at 1, 3, 7, 10 and 12 d post-infection for analysis to determine relative levels of mRNA from the three FAR-encoding genes, using real time RT-PCR as above. Western analyses also will be performed to assess translation product levels from those genes. Tissues to be so analyzed include the synovia, genital tracts, conjunctivae, and tissues in which nanoparticles initially accumulate such as liver, spleen or kidneys. Results from these analyses will be compared with those from the various in vitro model systems above.

The results will provide molecular background, and will provide a significant amount of new data regarding responses of the various host cell types to chlamydial infection. The results may also further demonstrate differences in host responses to ocular vs genital serovars of *C trachomatis*. These studies will distinguish between targeting inflamed, infected tissues and expected clearance via other tissues.

Example 18

Targeting of *Chlamydia*-Infected Cells by Folic Acid-Derivatized Nanoparticles Containing Antibiotics Data disclosed in the examples above strongly suggest that folic acid-conjugated PLGA particles labeled with 6-coumarin home to *C trachomatis*-containing inclusions at 24 hr and later post-infection in actively infected HEp-2 cells. It remains to be demonstrated, however, whether that homing will obtain at significant level at all times post-infection, whether homing will occur in cells harboring persistent chlamydiae, whether the efficacy of particle delivery is higher at one or more specific times post-infection, and whether it will occur at all/some times post-infection in epithelial cells (active) or monocytic cells (persistent) harboring *C trachomatis*.

To address these issues, fluorescently-labeled, folic acid conjugated PLGA particles will be added to cultured epithelial cells (HEp-2) and normal human monocytic cells and uptake will be assessed by fluorescence microscopy. In addition, using fluorescence microscopy, we will study the intracellular trafficking of nanoparticles in infected and uninfected cells to understand the mechanism of nanoparticle targeting to inclusions. Those data will be correlated with data from Example 17 regarding the relative level of upregulation of each folate receptor cell type in the various host cell types. If targeting is equivalent at all times examined for both serovars in all cell types examined, as we expect, we will prepare particles containing the antibiotics azithromycin and rifampin and determine the bactericidal and bacteriostatic activity in cell culture.

To be able effectively to target chlamydial inclusions, it is important to determine the times post-infection when the uptake of folate-conjugated nanoparticles is the highest. Further, it is also essential to demonstrate that host cells harboring persistent organisms take up targeted nanoparticles. HEp-2 cells will be infected with *C trachomatis* serovars K, E, or C in separate experiments, and nanoparticles will be added to the infected cells at 0 hr, 2 hrs, 6 hrs, 12 hrs, 18 hrs, 24 hrs, 36 hrs and 48 hrs post-infection; fluorescently-labeled nanoparticles will be used for the studies. Nanoparticles with folic acid, nanoparticles with just PEG and no folic acid, nanoparticles without PEG and folic acid will be used as treatments with the latter two nanoparticle types serving as controls. Cells will be imaged over a period of 60 min following nanoparticle addition, and uptake of the various particles into infected vs uninfected cells (and inclusions, see just below) will be correlated with temporal FAR expression during chlamydial infection from examples above.

In order to further confirm the effect of microbe's developmental stage on nanoparticle targeting to inclusions, we will quantify particle levels in the inclusion using HPLC. HEp-2 cells will be grown in 24 well plates and infected as before. Fluorescently-labeled nanoparticles will be added to the infected cells at 0 hr, 2 hrs, 6 hrs, 12 hrs, 18 hrs, 24 hrs, 36 hrs and 48 hrs post-infection. Cells will then be lysed and protein content of lysates determined using the Pierce protein assay kit.

The developmental stage of the microbe will be confirmed by determining the expression of specific genes known to be expressed at different stages of the developmental cycle. These will include but not be limited to early genes (eg, omp1, others), middle period genes (eg, pyk, dnaA, others), and late genes (eg, omcB, others) [see [88]]. Cell lysates will then be lyophilized and the fluorescent label will be extracted using methanol.

Nanoparticle concentration in the inclusions will be determined by HPLC. Increased nanoparticles uptake into cells may not reflect increased uptake into the inclusions. However, we expect that any increase in cellular uptake of nanoparticles following infection is due to FAR overexpression and a general increase in cellular uptake of nanoparticles will translate into increase in nanoparticle accumulation in inclusions. We will confirm the results of this study by quantitating the nanoparticles-associated fluorescence in inclusions using confocal microscopy.

Examples above indicated that folate-conjugated nanoparticles rapidly (<10 min) target chlamydial inclusions when added to infected host cells in culture (FIG. 12). However, the mechanism of this targeting is not known. We will investigate the intracellular trafficking of nanoparticles with and without conjugated folic acid in chlamydiae-infected cells. It is well established that chlamydial inclusions are neither acidified nor fusogenic with lysosomes. It has been shown that the inclusion, rather than interacting with the endocytic pathway, is fusogenic with exocytic vesicles containing sphingomyelin and cholesterol on their way from the Golgi apparatus to the plasma membrane [89-91].

While the question of whether there is any direct folic acid receptor-mediated endocytosis at the inclusion membrane is not yet answered, studies [29] suggest that there could be some overlap between the host folate receptor-mediated endocytosis and cholesterol transport. Folate receptors (α and β isoforms) belong to a special class of membrane proteins, namely glycosylphosphatidyliositol (GPI)-anchored proteins.

GPI-anchored proteins are trafficked differently from transmembrane-anchored proteins such as transferrin receptors. It has been shown that the trafficking of GPI-anchored proteins is regulated by cellular levels of cholesterol and sphingolipids. Further, GPI-anchored proteins are thought to be constituents of lateral nonhomogeneities in the exoplasmic leaflet of the plasma membrane termed as rafts.

While there is some disagreement in the literature on the role of the rafts in chlamydial entry into host cells (for example, [92]) Stuart et al showed that $C$ pneumoniae, $C$ psittaci, and $C$ trachomatis serovars E and F (but not serovars A, 36B, and C, LGV, L2 and MoPn) enter host cells via cholesterol-rich lipid raft microdomains [93]. Because the inclusions (organism) may use the rafts to derive cholesterol and sphingolipids [89, 93, 94], we expect nanoparticles to also use the same pathway to traffic to inclusions. To test this hypothesis, we will determine the effect of inhibition of cholesterol transport on nanoparticle trafficking to inclusions.

Fluorescently-labeled nanoparticles with and without folic acid will be administered to HEp-2 and normal human monocytes at various times post-infection and then visualized using the RTM-3 microscope under fluorescence mode and Richardson contrast mode to define the localization of nanoparticles inside the cells with reference to other organelles. The fluorescent label (6-coumarin) stays attached to nanoparticles and does not leach out in the time frame of the studies proposed here but control experiments will deliver 6 coumarin alone to infected cells to confirm this in the chlamydia infection models [38, 44, 95]. Images will be obtained at 5, 10, 15, 30 and 60 min post-nanoparticle addition. Initially, localization of nanoparticles within the endocytic pathway will be determined using markers for early endosomes and lysosomes.

Texas red-conjugated transferrin will be used as a marker for early endosomes while Lysotracker Blue will be used as a marker for acidic lysosomes. Presence of nanoparticles in these compartments will be determined by the colocalization of nanoparticle-associated green fluorescence with marker-associated red or blue fluorescence.

Following this, the ability of the LDL pathway to contribute to nanoparticle trafficking will be investigated. Cells will be incubated with nanoparticle suspension prepared in lipid-deficient serum in the presence of ammonium chloride to prevent the acidification of lysosomes [96]. If the LDL pathway contributes to trafficking of nanoparticles to inclusions, ammonium chloride is expected to reduce or prevent this trafficking. Finally, we will study the effect of Brefeldin A and nocodazole on nanoparticle trafficking to inclusions. Brefeldin A is a Golgi inhibitor while nocodazole inhibits microtubules. Previous studies [89] showed that both these inhibitors reduce cholesterol and sphingolipid accumulation in inclusions through the exocytic pathway. If nanoparticles use the same pathway to accumulate in inclusions, these inhibitors should reduce nanoparticle trafficking to inclusions if the inhibitors are added prior to incubation with nanoparticles.

The effect of above inhibitors on nanoparticle accumulation in the inclusions will be determined using fluorescence microscopy with image analysis as above. We will confirm the results of the microscopic studies by quantitation of nanoparticle levels in the inclusions following different treatments. EBs will be purified from treated cells by density gradient centrifugation and then extracted with methanol. The methanolic extract will be analyzed for 6-coumarin concentration by HPLC and the results will be expressed as the amount of nanoparticles per mg chlamydial protein. (see Methods); controls will be infected cells pulsed with nanoparticles and extracted directly for HPLC analysis. In an independent set of experiments, we will determine the effect of the above inhibitors (without nanoparticle treatment) on inclusion counts to confirm that these treatments do not affect chlamydial viability.

As discussed above, monotherapies with antibiotics such as azithromycin, doxycycline or rifampin are effective in eliminating acute (active) infections but are less effective against persistent forms. A few previous studies have shown that the combination of azithromycin and rifampin is effective against both *C trachomatis* and *C pneumoniae* [27,28]. In this example, we will determine the efficacy of azithromycin and rifampin combination administered in folic acid conjugated nanoparticles against persistent infection. We have already optimized the formulation conditions for loading the combination of azithromycin and rifampin in nanoparticles. Studies by others show that a combination of 0.5 μg/ml of azithromycin and 0.015 μg/ml of rifampin was effective in reducing *C trachomatis* serovar K infection in HEp-2 cells [97] while a combination of 0.1 μg/ml of azithromycin and 0.075 μg/ml of rifampin was effective against *C pneumoniae* in vitro [98]. Based on our initial studies above, we will use concentration ranges of 0.01 to 0.5 μg/ml of azithromycin and 0.001 to 0.1 μg/ml of rifampin in our studies.

Infected cells will be treated with nanoparticles loaded with both antibiotics, nanoparticles loaded with either antibiotic, empty nanoparticles, antibiotics in combination or separately dissolved in the medium or medium alone. Treatments will be tested on HEp-2 and normal monocytes for human models; for mouse cell models, we will use McCoy because they are good for drug titrations and RAW 264.7 cells. Loaded nanoparticles will be given at various times post-infection as determined above, allowed to home to the inclusions for 24-48 hr, then cultures will be harvested for determination of viable chlamydiae by i) real time PCR (APH lab) targeting the relative level of chlamydial chromosome relative to that of control cells (identically infected but given empty particles or no treatment), and recovery of IFU by titration of lysates on fresh indicator cells (JAW-H lab).

Example 19

Therapeutic Efficacy of Antibiotic-Loaded Nanoparticles In Vivo

Following infection at the epithelial surfaces of the urogenital system, C trachomatis can ascend to the upper reproductive tract, and then disseminate to distant anatomic locations such as the joint, to engender chronic inflammatory sequelae. Initial experiments suggested that folic-acid conjugated nanoparticles home to infected synovial tissues in a mouse model of C trachomatis-induced arthritis. Whole animal imaging study indicated that appropriately labeled folic acid-conjugated nanoparticles might be useful for imaging infection sites to monitor the progression or eradication of infection in addition to their use in drug delivery.

By a combination of in vivo imaging, molecular genetic, and other methods, we will extend these results to determine if delivery of antibiotic-loaded nanoparticles to Chlamydia-infected mice clears persistent synovial infection in vivo. We will define the host and pathogen responses to delivery of antibiotic loaded nanoparticles that reduce synovial chlamydial load after mucosal infection. We will determine if reduction in synovial chlamydial load correlates with localization of nanoparticles and reduced synovial inflammation, and whether nanoparticle-delivered therapy alters the articular/synovial persistent and/or acute infection.

We have obtained key molecular data that persistently infected cells are present in mouse knees after genital infection of mice with serovar K-EB. Because it is a more prevalent genital serovar than K, we will test E serovar in BALB/c and possibly C3H mice to confirm the observation. Next, antibiotic-treated mice will be compared to untreated controls (Table 1 below shows the different treatment groups). Treatments will be administered at a time point corresponding to maximal tissue folic acid expression observed above in Example 17.

Following treatment, animals will be euthanized at 48 h and later time points (a time course will be performed) and different tissues including the synovium, genital tract, and liver will be collected. Nucleic acids will be extracted from synovium of hind knees and other tissues from at least five mice per group. PCR will confirm that total chlamydial DNA (16S rRNA) is reduced after antibiotic treatment. cDNA will be prepared from RNA isolated from these groups using standard techniques and quantitative real time RT-PCR will be performed targeting genes whose expression/non-expression is characteristic of acute vs persistent chlamydial infection.

Initially we will use the genes for chlamydial cell division (eg, dnaA vs ftsW), but additional genes such as the differentially expressed Hsp60 genes will be targeted as additional genes/functions associated with persistence in human patients/cells are identified. The mouse arthritis model, based on adequate quantities of DNA and RNA can be extracted to perform the proposed studies. Opposite hind knees and paws will be used for histopathology in some experiments.

TABLE 1

Treatment groups

| Group # | Treatment | Purpose |
|---|---|---|
| 1 | Azithromycin + Rifampin NP – Targeted | To determine efficacy of targeted combination therapy |
| 2 | Azithromycin NP – Targeted | To determine efficacy of targeted mono therapy |
| 3 | Rifampin NP – Targeted | To determine efficacy of targeted mono therapy |
| 4 | Blank NP – Targeted | Control for groups 1 to 3 |
| 5 | Azithromycin + Rifampin NP – Non-targeted | Non-targeted control for group 1 |
| 6 | Azithromycin + Rifampin free in solution | Solution control for group 1 |
| 7 | Azithromycin free in solution | Solution control for group 2 |
| 8 | Rifampin free in solution | Solution control for group 3 |
| 9 | Vehicle | Untreated control |

We will determine whether reduced joint inflammation as well as chlamydial load are results of reduced acute and/or persistent genital tract infection vs reduced dissemination to joint vs active anti-chlamydial responses occurring within the joints. We will test whether there are fewer organisms in genital tract/conjunctivae (site of primary infection) following targeted antibiotic therapy based on chlamydial DNA/RNA. If reduced chlamydiae are detected in joints and genital tracts/conjunctivae of treated compared to non-treated mice, this will support reduced dissemination from genital tract.

If there are fewer acutely or persistently infected monocytes/DC in GT, joint protection would be attributed to an antibiotic therapy-induced reduction in total load and thereby reduction in persistently infected cells either at the level of the genital tract or during trafficking from genital tract. If there is no detectable change in GT load based on treatment but reduced knee pathology/load, we will conclude that local, intra-articular antimicrobial effects probably contribute to reduced arthritis most significantly (see below). Several time points will be tested initially (d. 4, 6, 8, 10 pi) using only the targeted combination therapy nanoparticles (Group 1; Table). Using the data obtained from the initial studies, we will narrow the window for testing of other groups as indicated in the Table.

Reduction of chlamydial load in synovium will be determined by screening PCR followed by real time PCR/RT-PCR on positive samples. We will establish a standard curve for chlamydial chromosome number and transcripts relative to IFU input from purified EB stock. Our hot phenol extraction methods allow for both DNA and RNA isolation. Given the smaller amount of total nucleic acids we can obtain from mouse synovium (average, 10 μg) we will limit our tests for the acute/persistence infection to assays for genes expected to be positive and negative as described earlier. If inter-mouse variability is low, we may pool either 2 knees/mouse or 2-4 knees/2-4 mice to allow a larger panel of genes to be tested by qPCR.

Synovial tissue, while not as complex as the genital tract, has some 'black box' features. For instance, in human reactive arthritis (ReA), it is not known whether the inflammation begins at the level of the synovial lining cells or at vessels from which activated, infected cells egress. Synovial macrophages have been shown by EM/IEM to harbor EB/RB-like particles by the JWH/APH collaborator HR Schumacher [10] and more recently HRS/APH showed IEM of aberrant RB in human synovium [99]. There is only one very early report of culture-positive samples from synovial fluid. It is now appreciated by most in the field that persistent chlamydial infection of reactive arthritis joints is a result of localization of cells/ monocytes harboring viable, metabolically active *C trachomatis* beneath the synovial lining cells [79].

We have shown previously that Th1 and Th2 cytokine expression is upregulated in synovial tissues from ReA mice, as was shown for human ReA synovium (JW-H, unpublished). Our preliminary studies with mouse synovium showed that genital infection resulted in upregulation of transcripts for IL-4, IL-10, IL-12 and TNFα, with lesser increases in IL-12 at the time point assessed (d 21 p.i.). We expect to detect downregulation of pro-inflammatory responses and clearing of infected cells in successfully treated mice.

The most direct method to test this possibility initially will be to use real time PCR/RT-PCR to assess key cytokine/chemokine transcript levels with respect to chlamydial DNA load with and without nanoparticle-mediated therapy. Knees from the treated mouse populations (treatments as in the Table) will be removed and either snap frozen for DNA/RNA extraction or, for some mice, synovium will be dissected from under the patella using a high-power dissecting microscope. The latter samples will be processed immediately for molecular and culture experiments, or snap-frozen until processing for NP extraction. Knees/paws from additional mice will be fixed for histologic studies.

An important strength of the model is that we have assessed the genital tract/joint axis in several mouse strains and currently we are expanding the chlamydial serovars tested. The window of biological relevance for events involving nanoparticle delivery to both genital tract and distant tissue can be narrowed quite simply. We will target knees at 10-21 days post-injection initially; earlier time points will be used if necessary. Such temporal studies are simply not possible in studies of patients with chlamydial STD±ReA, and studies of the dissemination stage via peripheral blood are limited in both animals and humans. Our proposed studies in the murine model offer novel ways to investigate effects of antibiotic therapy locally, in transit and at peripheral sites.

Further, we will determine if inflammatory response parameters are altered in the synovium of treated mice. We expect this to be the case, but such responses are unlikely to be detectable until after dissemination of chlamydia to joints. We will perform RT-PCR (conventional semi-quantitative PCR for selected cytokine/chemokines and then real time RT-PCR to maximize our quantitative information on these small samples). The combination of tests of host responses vs pathogen gene expression will provide important information regarding the relation of host responses to the replicative state of the bacteria within synovium and the effect of targeted antibiotic therapy on the host responses. This information has implications for future drug development for human ReA caused by chlamydia initially infecting mucosal tissues.

Nanoparticle Preparation.

Antibiotic loaded nanoparticles will be formulated using a modification of our previously published emulsion solvent evaporation technique [95]. In a typical procedure, antibiotics azithromycin and rifampin (16 mg each) along with the polymer PLGA (30 mg) are dissolved in 1 ml chloroform. This solution is added to 12 ml of aqueous 2% w/v polyvinyl alcohol solution and is sonicated using a probe sonicator (Misonix) to form water-in-oil emulsion. Precaution is taken to maintain the temperature of the emulsion around 4° C. during sonication in order to maintain the stability of antibiotics. The emulsion is stirred overnight to evaporate chloroform. Nanoparticles formed are recovered by ultracentrifugation (140,000×g), washed two times with distilled water to remove unentrapped antibiotics, and then lyophilized for 48 hrs.

Nanoparticles with Folic Acid on the Surface.

Figure 5B:
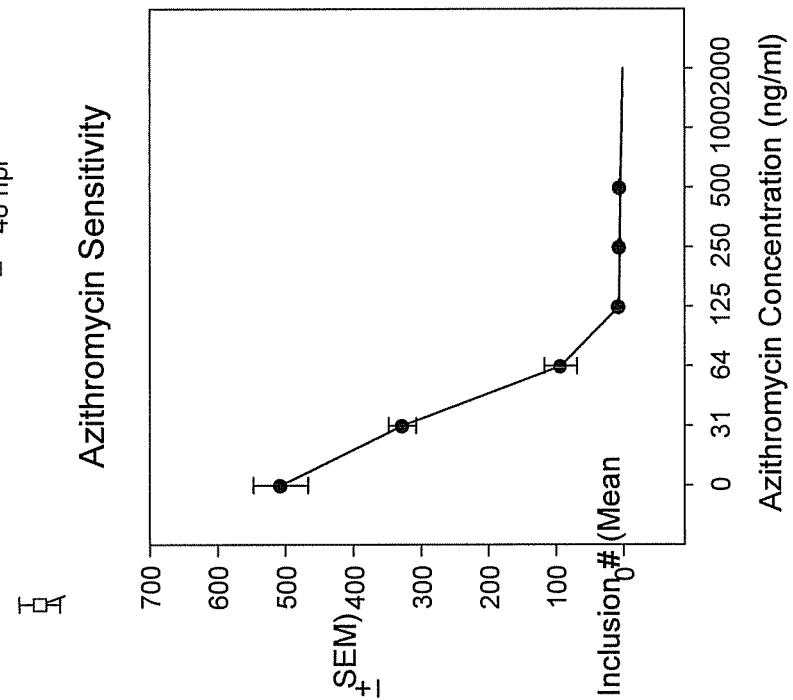
FIGS. 5A and 5B. McCoy cells infected with $10^4$ IFU/well *C. trachomatis* (serovar K), and treated immediately following infection with serial two-fold dilutions of azithromycin or rifampin to a final concentration range of 31-2000 ng/ml and 1-64 ng/ml, respectively, and incubated for 24 or 48 hrs. Both azithromycin and rifampin, showed no significant change in $MIC_{50}$ with length of treatment.
Figure 5A:
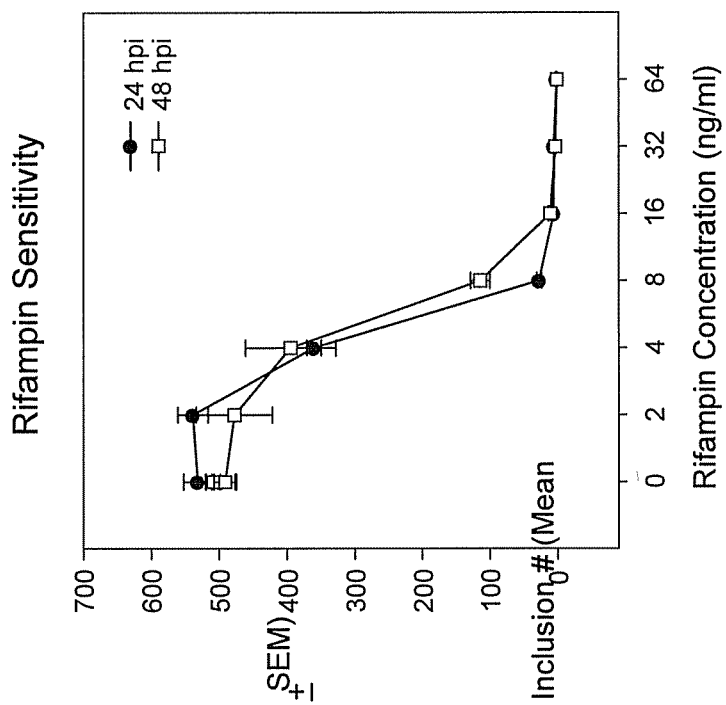

Following the preparation of emulsion in polyvinyl alcohol (see above), a methanol solution (100 μl) of polylactide (PLA)-PEG-folic acid conjugate is added to the emulsion. This results in the anchoring of the PLA segments into nanoparticles, with PEG-folic acid chains on the surface. Following this, the emulsion is stirred to evaporate organic solvents and nanoparticles are processed as described above. This procedure was used in the Preliminary Studies to obtain nanoparticles containing PEG-folic acid conjugate on the surface (FIGS. 3-5).

Nanoparticle Characterization.

To quantitate antibiotic loading, nanoparticles will be incubated with methanol for 8 hrs, and the concentration of azithromycin and rifampin in methanol extract will be determined by HPLC. For azithromycin, a Beckman HPLC system consisting of C-18 column (Beckman) heated at 50° C. and UV detection (210 nm) will be used for drug quantification. Two mobile phases (Mobile phase A: Phosphate buffer pH 8.5: Methanol (90:10) and Mobile Phase B: Acetonitrile: Methanol (90:10)) in the ratio of 25:75 will be used at a flow rate of 1 ml/min. For rifampin, a similar HPLC setup and column conditions will be used. Mobile phase consisting of phosphate buffer (pH 6.8) and acetonitrile (50:50) and UV detection (238 nm) will be used. To determine the release of antibiotics, nanoparticles (1 mg/ml) will be suspended in PBS (pH 7.4; 0.15 M) containing 0.1% Tween 80 (to maintain sink conditions), and kept at 37° C. and 100 rpm. Antibiotic concentration in the release buffer will be determined by HPLC.

Nanoparticles that release different doses of antibiotics will be formulated by varying the dose-ratios of antibiotics in the formulation and by using polymers of different molecular weights and hydrophobicity. PLGA polymers of different molecular weights and composition are available commercially (Birmingham Polymers). Particle size and size distribution of nanoparticles will be determined by dynamic light scattering (DLS) and atomic force microscopy (AFM). For DLS studies, a suspension of nanoparticles (1 mg/ml) will be subjected to particle size analysis in 90Plus particle size analyzer (Brookhaven). For AFM studies, a suspension of nanoparticles (1 mg/ml) will be added to silicon substrate that is pre-coated with polyethyleneimine, and air-dried. AFM images will be obtained with an E scanner (Nanoscope III, VEECO).

Determination of Nanoparticle Concentration in Cells and Organelles.

Nanoparticle concentration in cell or organelle lysates will be determined using our previously published HPLC assay procedures (REF). Lysates will be initially lyophilized to maximize the extraction efficiency. Following this, 1 ml methanol will be added to the lyophilized samples and incubated for 6 hr. Concentration of the fluorescent label, 6 coumarin, will be determined using HPLC. A C-18 column (4.6 mm×25 cm) with 5 um (fix micron) packing (Beckman) will be used. Separations will be achieved using acetonitrile:water:1-heptane sulfonic acid sodium salt (65:35:0.005M) as the mobile phase. 6-coumarin will be quantified using a fluorescence detector (Jasco; $\lambda$(Ex) 450 nm/$\lambda$(Em) 490 nm). Concentration of nanoparticles will be determined from a standard curve of peak area versus nanoparticle concentration, and the results expressed as amount of nanoparticles normalized to cell protein.

Infection of Cell Lines and Primary Monocytes Cultures.

Various cell lines will be used. In most cases, McCoy (mouse) or HEp2 (human) cells will be infected. The former will be used for titrations of chlamydial stocks and for drug dose-response assays. Cells will be infected with an MOI ~1 in 96 well plates. Plates will be centrifuged at RT for 1 hr (1200×g), incubated at 37 C for 1 hr, then overlay medium containing 0.5-1.0 ug/ml cycloheximide applied; for antibiotic titrations, antibiotics will be added to overlay medium.

Genital or Conjunctival Chlamydial Infection of Mice [54, 67, 100].

Mice are DepoProvera treated prior to challenge with human biovars of C trachomatis. Serovars K and E are currently in use as genital challenge inocula; C serovar will be used for ocular (conjunctival) infection. These and other chlamydial stocks are grown and Percoll purified in the JWH laboratory. Challenge doses usually are $5 \times 10^6 – 10^7$ IFU delivered topically intravaginally in 30 µl SPG; for ocular challenge, 5000 IFU (~$5 \times 10^6$ IFU) are topically delivered in 5 µl to each eye. High-titered crude stocks are used in some experiments. Vaginal or conjunctival swabs are collected for culture and DFA at weekly intervals until the end of each experiment.

Uninfected mice kept in separate filter-top cages will be examined and swabbed on the same schedule to control for nonspecific effects of procedures. After swab sample collections, samples are randomized and then coded; the code is only broken by the PI after results are obtained.

Specimen Collection.

Genital tracts (GT and Conjunctivae) are dissected out using sterile technique and new instruments for each tissue per mouse. For histopathology combined with culture or molecular analyses GT is divided into ovary/oviduct/upper one-third of uterine horn (R1/L1); mid-uterine horn (R2/L2); lower horn with cervix/vagina (R3/L3). The cervix/vagina is divided at the bifurcation of the horns (one half for molecular study, the other embedded for histology) for snap freezing (molecular analysis) or OCT embedding. For confirmation of NP targeting, half of the GT or one conjunctival sample will be frozen for extraction and HPLC analysis of 6-coumarin. Tracts are photographed in situ as well as ex vivo for documentation of vaccine effects to correlate with histology, with mouse number included in each image. Signs of inflammation are scored at the time of sacrifice based on edema, vascularity, overt inflammation (color change). DepoProvera treated uninfected mice are included as controls in all experiments. Conjunctivae are obtained as we published [54]; hormone treatment is not needed.

Knees/Synovium.

After sacrifice by exsanguinations, hind legs are removed aseptically after removing skin from hind legs. One knee is generally snap frozen for sterile harvesting of synovium, and the other hind leg is formalin fixed. In some experiments, synovium will be dissected on fresh tissues under a binocular microscope. This tissue would be snap embedded in OCT for histology, or snap frozen for biochemical and/or molecular analyses. Since samples are so small, synovium from both hind legs would be collected and pooled for this purpose. Paws/ankles will be processed separately—these are often the first joints inflamed in other rodent arthritis models. These methods are published [67,100]. Selected tissues will be collected to determine loads of NP (based on extraction of 6-coumarin), homing of NP to inflamed tissues vs to expected routes of clearance; tissues may include spleen, liver, lungs, kidneys, genital tracts/conjunctivae and joints.

Microbiologic Assays.

Culture/DFA will be performed from genital or conjunctival swabs by standard methods. Inclusions are graded on a 0-4+ scale on a fluorescent microscope; mean inclusion counts/ml for each mouse are calculated from first passage samples in duplicate 96 wells. DFA smears are processed as for monkeys or humans except a minimum of 200 cells will be used for conjunctival smears and total EB scored (0-4+ scale) for each smear. Antibiotic dose-response curves will be generated with infected McCoy or other susceptible cells for each preparation of drug-loaded NP to ensure expected loading prior to delivery in vitro or in vivo. Molecular screening for chlamydial DNA will be used regularly as proposed under the specific aims and in our published studies. Chlamydia-specific antibodies are commercially available [54, 87, 100, 101].

Molecular and Cellular Assays.

Extraction and purification of DNA and RNA will be by standard methods using hot phenol or Trizol [102, 103]. We routinely prepare RNA from small samples of murine tissues and cells, including mouse synovium. Particular care is taken to avoid cross-contamination of samples with chlamydial DNA/RNA; animal dissections, nucleic acid extractions, and molecular assays are each performed in different rooms. The hoods used for RT reactions are not used for assays involving intact or live chlamydia; indeed, those hoods are in separate buildings. Standard negative controls are included in assays to document integrity of samples and absence of chlamydial/other DNA.

RT-PCR will be used in some experiments to detect cytokine mRNA in mouse genital tissues, conjunctivae and LN under different experimental conditions; the co-PI has published the methodology to be used [67, 104-107] Quantitative real time RT-PCR (qPCR) is in use in the co-PI's and co-I's labs for both chlamydial and host gene expression [25, 73, 74, 108, 109] (see Biosketches); cDNA obtained by RT reactions with random hexamer primers are used for q-PCR reactions on either the Applied Biosystems 7700 or Roche Light Cycler using SybrGreen for product detection. There is also a new Applied Biosystems 7500 instrument in the co-I's laboratory. All primers for qPCR for chlamydial genes have been (re) designed for use with mouse tissues/cells guided by the primers used in our human studies; preliminary tests have determined that no products are seen when chlamydia-specific primers are used for uninfected mouse cells.

Immunohistochemical Staining.

ABC immunoperoxidase or fluorescent antibody staining is used for detection of cellular and chlamydial antigens and cytokines. Antibodies to molecules of interest are available commercially or through ATCC. Immunohistochemical analyses of surface antigens and receptors, and cytokines in tissue sections and single cell preparations are published [105, 110]. Molecular Probe bioprobes will be used for dual staining under wavelengths using living cells on the RTM-3 microscope. Additional experiments will use a Nikon E600 epifluorescence microscope with appropriate filters to analyze co-expression; results will be documented by digital photography and analyzed with ImagePro software in the PI's lab.

Real time microscopy will also be performed with the RTM3 microscope to test how infected target cells respond to various antibiotic delivery approaches. These images will be digitally captured on DVC tape and in Volocity (Improvision Inc) software (Mac G4 platform) customized for the RTM-3; heated perfusion chambers will allow longer term experiments and time lapse photography documentation.

EM/IEM.

EM/IEM analyses are used to extend our observations in synovium, and to identify cells containing organism, and the state of the organism (classical or aberrant forms).

Statistical Analyses.

Relative transcript levels will be compared by treatment±infection after chlamydial and host values are normalized to 16S rRNA and 18S rRNA, respectively. ANOVA will be used to compare results from different treatment groups. Student's t-test will be used to compare differences between treatment groups (chlamydial titers). Gene expression differences between treatment groups will be analyzed by Kruskal-Wallis one-way ANOVA on ranks, with multiple comparisons of groups done by Student-Newman-Keuls method. Repeated measures ANOVA will be used for in vivo time-course experiments.

REFERENCES

1. Abu el-Asrar, A. M., Geboes, K., Tabbara, K. F., al Kharashi, S. A., Missotten, L. and Desmet, V. (1998) Immunopathogenesis of conjunctival scarring in trachoma. *Eye*, 12, 453-460.
2. Heggie, A. D., Lass, J. H., Albert, D. M. and Jakobiec, F. A. (1994) *Principles and practice of ophthalmology: Basic sciences*. Saunders, Philadelphia.
3. (2002) CDC and Prevention. Screening tests to detect *C trachomatis* and *N gonorreheae* infections-2002. *MMWR*, 51, 1-3.
4. Ho, J. L., He, S. H., Hu, A. R., Geng, J. Y., Basile, F. G., Almeida, M. G. B., Saito, A. Y., Laurence, J. and Johnson, W. D. (1995) Neutrophils from human HIV-seronegative donors induce HIV replication from HIV-infected patients mononuclear cells and cell lines—an in vitro model of HIV transmission facilitated by *Chlamydia trachomatis JEM*, 181, 1493-1505.
5. Honey, E. and Templeton, A. (2002) Prevention of pelvic inflammatory disease by the control of *C. trachomatis* infection. *Int. J. Gynaecol. Obstet.*, 78, 257.
6. Wiesenfeld, H. C., Hillier, S. L., Krohn, M. A., Amortegui, A. J., Heine, R. P., Landers, D. V. and Sweet, R. L. (2002) Lower genital tract infection and endometritis: insight into subclinical pelvic inflammatory disease. Obstet *Gynecol*, 100, 456-63.
7. Schachter, J., Stephens, R. S., Timms, P., Kuo, C., Bavoil, P. M., Birkelund, S., Boman, J., Caldwell, H., Campbell, L. A., Chemesky, M., Christiansen, G., Clarke, I. N., Gaydos, C., Grayston, J. T., Hackstadt, T., Hsia, R., Kaltenboeck, B., Leinormen, M., Ocjius, D., McClarty, G., Orfila, J., Peeling, R., Puolakkainen, M., Quinn, T. C., Rank, R. G., Raulston, J., Ridgeway, G. L., Saikku, P., Stamm, W. E., Taylor-Robinson, D. T., Wang, S. P. and Wyrick, P. B. (2001) Radical changes to chlamydial taxonomy are not necessary just yet. 51, 249, 251-249, 253.
8. Rapoza, P. A., Quinn, T. C., Kiessling, L. A. and Taylor, H. R. (1986) Epidemiology of neonatal conjunctivitis. *Ophthalmology*, 93, 456-61.
9. Branigan, P. J., G rard, H. C., Schumacher, H. R. and Hudson, A. P. (1997) Presence of *Chlamydia trachomatis* in circulating monocytes from the blood of patients with reactive arthritis/Reiter's syndrome. *Arthritis Rheumat*.
10. Schumacher, H. R., Jr., Magge, S., Cherian, P. V., Sleckman, J., Rothfuss, S., Clayburne, G. and Sieck, M. (1988) Light and electron microscopic studies on the synovial membrane in Reiter's syndrome. Immunocytochemical identification of chlamydial antigen in patients with early disease. *Arthritis Rheum*, 31, 937-46.
11. Saikku, P. (1997) *Chlamydia pneumoniae* and atherosclerosis—an update. *Scand J Infect Dis Suppl*, 104, 53-6.
12. Wong, Y. K., Gallagher, P. J. and Ward, M. E. (1999) *Chlamydia pneumoniae* and atherosclerosis. *Heart*, 81, 232-8.
13. Balin, B. J., G rard, H. C., Arking, E. J., Appelt, D. M., Branigan, P. J., Abrams, J. T., Whittum-Hudson, J. A. and Hudson, A. P. (1998) Identification and localization of *Chlamydia pneumoniae* in the Alzheimer's brain. *Med Microbiol Immunol (Berl)*, 187, 23-42.
14. Mahony, J., Woulfe, J., Munoz, D., Chong, S., Browning, D. and Smieja, M. (2000) *Chlamydia pneumoniae* in the Alzheimer's brain—is DNA detection hampered by low copy number? *Proc. Fourth Eur. Chlamydia Research Meeting*, August 2000, 4, 275.
15. Sriram, S., Mitchell, W. and Stratton, C. (1998) Multiple sclerosis associated with *Chlamydia pneumoniae* infection of the CNS. *Neurology*, 50, 571-2.
16. Grimes, J. E. and Wyrick, P. B. (1995) Chlamydiosis (Ornithosis). In *Diseases of Poultry*, pp. 311-325.
17. Henry, C. H., Hughes, C. V., Gerard, H. C., Hudson, A. P. and Wolford, L. M. (2000) Reactive arthritis: preliminary microbiologic analysis of the human temporomandibular joint. *J Oral Maxillofac. Surg.*, 58, 1137-1142.
18. Ossewaarde, J. M., Gielis-Proper, S. K., Meijer, A. and Roholl, P. J. M. (2000) *Chlamydia pneumoniae* antigens are present in the brains of Alzheimer's patients, but not in the brains of patients with other dementias. *Proc. Fourth Eur. Chlamydia Research Meeting*, August 2000, 4, 284.
19. Wyrick, P. B. and Raulston, J. E. (1999) Chlamydiae: Genital, ocular, and respiratory pathogens. In Schaechter, M., Engleberg, N. C., Eisenstein, B. I. and Medoff, G. (eds.), *Mechanisms of Microbial Disease*. Lippincott Williams & Wilkins, Philadelphia, vol. 3, pp. 261-267.
20. Hatch, T. P. (1999) In Stephens, R. S. (ed.), *Chlamydia—Intracellular biology, Pathogenesis, and Immunity*. ASM Press, Washington D.C., pp. 29-67.
21. Moazed, T. C., Kuo, C. C., Grayston, J. T. and Campbell, L. A. (1998) Evidence of systemic dissemination of *Chlamydia pneumoniae* via macrophages in the mouse. *J. Infect. Dis.*, 177, 1322-1325.
22. Villareal, C., Whittum-Hudson, J. A. and Hudson, A. P. (2002) Persistent Chlamydiae and chronic arthritis. *Arthritis Res*, 4, 5-9.
23. Hogan, R. J., Mathews, S. A., Mukhopadhyay, S., Summersgill, J. T. and Timms, P. (2004) Chlamydial persistence: beyond the biphasic paradigm. *Infect Immun*, 72, 1843-55.
24. Byrne, G. I. (2001) Chlamydial treatment failures: a persistent problem? *J Eur Acad Dermatol Venereol*, 15, 381.
25. Gerard, H. C., Krausse-Opatz, B., Wang, Z., Rudy, D., Rao, J. P., Zeidler, H., Schumacher, H. R., Whittum-Hudson, J. A., Kohler, L. and Hudson, A. P. (2001) Expression of *Chlamydia trachomatis* genes encoding products required for DNA synthesis and cell division during active versus persistent infection. *Mol. Microbiol*, 41, 731-741.
26. Gerard, H. C., Kohler, L., Branigan, P. J., Zeidler, H., Schumacher, H. R. and Hudson, A. P. (1998) Viability and gene expression in *Chlamydia trachomatis* during persistent infection of cultured human monocytes. *Med. Microbiol Immunol (Berl)*, 187, 115-120.
27. Tobin, J. M., Harindra, V. and Mani, R. (2004) Which treatment for genital tract *Chlamydia trachomatis* infection? *Int J STD AIDS*, 15, 737-9.
28. Carter, J. D., Valeriano, J. and Vasey, F. B. (2004) Doxycycline versus doxycycline and rifampin in undifferentiated spondyloarthropathy, with special reference to *chlamydia*-induced arthritis. A prospective, randomized 9-month comparison. *J. Rheumatol.*, 31, 1973-1980.
29. Sabharanjak, S, and Mayor, S. (2004) Folate receptor endocytosis and trafficking. *Adv Drug Deliv Rev*, 56, 1099-109.
30. Salazar, M. D. and Ratnam, M. (2007) The folate receptor: what does it promise in tissue-targeted therapeutics? Cancer Metastasis Rev, 26, 141-52.

31. Low, P. S., Henne, W. A. and Doorneweerd, D. D. (2008) Discovery and development of folic-Acid-based receptor targeting for imaging and therapy of cancer and inflammatory diseases. *Acc Chem Res*, 41, 120-9.
32. Nakashima-Matsushita, N., Homma, T., Yu, S., Matsuda, T., Sunahara, N., Nakamura, T., Tsukano, M., Ratnam, M. and Matsuyama, T. (1999) Selective expression of folate receptor beta and its possible role in methotrexate transport in synovial macrophages from patients with rheumatoid arthritis. *Arthritis Rheum*, 42, 1609-16.
33. Hilgenbrink, A. R. and Low, P. S. (2005) Folate receptor-mediated drug targeting: from therapeutics to diagnostics. *J Pharm Sci*, 94, 2135-46.
34. Lee, R. J. and Low, P. S. (1994) Delivery of liposomes into cultured KB cells via folate receptor-mediated endocytosis. *J Biol Chem*, 269, 3198-204.
35. Zheng, G., Chen, J., L1, H. and Glickson, J. D. (2005) Rerouting lipoprotein nanoparticles to selected alternate receptors for the targeted delivery of cancer diagnostic and therapeutic agents. *Proc Natl Acad Sci USA*, 102, 17757-62.
36. Panyam, J. and Labhasetwar, V. (2003) Biodegradable nanoparticles for drug and gene delivery to cells and tissue. *Adv Drug Deliv Rev*, 55, 329-47.
37. Vasir, J. K. and Labhasetwar, V. (2006) Polymeric nanoparticles for gene delivery. *Expert Opin Drug Deliv*, 3, 325-44.
38. Panyam, J., Sahoo, S. K., Prabha, S., Bargar, T. and Labhasetwar, V. (2003) Fluorescence and electron microscopy probes for cellular and tissue uptake of poly(D,L-lactide-co-glycolide) nanoparticles. *Int J Pharm*, 262, 1-11.
39. Panyam, J., Lof, J., O'Leary, E. and Labhasetwar, V. (2002) Efficiency of Dispatch and Infiltrator cardiac infusion catheters in arterial localization of nanoparticles in a porcine coronary model of restenosis. *J Drug Target*, 10, 515-23.
40. Panyam, J., Williams, D., Dash, A., Leslie-Pelecky, D. and Labhasetwar, V. (2004) Solid-state solubility influences encapsulation and release of hydrophobic drugs from PLGA/PLA nanoparticles. J Pharm Sci, 93, 1804-14.
41. Prabha, S., Zhou, W. Z., Panyam, J. and Labhasetwar, V. (2002) Size-dependency of nanoparticle-mediated gene transfection: studies with fractionated nanoparticles. *Int J Pharm*, 244, 105-15.
42. Panyam, J. and Labhasetwar, V. (2004) Sustained cytoplasmic delivery of drugs with intracellular receptors using biodegradable nanoparticles. *Mol Pharm*, 1, 77-84.
43. Prabha, S, and Labhasetwar, V. (2004) Critical determinants in PLGA/PLA nanoparticle-mediated gene expression. *Pharm Res*, 21, 354-64.
44. Panyam, J. and Labhasetwar, V. (2003) Dynamics of endocytosis and exocytosis of poly(D,L-lactide-co-glycolide) nanoparticles in vascular smooth muscle cells. *Pharm Res*, 20, 212-20.
45. Prabha, S, and Labhasetwar, V. (2004) Nanoparticle-mediated wild-type p53 gene delivery results in sustained antiproliferative activity in breast cancer cells. *Mol Pharm*, 1, 211-219.
46. Darville, T., Andrews, C. W., Jr., Sikes, J. D., Fraley, P. L. and Rank, R. G. (2001) Early local cytokine profiles in strains of mice with different outcomes from chlamydial genital tract infection. *Infect Immun*, 69, 3556-3561.
47. Hawkins, R. A., Rank, R. G. and Kelly, K. A. (2002) A *Chlamydia trachomatis*-specific Th2 clone does not provide protection against a genital infection and displays reduced trafficking to the infected genital mucosa. *Infect Immun.*, 70, 5132-5139.
48. Kelly, K. A. (2003) Cellular immunity and *Chlamydia* genital infection: induction, recruitment, and effector mechanisms. *Int. Rev. Immunol*, 22, 3-41.
49. Morrison, R. P., Feilzer, K. and Tumas, D. B. (1996) Gene knockout mice establish a primary protective role for major histocompatibility complex class ii-restricted responses in *chlamydia trachomatis* genital tract infection. *Infection and Immunity*, 63, 4661-4668.
50. Rank, R. G., Bowlin, A. K. and Kelly, K. A. (2000) Characterization of lymphocyte response in the female genital tract during ascending Chlamydial genital infection in the guinea pig model. *Infect Immun*, 68, 5293-8.
51. Rank, R. G. and Sanders, M. M. (1992) Pathogenesis of endometritis and salpingitis in a guinea pig model of chlamydial genital infection. *Am J Pathol*, 140, 927-36.
52. Rank, R. G. and Whittum-Hudson, J. A. (1994) Animal models for ocular infections. *Methods Enzymol*, 235, 69-83.
53. Van Voorhis, W. C., Barrett, L. K., Sweeney, Y. T., Kuo, C. C. and Patton, D. L. (1997) Repeated *Chlamydia trachomatis* infection of Macaca nemestrina fallopian tubes produces a Th1-like cytokine response associated with fibrosis and scarring. *Infect Immun*, 65, 2175-82.
54. Whittum-Hudson, J. A., O'Brien, T. P. and Prendergast, R. A. (1995) Murine model of ocular infection by a human biovar of *Chlamydia trachomatis. Invest Opthalmol V is Sci*, 36, 1976-87.
55. Rank, R. G., Dascher, C., Bowlin, A. K. and Bavoil, P. M. (1995) Systemic immunization with Hsp60 alters the development of chlamydial ocular disease. *Invest Opthalmol Vis Sci*, 36, 1344-51.
56. Rank, R. G., Sanders, M. M. and Kidd, A. T. (1993) Influence of the estrous cycle on the development of upper genital tract pathology as a result of chlamydial infection in the guinea pig model of pelvic inflammatory disease. *Am J Pathol*, 142, 1291-6.
57. Barron, A. L., Rank, R. G. and Moses, E. B. (1984) Immune response in mice infected in the genital tract with mouse pneumonitis agent (*Chlamydia trachomatis* biovar). *Infection and Immunity*, 44, 82-85.
58. Cain, T. K. and Rank, R. G. (1995) Local Th1-like responses are induced by intravaginal infection of mice with the mouse pneumonitis biovar of *Chlamydia trachomatis Infection and Immunity*, 63, 516-521.
59. de la Maza, L. M., Pal, S., Khamesipour, A. and Peterson, E. M. (1994) Intravaginal inoculation of mice with the *Chlamydia trachomatis* mouse pneumonitis biovar results in infertility. *Infection and Immunity*, 62, 2094-2097.
60. Morrison, S. G., Su, H., Caldwell, H. D. and Morrison, R. P. (2000) Immunity to murine *chlamydia trachomatis* genital tract reinfection involves B cells and CD4(+) T cells but not CD8(+) T cells [In Process Citation]. *Infect Immun*, 68, 6979-6987.
61. Murdin, A. D., Su, H., Manning, D. S., Klein, M. H., Parnell, M. J. and Caldwell, H. D. (1993) A poliovirus hybrid expressing a neutralization epitope from the major outer membrane protein of *Chlamydia trachomatis* is highly immunogenic. *Infection and Immunity*, 61, 4406-4414.
62. Pal, S., Fielder, T. J., Peterson, E. M. and de la Maza, L. M. (1993) Analysis of the immune response in mice following intrauterine infection with the *Chlamydia trachomatis* mouse pneumonitis biovar. *Infection and Immunity*, 61, 772-776.

63. Perry, L. L., Feilzer, K., Hughes, S, and Caldwell, H. D. (1999) Clearance of *Chlamydia trachomatis* from the murine genital mucosa does not require perforin-mediated cytolysis or Fas-mediated apoptosis. *Infection & Immunity.*, 67, 1379-1385.
64. Akbar, T. M., MacDonald, A. B., Giammalvo, J. T., Orfila, J., Byrne, G. I., Chemesky, M. A., Grayston, J. T., Jones, R. B., Ridgway, G. L., Saikku, P., Schachter, J., Stamm, W. E. and Stephens, R. S. (1994) Ascending genital tract infection in C3H/HeJ mice as a result of intravaginal inoculation with serovar F of *Chlamydia trachomatis*. In *Chlamydial infections: Proceedings of the 8th International Symposium on Human Chlamydial Infections*. Societa Editrice Esculapio, Bologna, Italy, pp. 541-544.
65. Darville, T., Andrews, C. W., Laffoon, K. K., Shymasani, W., Kishen, L. R. and Rank, R. G. (1997) Mouse strain-dependent variation in the course and outcome of chlamydial genital tract infection is associated with differences in host response. *Infect Immun*, 65, 3065-3073.
66. Stagg, A. J., Tuffrey, M., Woods, C., Wunderink, E. and Knight, S. C. (1998) Protection against ascending infection of the genital tract by *Chlamydia trachomatis* is associated with recruitment of major histocompatibility complex class II antigen-presenting cells into uterine tissue. *Infect Immun*, 66, 3535-44.
67. Whittum-Hudson, J. A., Gerard, H. C., Clayburne, G., Schumacher, H. R. and Hudson, A. P. (1999) A non-invasive murine model of chlamydia-induced reactive arthritis. *Rev Rhum Engl Ed*, 66, 50S-55S; discussion 56S.
68. Hough, A. J., Jr. and Rank, R. G. (1988) Induction of arthritis in C57B1/6 mice by chlamydial antigen. Effect of prior immunization or infection. *Am. J. Pathol.*, 130, 163-172.
69. Gerard, H. C., Lu, L., Schumacher, H. R., Clayburne, G., Whittum-Hudson, J. A., Rank, R. G. and Hudson, A. P. (1999) Time course and pathologic consequences of dissemination of *Chlamydia* to the joint following genital infection in a guinea pig model of reactive arthritis. *ASM Abstracts* 1999 *National Meeting*, 53-53.
70. Beatty, W. L., Byrne, G. I. and Morrison, R. P. (1993) Morphologic and antigenic characterization of interferon-gamma-mediated persistent *Chlamydia trachomatis* infection in vitro *Proc. Natl. Acad. Sci. U.S.A.*, 90, 3998-4002.
71. Rasmussen, S. J., Timms, P., Beatty, P. R. and Stephens, R. S. (1996) Cytotoxic-T-lymphocyte-mediated cytolysis of L cells persistently infected with *Chlamydia* spp. *Infect Immun*, 64, 1944-9.
72. Belland, R. J., Nelson, D. E., Virok, D., Crane, D. D., Hogan, D., Sturdevant, D., Beatty, W. L. and Caldwell, H. D. (2003) Transcriptome analysis of chlamydial growth during IFN-gamma-mediated persistence and reactivation. *Proc. Natl. Acad. Sci. U.S.A.*, 100, 15971-15976.
73. Gerard, H. C., Freise, J., Wang, Z., Roberts, G., Rudy, D., Opatz, B., Kohler, L., Zeidler, H., Schumacher, H. R., Whittum-Hudson, J. A. and Hudson, A. P. (2002) *Chlamydia trachomatis* genes whose products are related to energy metabolism are expressed differentially in active vs. persistent infection. *Microbes and Infection*, 4, 13-22.
74. Gerard, H. C., Whittum-Hudson, J. A., Schumacher, H. R. and Hudson, A. P. (2004) Differential expression of three *Chlamydia trachomatis* hsp60-encoding genes in active vs persistent infection. *Microb. Pathog.*, 36, 35-39.
75. Gerard, H. C., Whittum-Hudson, J. A. and Hudson, A. P. (1997) Genes required for assembly and function of the protein synthetic system in *Chlamydia trachomatis* are expressed early in elementary to reticulate body transformation. *Mol. Gen. Genet.*, 255, 637-642.
76. Branigan, P. J., G rard, H. C., Saaibi, D. L., Williams, W. V., Pando, J. A., Hudson, A. P. and Schumacher, H. R. (1996) Comparison of synovial tissue and synovial fluid as source of nucleic acids for detection of *Chlamydia trachomatis* by polymerase chain reaction. *Arthritis Rheumat.*, 39, 1740-1746.
77. Bas, S., Griffais, R., Kvien, T. K., Glennas, A., Melby, K. and Vischer, T. L. (1995) Amplification of plasmid and chromosome *Chlamydia* DNA in synovial fluid of patients with reactive arthritis and undifferentiated seronegative oligoarthropathies. *Arthritis Rheum.*, 38, 1005-1013.
78. Nicholson, T. L., Olinger, L., Chong, K., Schoolnik, G. and Stephens, R. S. (2003) Global stage-specific gene regulation during the developmental cycle of *Chlamydia trachomatis. J. Bacteriol.*, 185, 3179-3189.
79. Inman, R. D., Whittum-Hudson, J. A., Schumacher, H. R. and Hudson, A. P. (2000) *Chlamydia* and associated arthritis. *Curr. Opin. Rheumatol.*, 12, 254-262.
80. Caldwell, H. D., Wood, H., Crane, D., Bailey, R., Jones, R. B., Mabey, D., Maclean, I., Mohammed, Z., Peeling, R., Roshick, C., Schachter, J., Solomon, A. W., Stamm, W. E., Suchland, R. J., Taylor, L., West, S. K., Quinn, T. C., Belland, R. J. and McClarty, G. (2003) Polymorphisms in *Chlamydia trachomatis* tryptophan synthase genes differentiate between genital and ocular isolates. *Journal of Clinical Investigation*, 111, 1757.
81. Gerard, N. C., Branigan, P. J., Schumacher, H. R. and Hudson, A. P. (1998) Synovial *Chlamydia trachomatis* in patients with reactive arthritis/Reiter's syndrome are viable but show aberrant gene expression [see comments]. *J. Rheumatol.*, 25, 734-742.
82. Beatty, W. L., Morrison, R. P. and Byrne, G. I. (1994) Persistent chlamydiae: from cell culture to a paradigm for chlamydial pathogenesis. *Microbiological Reviews*, 58, 686-699.
83. Byrne, G. I., Carlin, J. M., Merkert, T. P. and Arter, D. L. (1989) Long-term effects of gamma interferon on chlamydia-infected host cells: microbicidal activity follows microbistasis. Infect Immun, 57, 1318-1320.
84. Borel, N., Mukhopadhyay, S., Kaiser, C., Sullivan, E. D., Miller, R. D., Timms, P., Summersgill, J. T., Ramirez, J. A. and Pospischil, A. (2006) Tissue MicroArray (TMA) analysis of normal and persistent Chlamydophila *pneumoniae* infection. *BMC Infect Dis*, 6, 152.
85. Schramm, N., Bagnell, C. R. and Wyrick, P. B. (1996) Vesicles containing *Chlamydia trachomatis* serovar L2 remain above pH 6 within HEC-1B cells. 64, 1208-1214.
86. Whittum-Hudson, J., Davis, E., Vora, G., Kuo, P., Schumacher, H. R., Stuart, E. S, and Saltzman, W. M. (1999) Oral anti-idiotypic antibody to Chlamydial GLXA reduces genital infection and dissemination to joints. The FASEB Journal, 13, A288.
87. Whittum-Hudson, J., Rudy, D., Vora, G., Hudson, A., Saltzman, W. M. and Stuart, E. S. (2000) Protection against murine genital infection by the anti-idiotypic antibody (mAb2) mimic of Chlamydial GLXA. *Proc. Fourth Eur. Chlamydia Research Meeting, August* 2000, 4, 429.
88. Bavoil, P. M. and Wyrick, P. B. (2006) *Chlamydia: Genomics and Pathogenesis* Taylor and Francis, Inc., Norwich, UK.
89. Carabeo, R. A., Mead, D. J. and Hackstadt, T. (2003) Golgi-dependent transport of cholesterol to the *Chlamydia trachomatis* inclusion. *Proceedings of the National Academy of Sciences*, 100, 6771-6776.
90. Grassme, H. U. C., Ireland, R. M. and Vanputten, J. P. M. (1996) Gonoccocal Opacity Protein Promotes Bacterial entry-Associated Rearrangements of the Epithelial Cell Actin Cytoskeleton. *Infection and Immunity,* 64, 1621-1630.
91. Scidmore, M. A., Fischer, E. R. and Hackstadt, T. (1996) Sphingolipids and glycoproteins are differentially trafficked to the *Chlamydia trachomatis* inclusion. *J Cell Biol,* 134, 363-74.
92. Gabel, B. R., Elwell, C., van Ijzendoorn, S. C. and Engel, J. N. (2004) Lipid raft-mediated entry is not required for *Chlamydia trachomatis* infection of cultured epithelial cells. *Infect Immun,* 72, 7367-73.
93. Stuart, E. S., Webley, W. C. and Norkin, L. C. (2003) Lipid rafts, caveolae, caveolin-1, and entry by Chlamydiae into host cells. *Exp Cell Res,* 287, 67-78.
94. Stuart, E. S., Wyrick, P. B., Choong, J., Stoler, S. B. and MacDonald, A. B. (1991) Examination of chlamydial glycolipid with monoclonal antibodies: cellular distribution and epitope binding. 74, 740-747.
95. Panyam, J., Zhou, W. Z., Prabha, S., Sahoo, S. K. and Labhasetwar, V. (2002) Rapid endo-lysosomal escape of poly(DL-lactide-co-glycolide) nanoparticles: implications for drug and gene delivery. *Faseb J,* 16, 1217-26.
96. Grupping, A. Y., Cnop, M., Van Schravendijk, C. F., Hannaert, J. C., Van Berkel, T. J. and Pipeleers, D. G. (1997) Low density lipoprotein binding and uptake by human and rat islet beta cells. *Endocrinology,* 138, 4064-8.
97. Dreses-Werringloer, U., Padubrin, I., Zeidler, H. and Kohler, L. (2001) Effects of azithromycin and rifampin on *Chlamydia trachomatis* infection in vitro. *Antimicrob Agents Chemother,* 45, 3001-8.
98. Wolf, K. and Malinverni, R. (1999) Effect of azithromycin plus rifampin versus that of azithromycin alone on the eradication of *Chlamydia pneumoniae* from lung tissue in experimental pneumonitis. *Antimicrob Agents Chemother,* 43, 1491-3.
99. Nanagara, R., Li, F., Beutler, A., Hudson, A. and Schumacher, H. R., Jr. (1995) Alteration of *Chlamydia trachomatis* biologic behavior in synovial membranes. Suppression of surface antigen production in reactive arthritis and Reiter's syndrome. *Arthritis Rheum.,* 38, 1410-1417.
100. Whittum-Hudson, J. A., Rudy, D., Gerard, H., Vora, G., Davis, E., Haller, P. K., Prattis, S. M., Hudson, A. P., Saltzman, W. M. and Stuart, E. S. (2001) The anti-idiotypic antibody to chlamydial glycolipid exoantigen (GLXA) protects mice against genital infection with a human biovar of *Chlamydia trachomatis*. Vaccine, 19, 4061-71.
101. Campos, M., Pal, S., O'Brien, T. P., Taylor, H. R., Prendergast, R. A. and Whittum-Hudson, J. A. (1995) A chlamydial major outer membrane protein extract as a trachoma vaccine candidate. *Investigative Opthalmology and Visual Science,* 36, 1477-1491.
102. Chirgwin, J. M., Przybyla, A. E., MacDonald, R. J. and Rutter, W. J. (1979) Isolation of biologically active ribonucleic acid from sources enriched in ribonuclease. *Biochemistry,* 18, 5294-5299.
103. Chomczynski, P. and Sacchi, N. (1987) Single-step method of RNA isolation by acid guanidinium thiocyanate-phenol-chloroform extraction. *Anal. Biochem.,* 162, 156-159.
104. Drescher, K. M. and Whittum-Hudson, J. A. (1994) Muller cells are an intraretinal source of immunologic and antiviral cytokines. *Investigative Opthalmology and Visual Science,* 35 (Suppl), 1482.
105. Drescher, K. M. and Whittum-Hudson, J. A. (1996) Modulation of immune-associated surface markers and cytokine production by murine retinal glial cells. *J. Neuroimmunol.,* 64, 71-81.
106. Drescher, K. M. and Whittum-Hudson, J. A. (1996) HSV-1 alters transcript levels of TNF' and IL-6 in retinal glial cells. *Investigative Opthalmology and Visual Science,* 37, 2302-2312.
107. Drescher, K. M. and Whittum-Hudson, J. A. (1997) Evidence for induction of interferon-' and interferon-a in retinal glial cells of Muller. *Virology,* 234, 309-316.
108. Akpek, E. A., Jabs, D. A., Gerard, H. C., Prendergast, R. A., Hudson, A. P., Lee, B. and Whittum-Hudson, J. A. (2004) Chemokines in autoimmune lacrimal gland disease in MRL/MpJ mice. *Invest Opthalmol. Vis. Sci.,* 45, 185-190.
109. Gerard, H. C., Wang, Z., Whittum-Hudson, J. A., El-Gabalawy, H., Goldbach-Mansky, R., Bardin, T., Schumacher, H. R. and Hudson, A. P. (2002) Cytokine and chemokine mRNA produced in synovial tissue chronically infected with *Chlamydia trachomatis* and *C. pneumoniae J. Rheumatol.,* 29, 1827-1835.
110. Whittum-Hudson, J., Farazdaghi, M. and Prendergast, R. A. (1985) A role for T lymphocytes in preventing experimental herpes simplex virus type 1-induced retinitis. *Invest Opthalmol Vis Sci,* 26, 1524-32.

Example 20

Comparison of Free and Nanoparticle-Encapsulated Antibiotics

Figure 20:
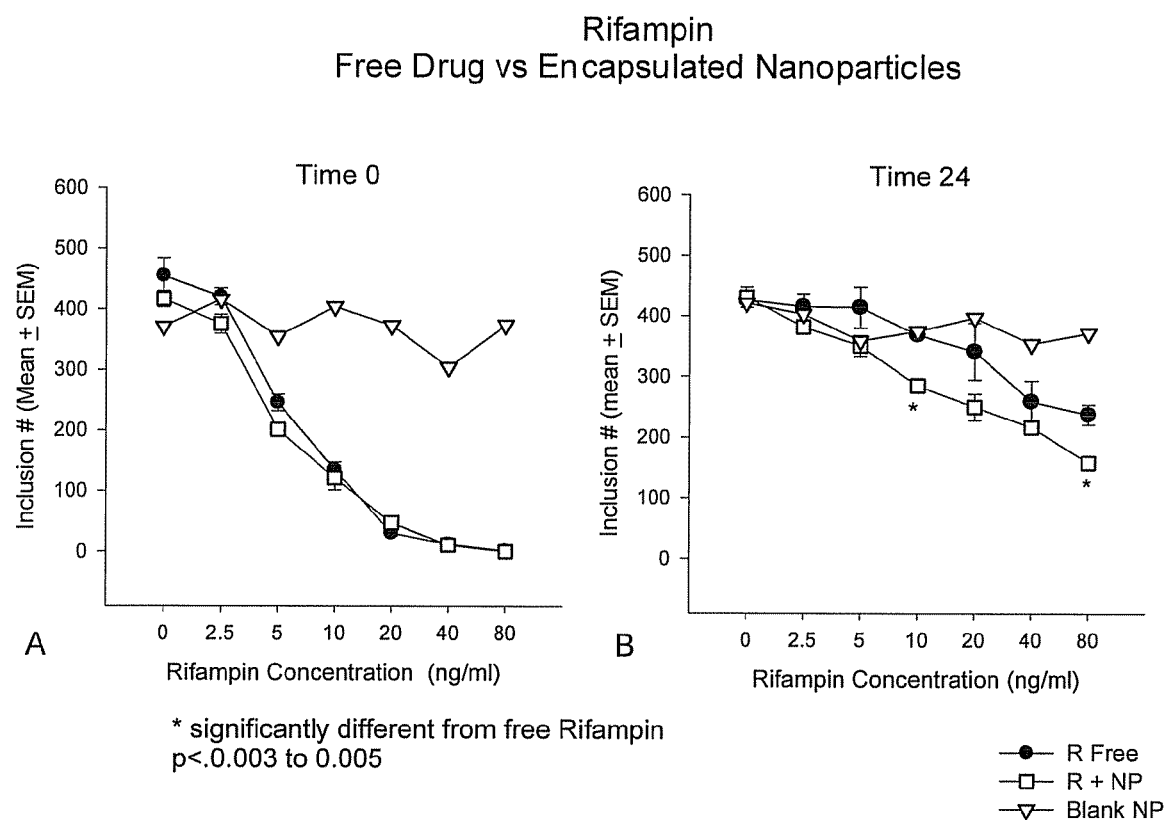
FIG. 20.

Free and nanoparticle-encapsulated antibiotics added at either t0 (time of infection) or after 24 hr of infection (t24), were compared along with blank nanoparticles as controls. As shown in FIG. 20, blank particles at the same particle concentrations used for each antibiotic had no effect on inclusion numbers even at the higher concentrations of nanoparticles. In this same experiment, rifampin-loaded nanoparticles significantly reduced inclusion counts near the MIC50 to the highest drug concentration. Similar results were obtained for Azithromycin added at t0, but results for the latter in nanoparticles did not differ from free drug with t24 hr addition.

Figure 21:
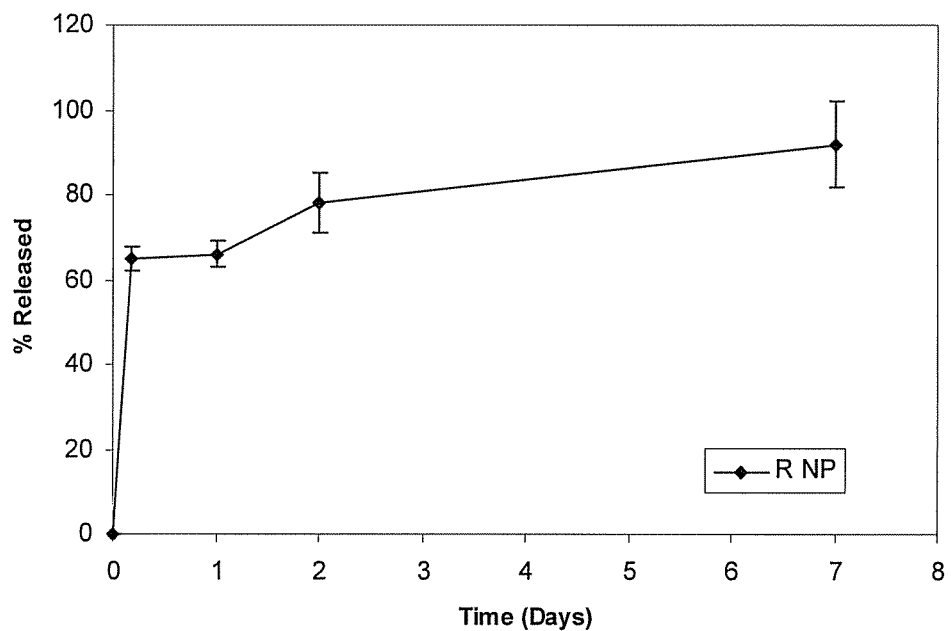
FIG. 21. Rifampin release from nanoparticles in phosphate buffered saline (pH 7.4) containing 0.1% Tween 80 and 0.1%

Rifampin is highly unstable in solution compared to Azithromycin (the t½ of Rifampin is hours compared to days for Azithromycin). The data herein suggest that encapsulation of Rifampin increases the effective t½ of this antibiotic. In vitro release experiments under simulated physiologic conditions showed that nanoparticles release about 60% of the encapsulated rifampin in 24 hrs and the remainder is released over 7 days (FIG. 21). Increased t½ by delivery of antibiotics or other drugs encapsulated in nanoparticles has important implications for in vivo therapeutic applications.

All publications herein are incorporated by reference to the same extent as if each individual publication or patent application was specifically and individually indicated to be incorporated by reference.

One skilled in the art will recognize many methods and materials similar or equivalent to those described herein, which could be used in the practice of the present invention. Indeed, the present invention is in no way limited to the methods and materials described.

What is claimed is:
1. A method of treating a persistent intracellular *Chlamydia* bacterial infection in a patient in need of such treatment, comprising administering to said patient a therapeutically effective amount of folic acid-conjugated nanoparticles comprising at least one antibiotic agent, wherein said antibiotic agent is effective against said persistent intracellular *Chlamy-*

*dia* bacterial infection and wherein at the time of treatment, *Chlamydia* of said infection lack ftsK transcription or lack ftsK and ftsW transcription.

2. The method of claim 1, wherein said antibiotic is selected from the group consisting of azithromycin, amoxicillin, rifampicin, erythromycin, erythromycin ethylsuccinate, ofloxacin, levofloxacin doxycycline, and tetracycline.

3. The method of claim 1, wherein said nanoparticles comprise a biodegradable polymer, one or more antibiotics, an imaging agent and folic acid attached to nanoparticles through a spacer.

4. The method of claim 3, wherein said spacer is PEG.

5. The method of claim 1, wherein said *Chlamydia* is selected from the group consisting of *C. trachomatis, C. pneumoniae*, and *C. psittaci*.

6. A method for inhibiting the growth of *C. pneumonia* or *C. trachomatis* causing a persistent intracellular *Chlamydia* infection comprising contacting said *C. pneumonia* or *C. trachomatis*, or a cell containing said *C. pneumonia* or *C. trachomatis*, with a composition comprising nanoparticles conjugated with folic acid, wherein said particles comprise a first antibiotic in a form and in a dosage suitable for treatment of a persistent intracellular *Chlamydia* infection wherein *Chlamydia* of said infection lack ftsK transcription or lack ftsK and ftsW transcription at the time the composition is administered.

7. A method of imaging *Chlamydia* infection in a mammal having a persistent intracellular *Chlamydia* infection, comprising
   a) administering to said mammal a composition comprising nanoparticles comprising folic acid and at least one imaging agent, and
   b) detecting said nanoparticles in said mammal, wherein said particles target folic acid receptor-expressing cells infected with a persistent intracellular *Chlamydia* infection wherein *Chlamydia* of said infection lack ftsK transcription or lack ftsK and ftsW transcription.

8. The method of claim 7, wherein said nanoparticles are fluorescently labeled.

\* \* \* \* \*